(12) United States Patent
Anémain et al.

(10) Patent No.: US 9,598,637 B2
(45) Date of Patent: Mar. 21, 2017

(54) PHOSPHORUS-CONTAINING METAL COMPLEXES

(71) Applicant: Merck Patent GmbH, Darmstadt (DE)

(72) Inventors: Rémi M. Anémain, Seoul (KR);
Burkhard Koenig, Lappersdorf (DE);
Claire De Nonancourt, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/694,609

(22) Filed: Apr. 23, 2015

(65) Prior Publication Data

US 2015/0232749 A1 Aug. 20, 2015

Related U.S. Application Data

(62) Division of application No. 13/825,654, filed as application No. PCT/EP2011/004418 on Sep. 1, 2011, now Pat. No. 9,040,512.

(30) Foreign Application Priority Data

Sep. 24, 2010 (DE) .................. 10 2010 046 512

(51) Int. Cl.
| | | |
|---|---|---|
| *H01L 29/08* | (2006.01) | |
| *H01L 35/24* | (2006.01) | |
| *H01L 51/00* | (2006.01) | |
| *C09K 11/06* | (2006.01) | |
| *C07F 15/00* | (2006.01) | |
| *C09K 11/02* | (2006.01) | |
| *A61N 5/06* | (2006.01) | |
| *H01L 51/50* | (2006.01) | |
| *H01L 51/52* | (2006.01) | |

(52) U.S. Cl.
CPC ............ *C09K 11/06* (2013.01); *A61N 5/062* (2013.01); *C07F 15/0033* (2013.01); *C09K 11/025* (2013.01); *H01L 51/0085* (2013.01); *C09K 2211/185* (2013.01); *H01L 51/5016* (2013.01); *H01L 51/5072* (2013.01); *H01L 51/5088* (2013.01); *H01L 51/5096* (2013.01); *H01L 51/5221* (2013.01); *H01L 2251/301* (2013.01); *H01L 2251/308* (2013.01)

(58) Field of Classification Search
None
See application file for complete search history.

(56) References Cited

U.S. PATENT DOCUMENTS

| 6,835,469 B2 | 12/2004 | Kwong et al. | |
|---|---|---|---|
| 9,040,512 B2 * | 5/2015 | Anemian | C07F 15/0033 514/183 |
| 2003/0072964 A1 | 4/2003 | Kwong et al. | |
| 2004/0138455 A1 | 7/2004 | Stossel et al. | |
| 2005/0123791 A1 | 6/2005 | Deaton et al. | |
| 2007/0048546 A1 | 3/2007 | Ren | |
| 2007/0176542 A1 | 8/2007 | Ragini et al. | |
| 2007/0178332 A1 | 8/2007 | Ragini et al. | |
| 2007/0249834 A1 | 10/2007 | Stossel et al. | |
| 2007/0267959 A1 | 11/2007 | Ragini et al. | |
| 2008/0103308 A1 | 5/2008 | Ragini et al. | |
| 2008/0200677 A1 | 8/2008 | Stoessel et al. | |
| 2009/0048415 A1 | 2/2009 | Buesing et al. | |
| 2012/0261651 A1 | 10/2012 | Noto et al. | |

FOREIGN PATENT DOCUMENTS

| CN | 1589307 A | 3/2005 |
|---|---|---|
| CN | 102668156 A | 9/2012 |
| DE | 102005032332 A1 | 1/2007 |
| JP | 2005506361 A | 3/2005 |
| JP | 2007/308498 A | 11/2007 |
| JP | 2009/507865 A | 2/2009 |

(Continued)

OTHER PUBLICATIONS

Fraysse et al., "Unexpected Formation of a Scrambled Aryl-Phosphine Oxide Under Modified Sonogashira Conditions", *Tetrahedron Letters*, vol. 40, pp. 9249-9250 (1999).

Zhou et al., "Metallophosphors of Platinum with Distinct Main-Group Elements: A Versatile Apprach Towards Color Tuning and White-Light Emission with Superior Efficiency/Color Quality/Brightness Trade-Offs", *Journal of Materials Chemistry*, vol. 20, pp. 7472-7484 (2010).

Wadman, Sipke H., et al., "Cyclo-Ruthenated and -Platinated Complexes Bearing Phosphonate Substituents", Inorganica Chimica Acta, vol. 363, (2010), pp. 1701-1706.

Zhou, Guijiang, et al., "Robust Tris-Cyclometalated Iridium (III) Phosphors with Ligands for Effective Charge Carrier Injection/Transport: Synthesis, Redox, Photophysical, and Electrophosphorescent Behavior", Chem. Asian J., vol. 3, (2008), pp. 1830-1841.

(Continued)

*Primary Examiner* — Jeffrey H Murray
(74) *Attorney, Agent, or Firm* — Drinker Biddle & Reath LLP

(57) ABSTRACT

The present invention relates, to metal complexes having improved solubility, to processes for the preparation of the metal complexes, to devices comprising these metal complexes and to the use of the metal complexes. Specifically, disclosed herein are electronic device comprising a compound of a formula $M(L)_n(L')_m$, where the compound contains a moiety $M(L)_n$ of the formulae (24) to (29), for example, formula (24)

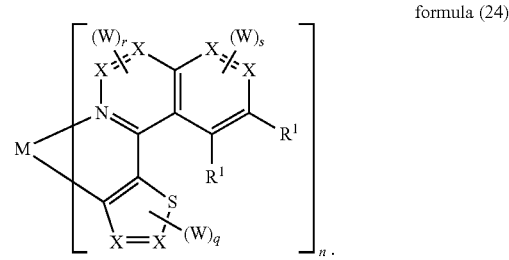

9 Claims, No Drawings

(56) References Cited

FOREIGN PATENT DOCUMENTS

| | | |
|---|---|---|
| JP | 2011176063 A | 9/2011 |
| WO | WO-02/068435 A1 | 9/2002 |
| WO | WO-03033617 A1 | 4/2003 |
| WO | WO-2005113563 A1 | 12/2005 |
| WO | WO-2007027440 A1 | 3/2007 |
| WO | WO-2010089394 A1 | 8/2010 |
| WO | WO-2011021385 A1 | 2/2011 |
| WO | WO-2011059719 A2 | 5/2011 |
| WO | WO-2011059791 A2 | 5/2011 |

OTHER PUBLICATIONS

Schneider, Jacob, et al., "Synthesis, Electrochemistry, Photophysics, and Solvatochromism in New Cyclometalated 6-Phenyl-4-(p-R-phenyl)-2,2'-bipyridyl (R=Me, COOMe, P(O)(OEt)$_2$) (CNN) Platinum(II) Thiophenolate Chromophores", Inorganic Chemistry, vol. 48, No. 4, (2009), pp. 1498-1506.

Schneider, Jacob, et al., "Cyclometalated 6-Phenyl-2,2'-bipyridyl (CNN) Platinum(II) Acetylide Complexes: Structure, Electrochemistry, Photophysics, and Oxidative- and Reductive-Quenching Studies", Inorganic Chemistry, vol. 48, No. 10, (2009), pp. 4306-4316.

Bolink, Henk J., et al., "Green Light-Emitting Solid-State Electrochemical Cell Obtained from a Homoleptic Iridium(III) Complex Containing Ionically Charged Ligands", Chem. Mater., vol. 18, (2006), pp. 2778-2780.

Zhou, Guijiang, et al., "Manipulating Charge-Transfer Character with Electron-Withdrawing Main-Group Moieties for the Color Tuning of Iridium Electrophosphors", Adv. Funct. Mater., vol. 18, (2008), pp. 499-511.

International Search Report for PCT/EP2011/004418 mailed Oct. 31, 2011.

* cited by examiner

PHOSPHORUS-CONTAINING METAL COMPLEXES

CROSS-REFERENCE TO RELATED APPLICATIONS

This application is a divisional application of U.S. patent application Ser. No. 13/825,654, filed on Jun. 3, 2013, which is a national stage application (under 35 U.S.C. §371) of PCT/EP2011/004418, filed Sep. 1, 2011, which claims benefit of German application 10 2010 046 512.7, filed Sep. 24, 2010 which are both incorporated by reference.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., Appl. Phys. Lett. 1999, 75, 4-6). For quantum-mechanical reasons, an up to four-fold energy and power efficiency is possible using organometallic compounds as phosphorescence emitters. In general, however, there is still a need for improvement in OLEDs which exhibit triplet emission, in particular with respect to efficiency, operating voltage and lifetime. This applies, in particular, to OLEDs which emit in the relatively short-wave region, i.e. green and blue. Furthermore, many phosphorescent emitters do not have adequate solubility for processing from solution, meaning that there is also a further need for improvement here.

In accordance with the prior art, the triplet emitters employed in phosphorescent OLEDs are, in particular, iridium and platinum complexes, which are usually employed as cyclometallated complexes. The ligands here are frequently derivatives of phenylpyridine. However, the solubility of such complexes is frequently low, which makes processing from solution more difficult or prevents it completely.

The prior art discloses iridium complexes which are substituted by an optionally substituted aryl or heteroaryl group on the phenyl ring of the phenylpyridine ligand in the para-position to the coordination to the metal (WO 2004/026886 A2). Improved solubility of the complexes was thereby achieved. However, there is also still a further need for improvement here with respect to the solubility and the efficiency and lifetime of the complexes.

Surprisingly, it has been found that certain metal chelate complexes described in greater detail below have improved solubility and furthermore result in improvements in the organic electroluminescent device, in particular with respect to the efficiency and lifetime. The present invention therefore relates to these metal complexes and to organic electroluminescent devices which comprise these complexes.

The invention relates to a compound of the formula (1), $$M(L)_n(L')_m \quad \text{formula (1)}$$

where the compound of the general formula (1) contains a moiety $M(L)_n$ of the formula (2):

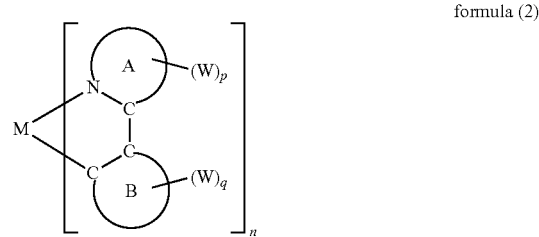

formula (2)

where M is bonded to any desired bidentate ligand L via a nitrogen atom N and via a carbon atom C and where A can be any desired heteroaromatic condensed ring system and where B can be any desired aromatic or heteroaromatic ring or any desired aromatic or heteroaromatic ring system, which is condensed and/or non-condensed, and where the following applies to the symbols and indices used:

M is a metal selected from the group consisting of iridium, rhodium, platinum, palladium; osmium and ruthenium, preferably iridium, rhodium, platinum and palladium;

L' is, identically or differently on each occurrence, any desired co-ligand;

W is, identically or differently on each occurrence, a radical of the formulae (3) and (4)

formula (3)

formula (4)

where V is equal to S or O;

$R_4$ is, identically or differently on each occurrence, H, D, F, Cl, Br, I, $N(R^2)_2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy, alkylaryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^4$ here may also form a mono- or polycyclic, aliphatic, aromatic and/or benzo-fused ring system with one another;

R² is, identically or differently on each occurrence, H, D, F, Cl, Br, I, N(R³)₂, CN, NO₂, Si(R³)₃, B(OR³)₂, C(=O)R³, P(=O)(R³)₂, S(=O)R³, S(=O)₂R³, OSO₂R³, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals R³, where one or more non-adjacent CH₂ groups may be replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms may be replaced by D, F, Cl, Br, I, ON or NO₂, or an aromatic or heteroaromatic ring system having 5 to 60 aromatic ring atoms, which may in each case be substituted by one or more radicals R³, or an aryloxy, arylalkoxy, alkylaryloxy or heteroaryloxy group having 5 to 60 aromatic ring atoms, which may be substituted by one or more radicals R³, or a diarylamino group, diheteroarylamino group or arylheteroarylamino group having 10 to 40 aromatic ring atoms, which may be substituted by one or more radicals R³, or a combination of two or more of these groups; two or more adjacent radicals R² here may form a mono- or polycyclic, aliphatic or aromatic ring system with one another;

R³ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents R³ here may also form a mono- or polycyclic, aliphatic or aromatic ring system with one another;

q is an integer greater than or equal to 0;

p is an integer greater than or equal to 0; with the proviso that p+q is an integer greater than or equal to 1;

n is 1, 2 or 3 for M equal to iridium or rhodium and is 1 or 2 for M equal to platinum or palladium;

m is 0, 1, 2, 3 or 4;

the indices n and m here are selected so that the coordination number on the metal corresponds to 6 for M equal to iridium or rhodium and corresponds to 4 for M equal to platinum or palladium;

a plurality of ligands L here may also be linked to one another or L may be linked to L' via any desired bridge Z and thus form a tridentate, tetradentate, pentadentate or hexadentate ligand system.

In a preferred embodiment of the present invention, the ligands L are not bridged with one another, neither are the ligands L bridged with the ligands L'.

In a further preferred embodiment of the present invention, M(L)ₙ from formula (1) is equal to the formulae (5) or (6).

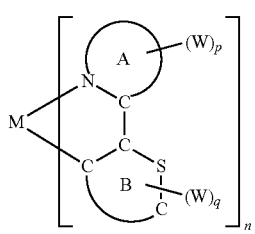

formula (5)

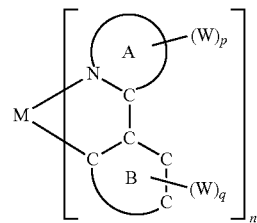

formula (6)

In a very preferred embodiment of the present invention, M(L)ₙ from formula (1) is equal to the formulae (7) and (8).

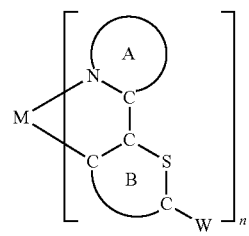

formula (7)

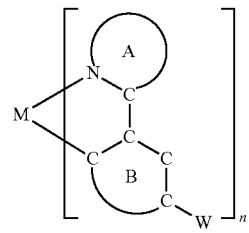

formula (8)

In a further preferred embodiment of the present invention, M(L)ₙ from formula (1) is equal to the formula (9).

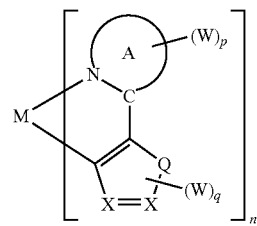

formula (9)

where the following applies to the symbols in indices used:

X is, identically or differently on each occurrence, CR¹ or N;

Q is, identically or differently on each occurrence, R'C=CR¹, R¹C=N, O, S, Se or NR¹;

R¹ is, identically or differently on each occurrence, H, D, F, Cl, Br, I, N(R²)₂, CN, NO₂, Si(R²)₃, B(OR²)₂, C(=O)R², P(=O)(R²)₂, S(=O)R², S(=O)₂R², OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals R², where one or more non-adjacent CH₂ groups may be replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy, arylalkoxy or heteroaryloxy group having 5 to 60 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$, or a combination of two or more of these groups; two or more radicals R$^1$ here may also form a mono- or polycyclic, aliphatic, aromatic and/or benzo-fused ring system with one another. For the other symbols and indices, the above definitions apply.

Preference is furthermore given for the purposes of the invention to moieties M(L)$_n$ having the formula (10)

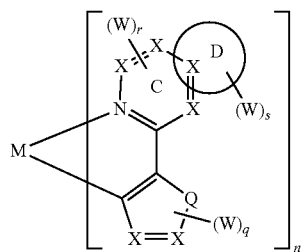

formula (10)

where the equation p=r+s applies to the indices r and s and, owing to p+q≥1, r+s+q≥1 also applies, and the aromatic or heteroaromatic ring D, which is condensed onto C in any desired and possible manner, where D can be an aromatic or heteroaromatic ring or an aromatic or heteroaromatic condensed and/or non-condensed ring system.

In a further preferred embodiment of the present invention, the ring D is an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$, or a combination of two or more of these groups; two or more radicals R$^1$ here may also form a mono- or polycyclic, aliphatic, aromatic and/or benzo-fused ring system with one another.

In a particularly preferred embodiment of the present invention, the ring D is equal to the formula (11)

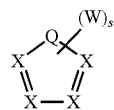

formula (11)

In a very particularly preferred embodiment of the present invention, the moiety M(L)$_n$ of the formula (1) is selected from the following formulae (12) to (17)

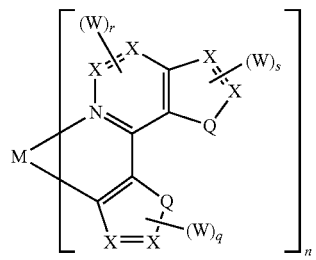

formula (12)

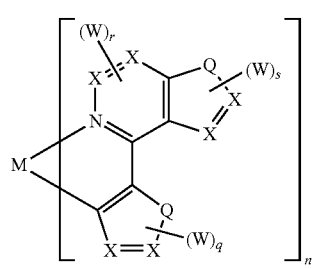

formula (13)

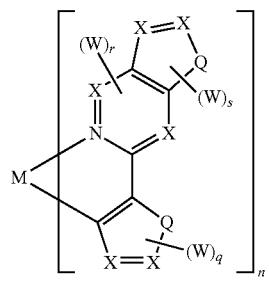

formula (14)

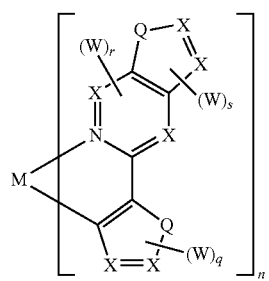

formula (15)

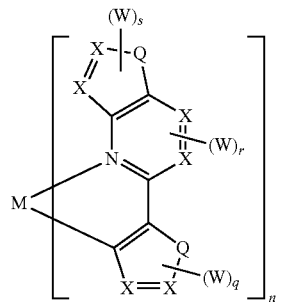

formula (16)

-continued

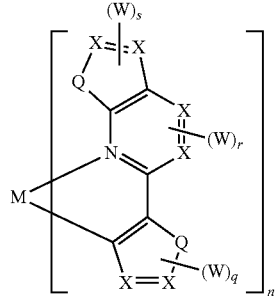

formula (17)

Furthermore preferred embodiments for the purposes of the present invention are moieties M(L)$_n$ of the formula (1) having the formulae (18) to (23)

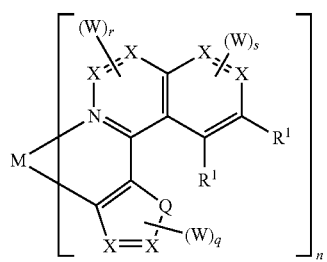

formula (18)

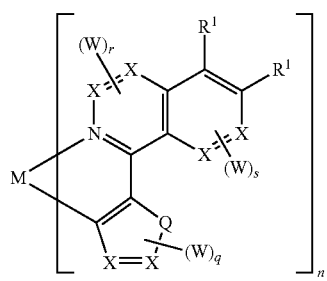

formula (19)

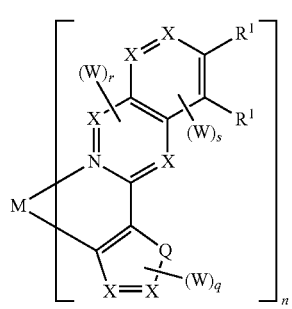

formula (20)

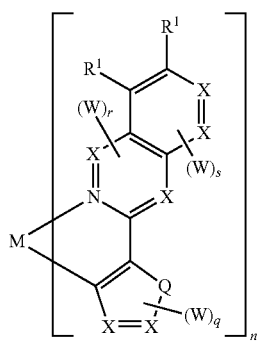

formula (21)

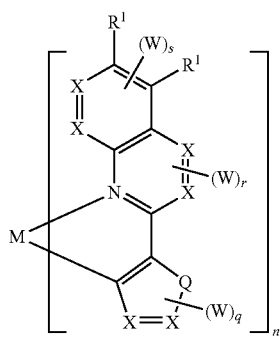

formula (22)

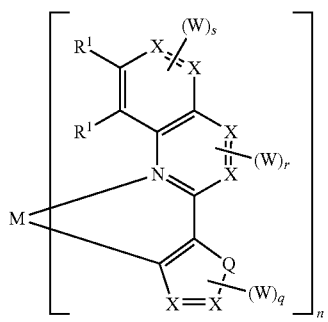

formula (23)

It is furthermore particularly preferred for the purposes of the present invention for the radical Q to be either S or R$^1$C=CR$^1$.

Very preferred embodiments of the present invention are compounds of the formula (1) containing the moieties M(L)$_n$ of the following formulae (24) to (29).

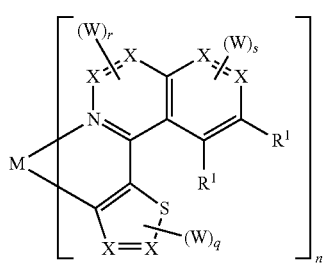

formula (24)

-continued
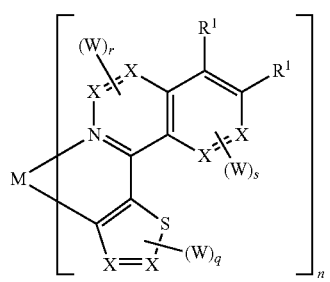
formula (25)
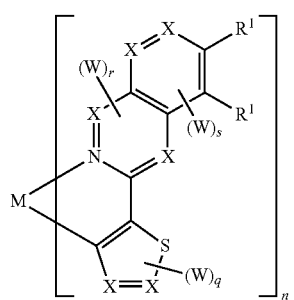
formula (26)
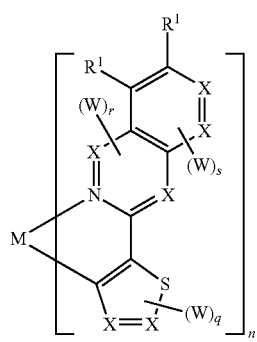
formula (27)
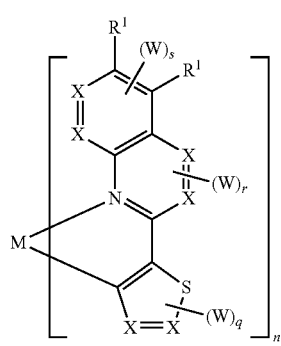
formula (28)
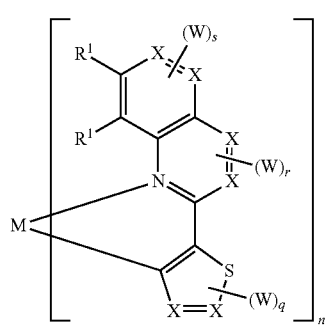
formula (29)
Very particularly preferred embodiments of the present invention are compounds of the formula (1) containing the moieties $M(L)_n$ of the following formulae (30) to (35).
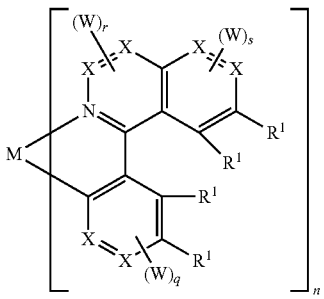
formula (30)
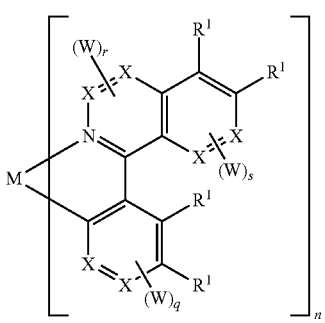
formula (31)
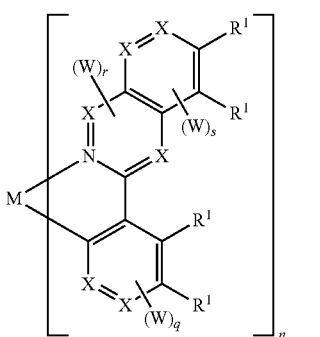
formula (32)
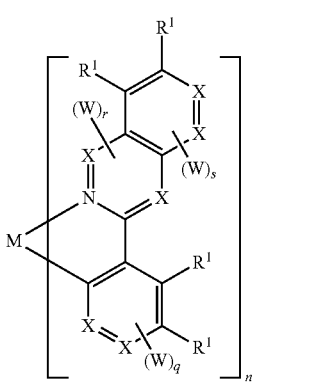
formula (33)

formula (34)

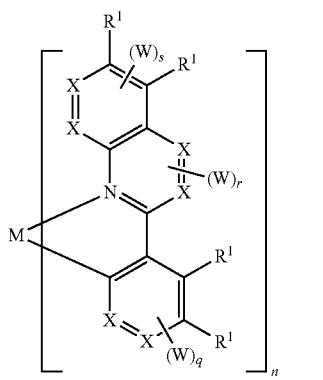

formula (35)

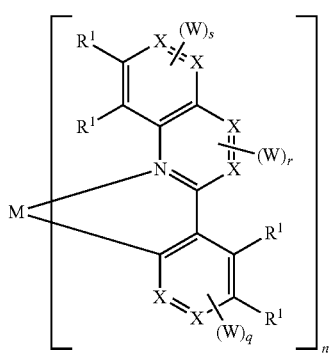

In an especially preferred embodiment of the present invention, q+r+s=1.

Preference is furthermore given for the purposes of the present invention to compounds of the formula (1) containing the moiety $M(L)_n$ characterised in that r=0 and thus: q+s≥1. In a very preferred embodiment of the present invention: q+s=1, where the radical W can be at any desired and possible position of the rings and replaces the substituent $R^1$ there. If the radical W is bonded to the ligand via X, X is equal to $CR^1$ and the radical W again replaces the radical $R^1$.

Particular preference is given for the purposes of the present invention to compounds of the formula (1) containing the moiety $M(L)_n$ of the formulae (36) to (59).

formula (36)

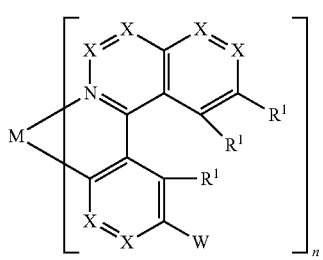

formula (37)

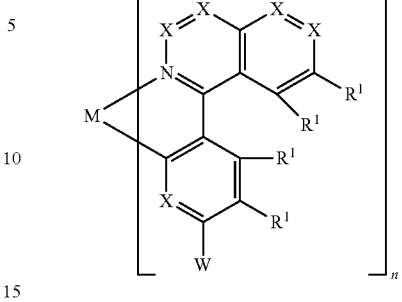

formula (38)

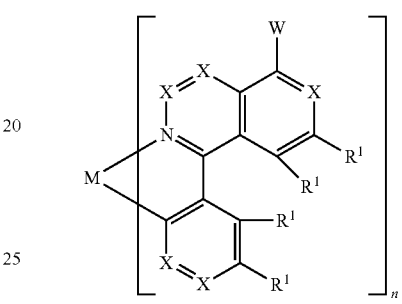

formula (39)

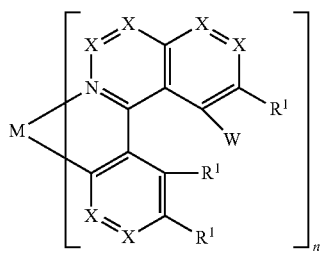

formula (40)

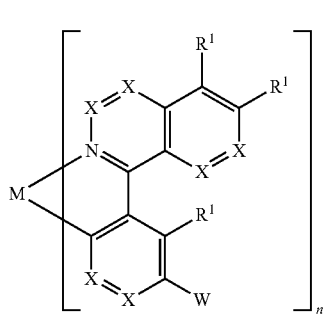

formula (41)

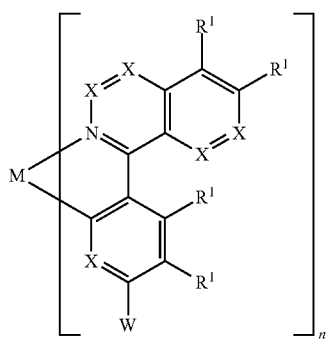

formula (42)
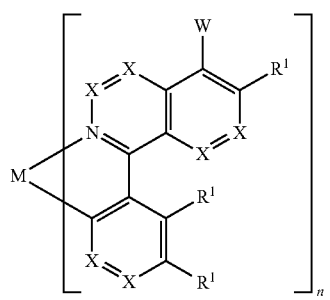
formula (43)
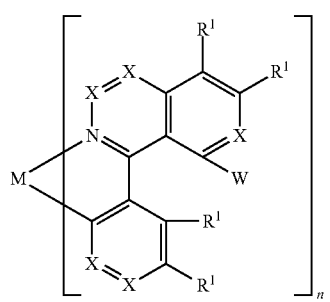
formula (44)
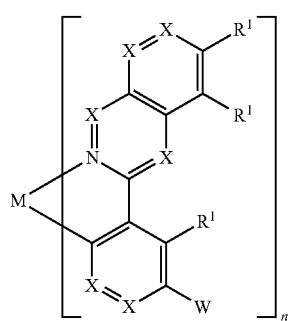
formula (45)
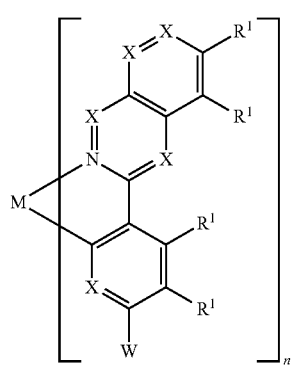
formula (46)
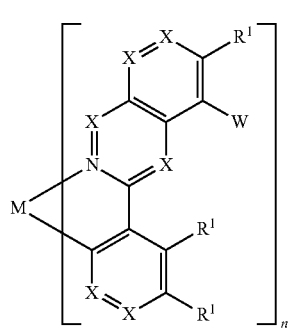
formula (47)
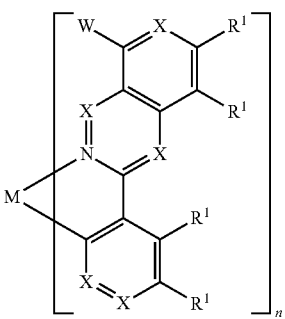
formula (48)
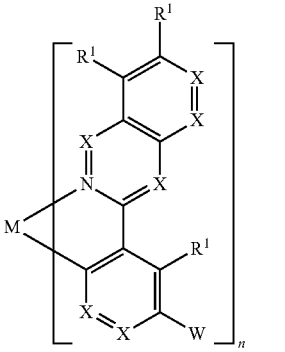
formula (49)
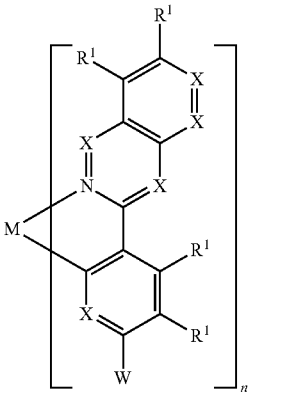
formula (50)
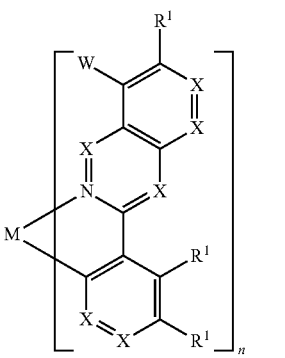

formula (51)
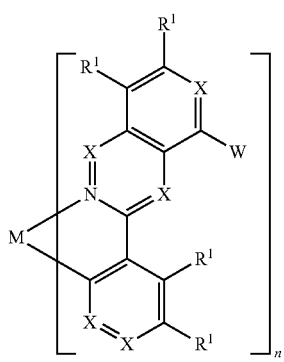
formula (52)
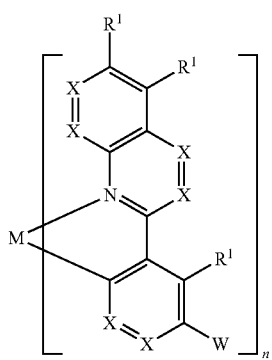
formula (53)
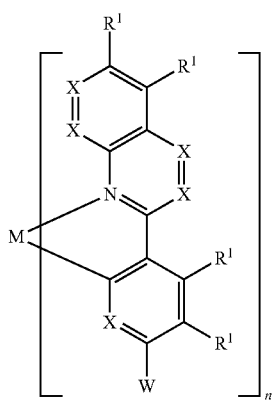
formula (54)
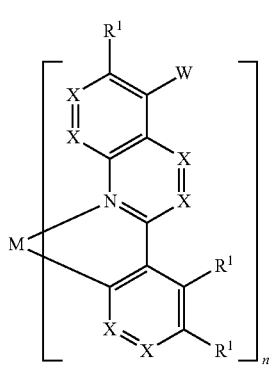
formula (55)
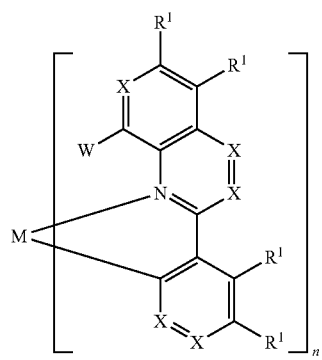
formula (56)
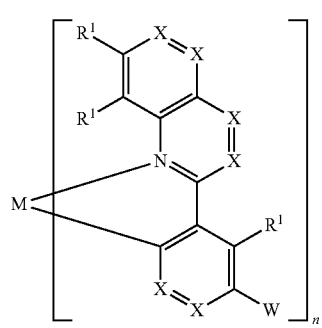
formula (57)
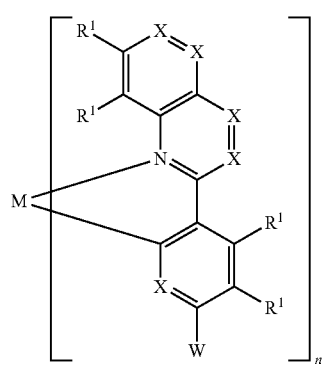
formula (58)
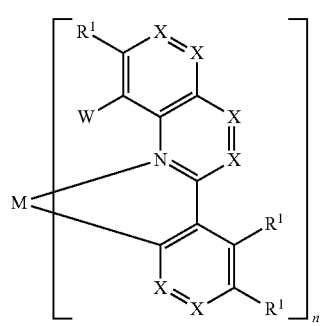

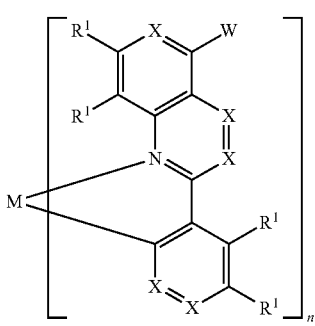

formula (59)

Very particularly preferred embodiments of the present invention are furthermore compounds of the formula (1) containing a moiety M(L)$_n$ of the formulae (36), (37), (40), (41), (44), (45), (48), (49), (52), (53), (56) and (57).

Very particularly preferred embodiments of the present invention are also compounds of the formula (1) containing a moiety M(L)$_n$ of the formulae (36), (37), (40) and (41).

Especially preferred embodiments of the present invention are compounds of the formula (1) containing a moiety M(L)$_n$ of the formulae (36) and (40).

The substituents R$^1$ can result in a bridge within a ligand L which result in further stiffening of the ligand. Preferred embodiments in the sense of the invention are the formulae (60) to (97).

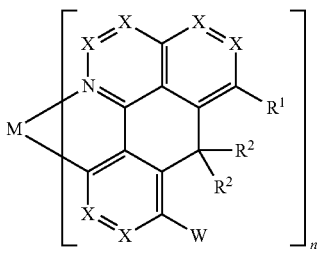

formula (60)

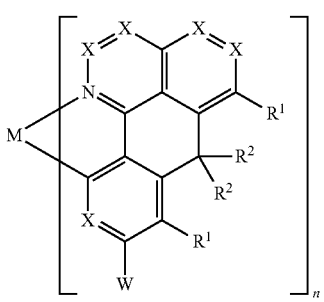

formula (61)

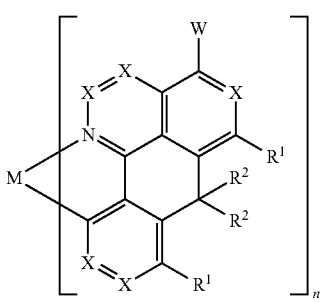

formula (62)

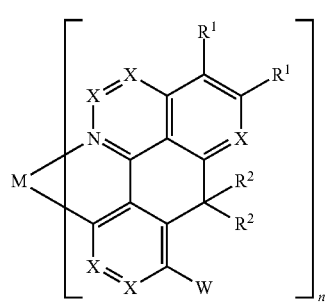

formula (63)

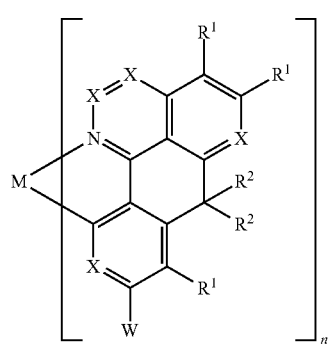

formula (64)

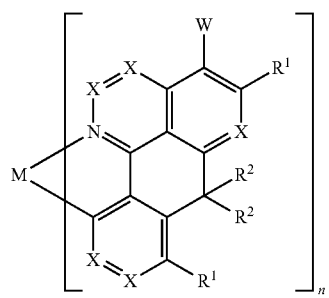

formula (65)

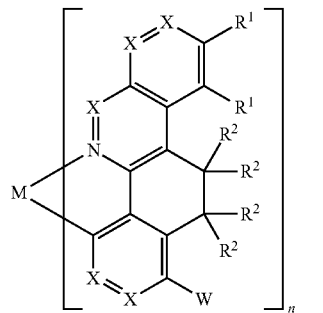

formula (66)

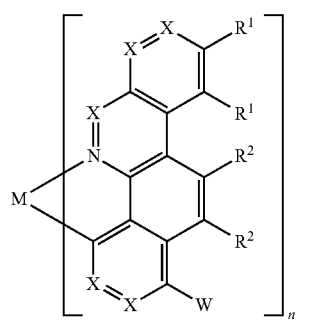

formula (67)

formula (68)
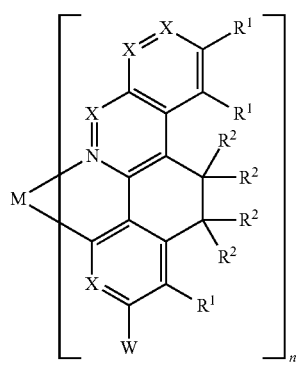
formula (69)
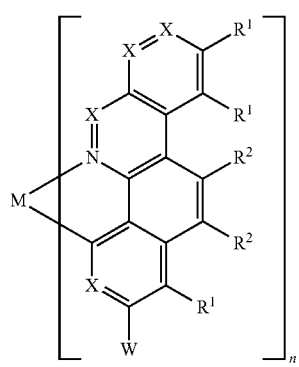
formula (70)
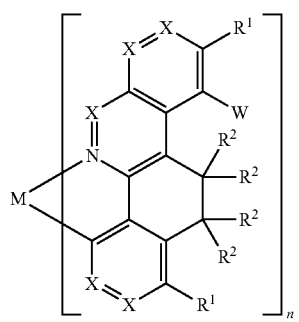
formula (71)
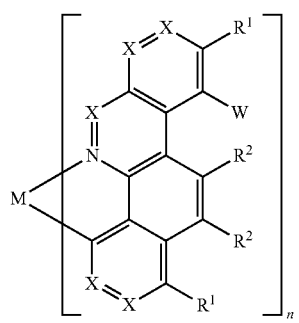
formula (72)
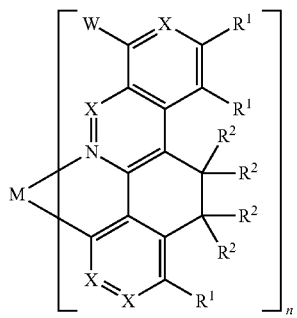
formula (73)
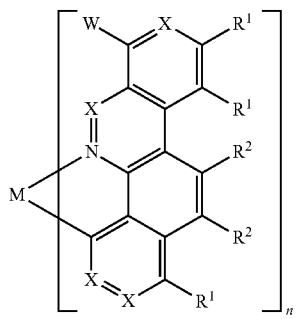
formula (74)
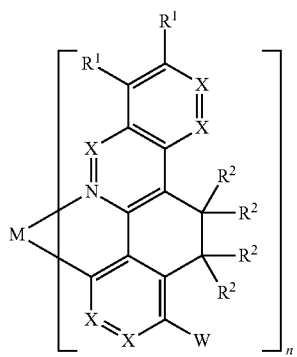
formula (75)
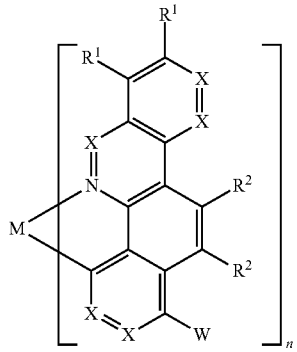

-continued
formula (76)
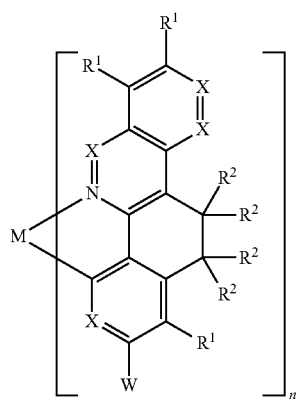
formula (77)
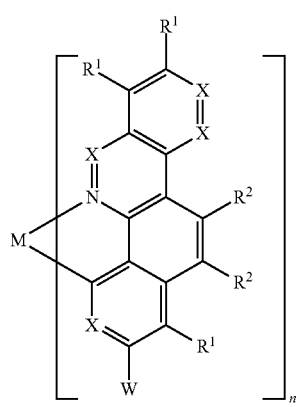
formula (78)
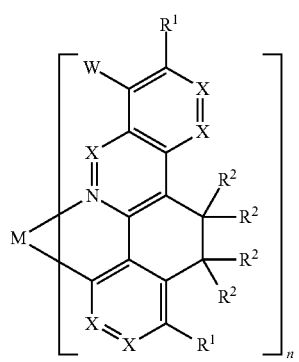
formula (79)
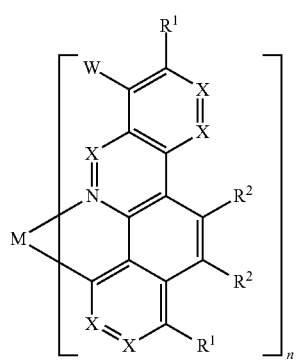
formula (80)
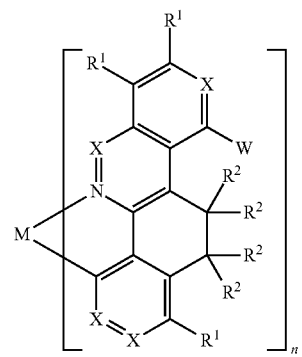
formula (81)
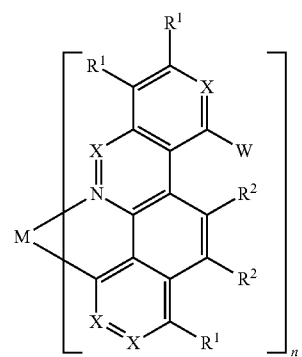
formula (82)
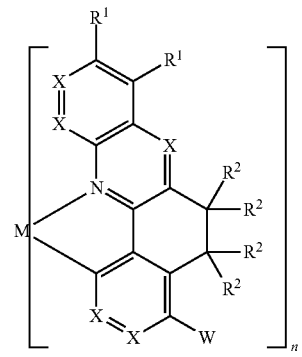
formula (83)
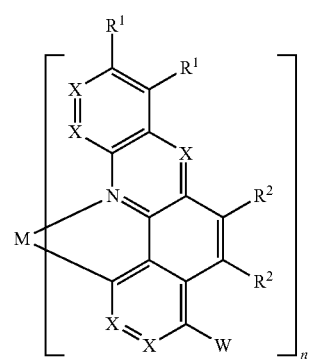

-continued
formula (84)
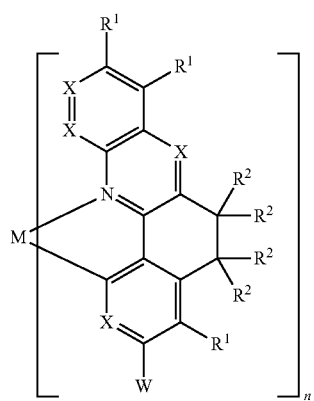
formula (85)
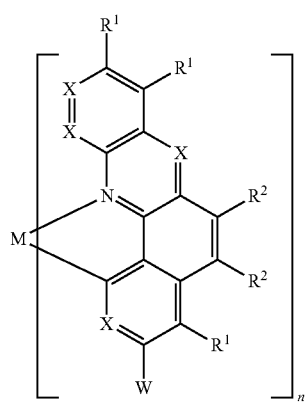
formula (86)
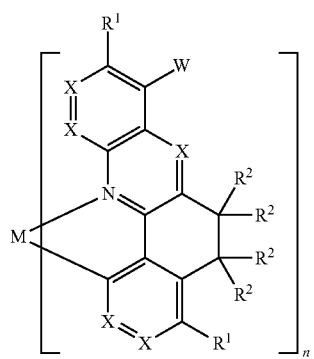
formula (87)
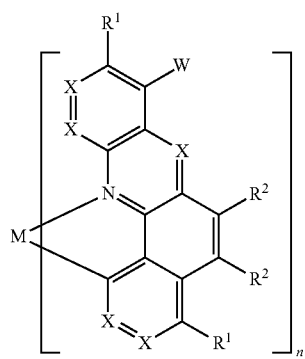
-continued
formula (88)
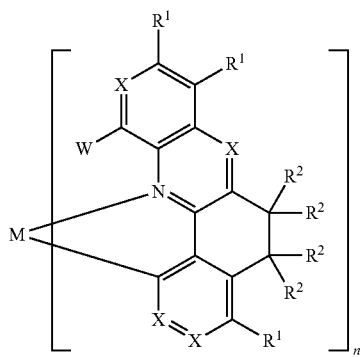
formula (89)
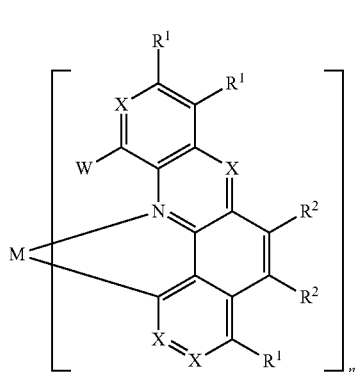
formula (90)
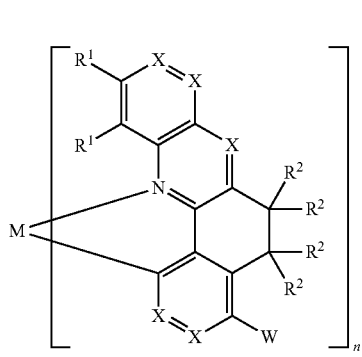
formula (91)
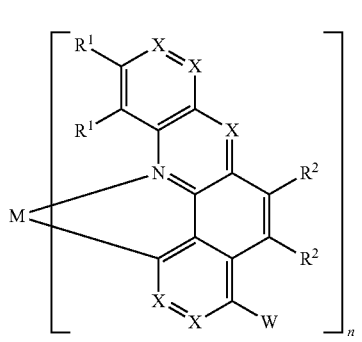

formula (92)
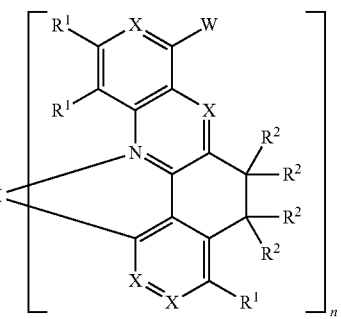

formula (93)
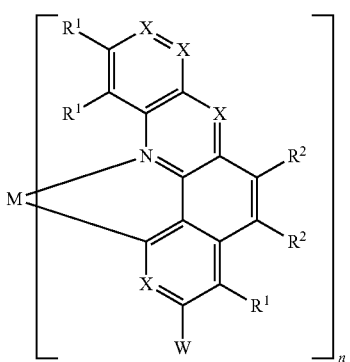

formula (94)
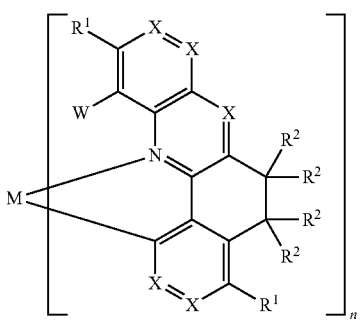

formula (95)
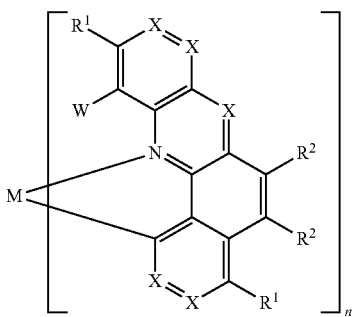

formula (96)
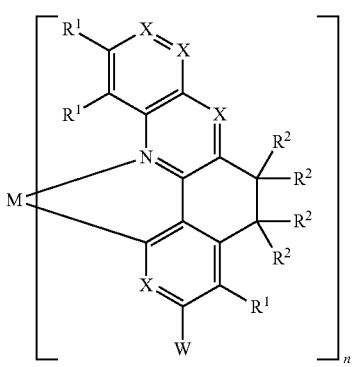

formula (97)
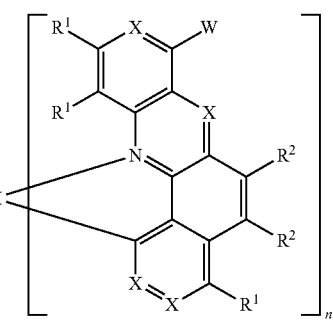

In an especially preferred embodiment of the present invention, X is equal to $CR^1$.

In a further preferred embodiment of the present invention, $R^1$ is, identically or differently on each occurrence, H, D, F, Cl, Br, I, $N(R^2)_2$, CN, $NO_2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C{=}CR^2$, $C{\equiv}C$, $Si(R^2)_2$, $Ge(R^2)_2$, $Sn(R^2)_2$, $C{=}O$, $C{=}S$, $C{=}Se$, $C{=}NR^2$, $P({=}O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another.

In a further very preferred embodiment of the present invention, the moiety $M(L)_n$ of the compounds of the formula (1) is selected from the formulae (98) to (109).

formula (98)
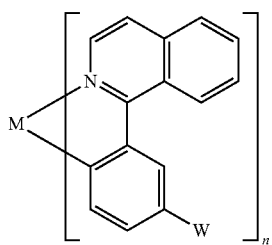
formula (99)
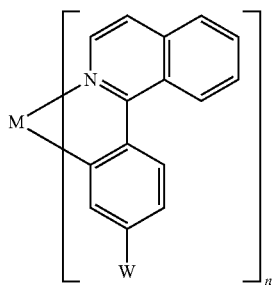
formula (99a)
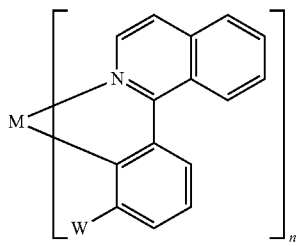
formula (99b)
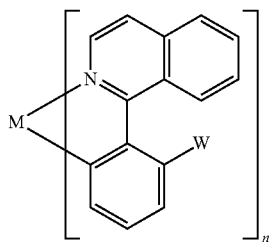
formula (100)
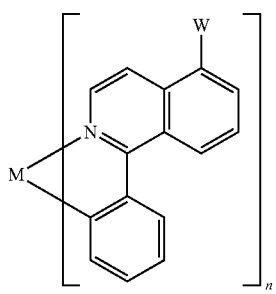
formula (101)
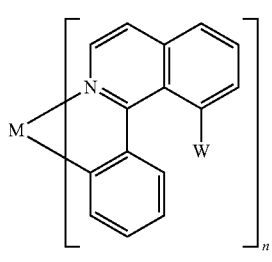
formula (101a)
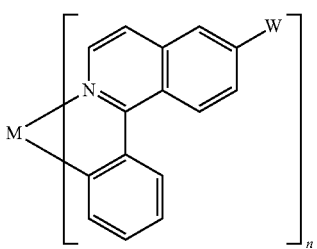
formula (101b)
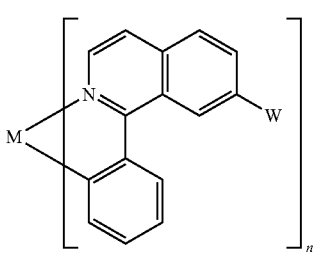
formula (102)
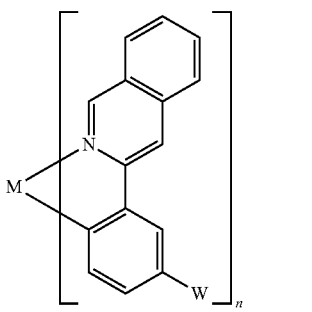
formula (103)
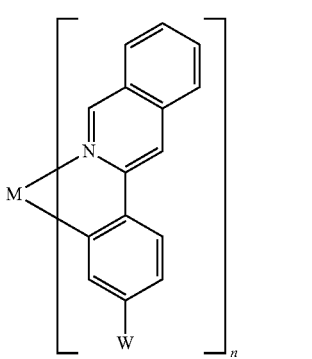
formula (103a)
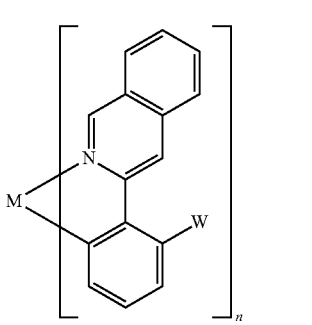

formula (103b)
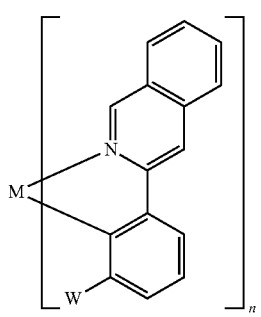
formula (104)
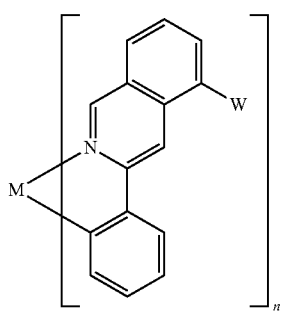
formula (105)
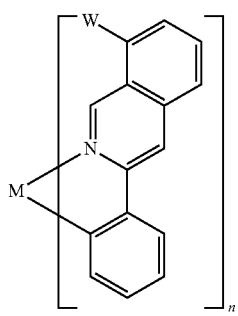
formula (105a)
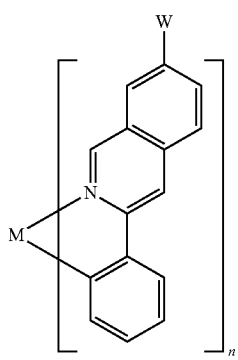
formula (105b)
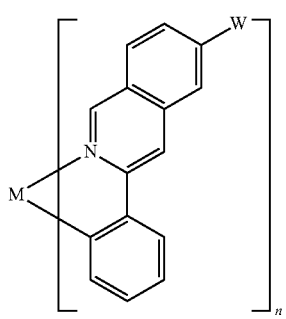
formula (106)
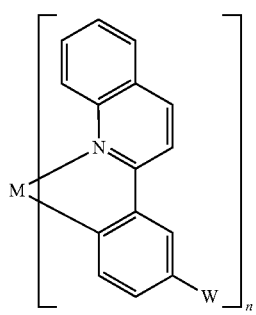
formula (107)
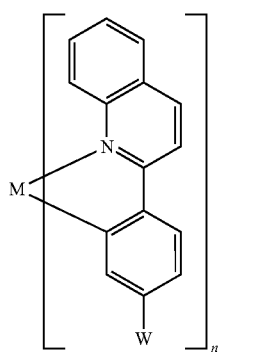
formula (107a)
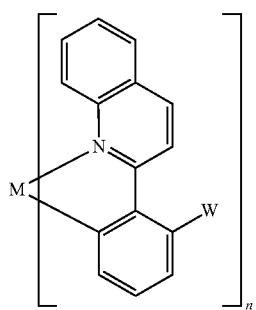
formula (107b)
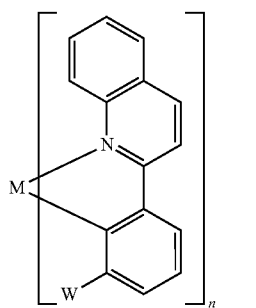
formula (108)
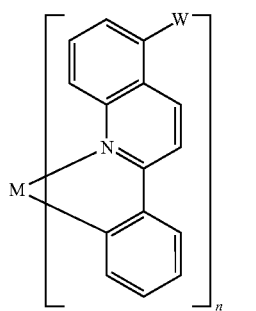

formula (109)

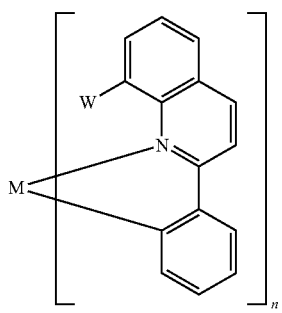

formula (109a)

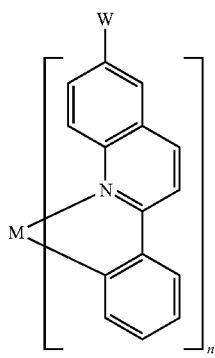

formula (109b)

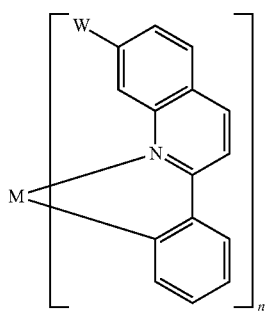

Very particular preference is given here to the formulae (98), (99), (100), (101), (101a), (101b), (102), (103), (104), (105), (105a), (105b), (106), (107), (108), (109), (109a) and (109b). Very particular preference is furthermore given to the formulae (98), (99), (100), (101), (102), (103), (104), (105), (106), (107), (108) and (109). The formulae (98) and (99) are especially preferred here.

In a preferred embodiment of the present invention, the radical W is selected from the radicals of the formulae (110) to (115).

formula (110)

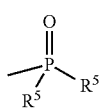

formula (111)

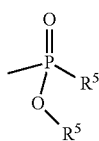

formula (112)

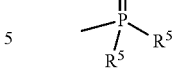

formula (113)

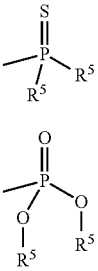

formula (114)

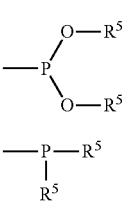

formula (115)

—P—$R^5$
|
$R^5$ where
$R^5$ is, identically or differently on each occurrence, H, D, a straight-chain alkyl or thioalkoxy group having 1 to 40 C atoms or a straight-chain alkenyl or alkynyl group having 2 to 40 C atoms or a branched or cyclic alkyl, alkenyl, alkynyl or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, C=$NR^2$, P(=O)($R^2$), SO, $SO_2$, $NR^2$, O, S or $CONR^2$ and where one or more H atoms may be replaced by D, F, Cl, Br, I, CN or $NO_2$, or an aromatic or heteroarmatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another and the hyphen has the same meaning as everywhere else within the present invention. It denotes the bond from the radical to the ligand.

In a very preferred embodiment of the present invention, the radical W is equal to the formula (110).

In a preferred embodiment of the present invention, the radical $R^5$ is, identically or differently on each occurrence, H, D, a straight-chain alkyl group having 1 to 40 C atoms or a straight-chain alkenyl or alkynyl group having 2 to 40 C atoms or a branched or cyclic alkyl, alkenyl, alkynyl group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, C=$NR^2$, P(=O)($R^2$), SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another and In a very preferred embodiment of the present invention, the radical $R^5$ is selected from the formulae (116) to (286), where the formulae indicated may themselves be substituted by one or more radicals $R^3$, which may be identical or different on each occurrence.

formula (116)

formula (117)

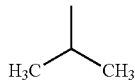

formula (118)

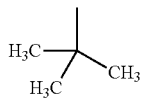

formula (119)

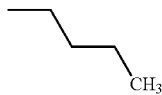

formula (120)

formula (121)

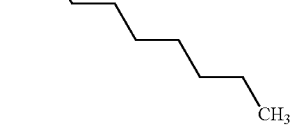

formula (122)

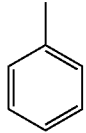

formula (123)

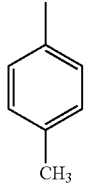

formula (124)

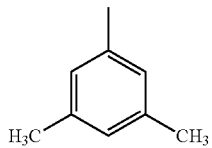

formula (125)

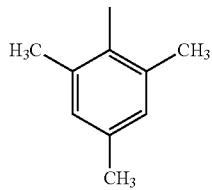

formula (126)

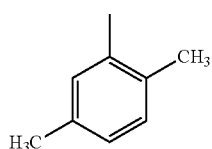

formula (127)

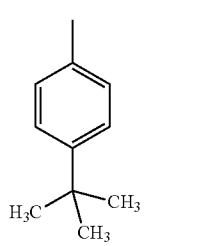

formula (128)

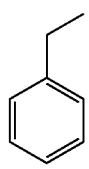

formula (129)

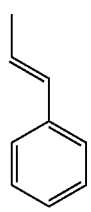

formula (130)

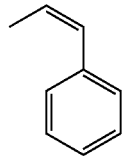

formula (131)

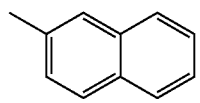

formula (132)

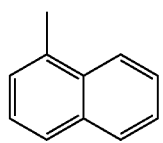

formula (133)

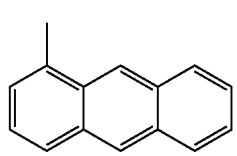

formula (134)
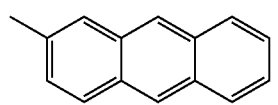
formula (135)
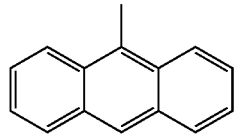
formula (136)
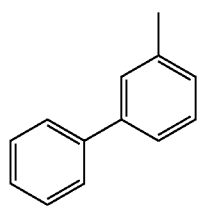
formula (137)
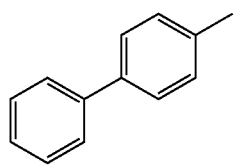
formula (138)
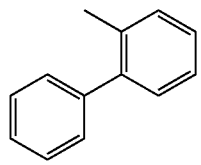
formula (139)
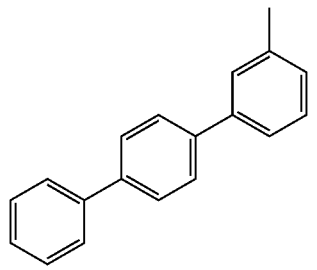
formula (140)
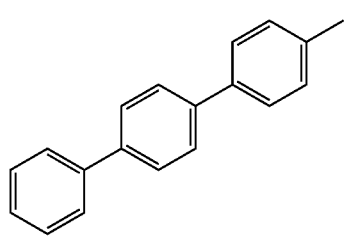
formula (141)
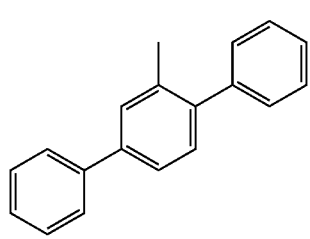
formula (142)
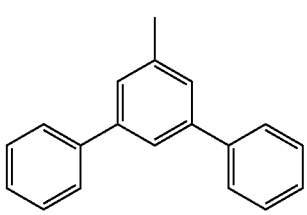
formula (143)
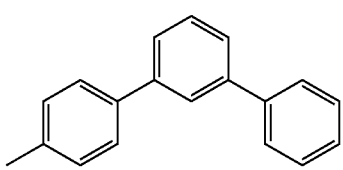
formula (144)
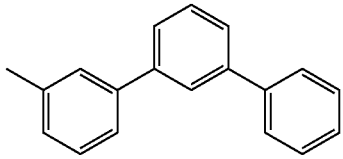
formula (145)
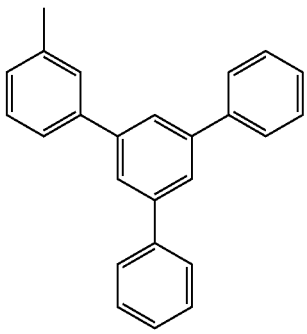
formula (146)
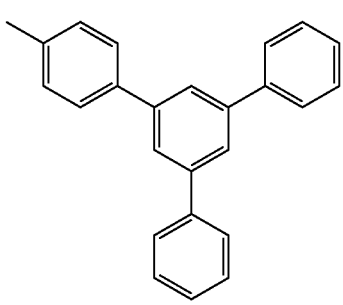
formula (147)
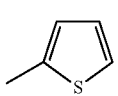
formula (148)
formula (149)
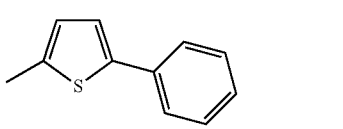

formula (150)
formula (151)
formula (152)
formula (153)
formula (154)
formula (155)
formula (156)
formula (157)
formula (158)
formula (159)
formula (160)
formula (161)
formula (162)
formula (163)
formula (164)
formula (165)
formula (166)
formula (167)
formula (168)
formula (169)
formula (170)
formula (171)
formula (172)
formula (173)
formula (174)

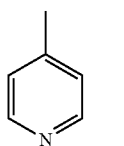
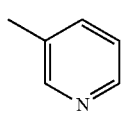
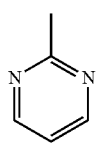
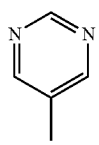
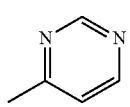
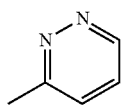
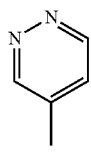
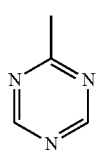
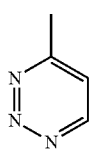
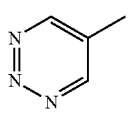
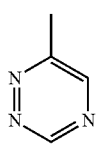
formula (175)
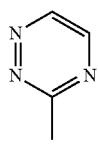
formula (176)
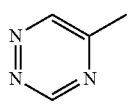
formula (177)
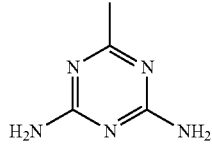
formula (178)
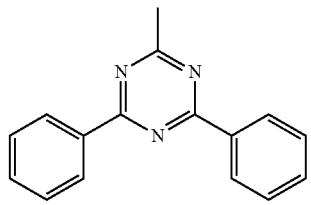
formula (179)
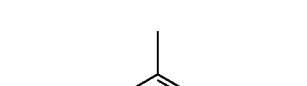
formula (180)
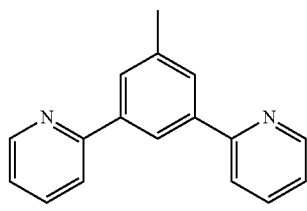
formula (181)
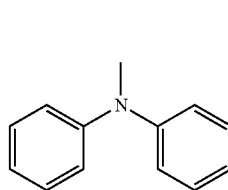
formula (182)
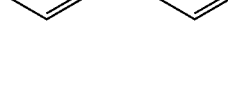
formula (183)
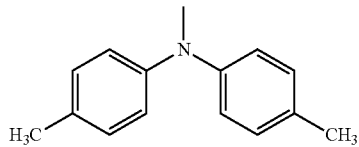
formula (184)
formula (185)
formula (186)
formula (187)
formula (188)
formula (189)
formula (190)
formula (191)
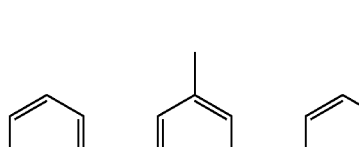
formula (192)
formula (193)
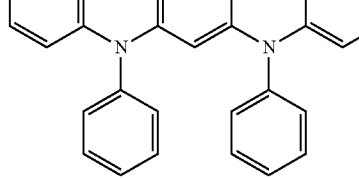

formula (194)
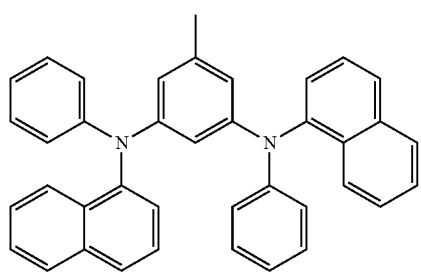
formula (195)
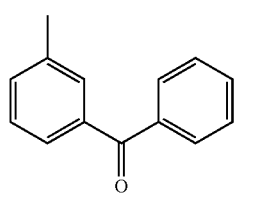
formula (196)
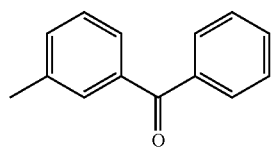
formula (197)
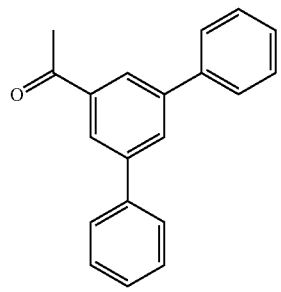
formula (198)
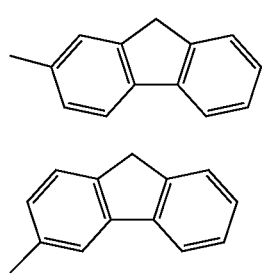
formula (199)
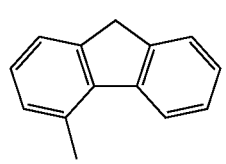
formula (200)
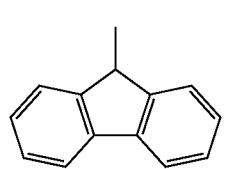
formula (201)
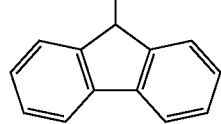
formula (202)
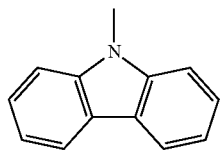
formula (203)
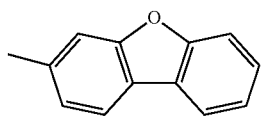
formula (204)
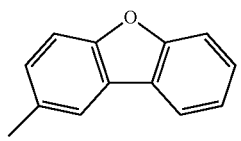
formula (205)
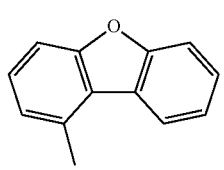
formula (206)
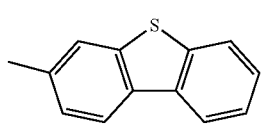
formula (207)
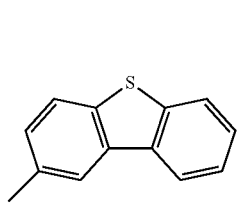
formula (208)
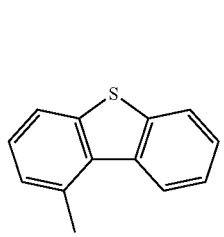
formula (209)
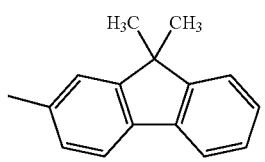
formula (210)
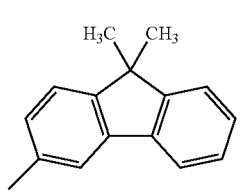

-continued
formula (211)
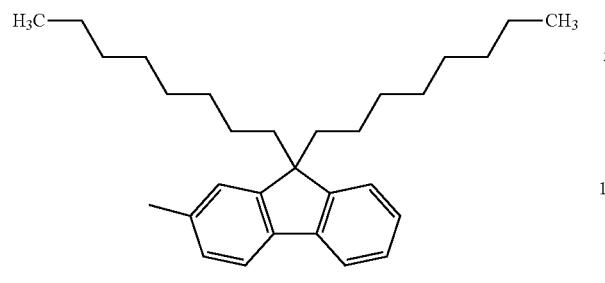
formula (212)
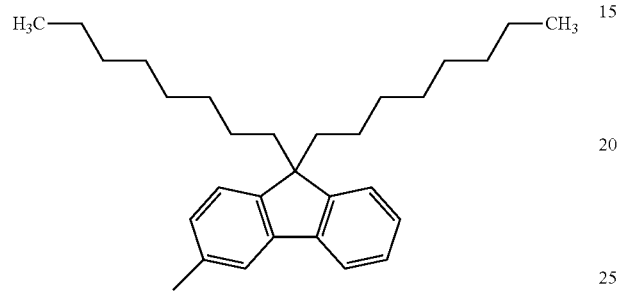
formula (213)
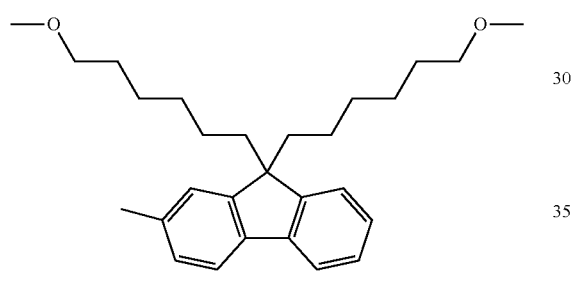
formula (214)
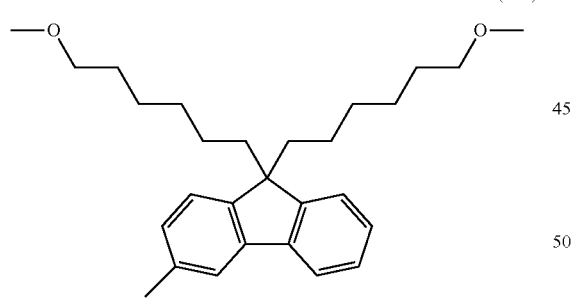
formula (215)
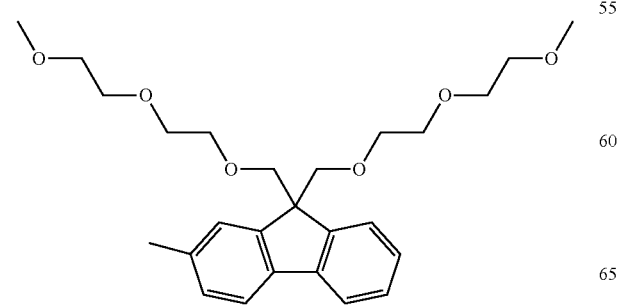
-continued
formula (216)
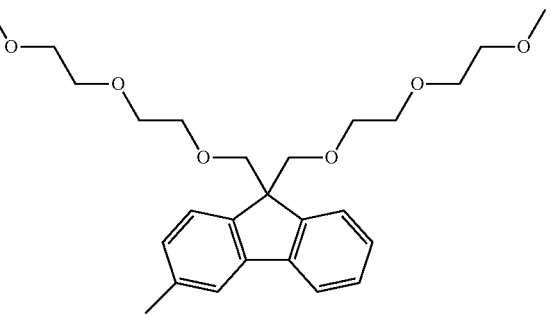
formula (217)
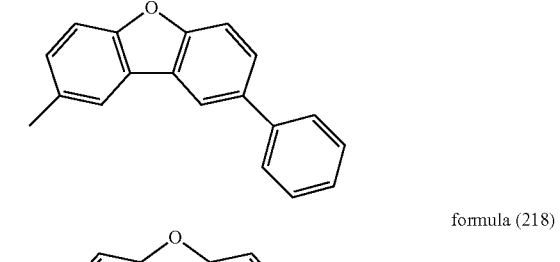
formula (218)
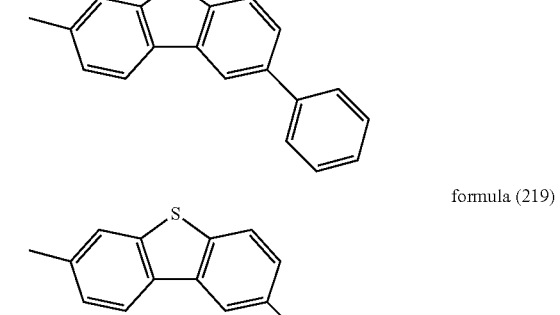
formula (219)
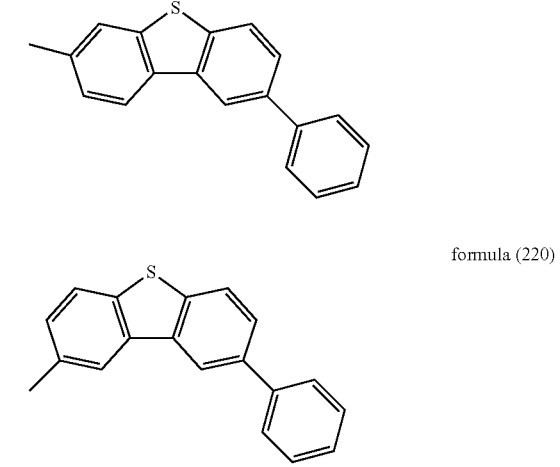
formula (220)
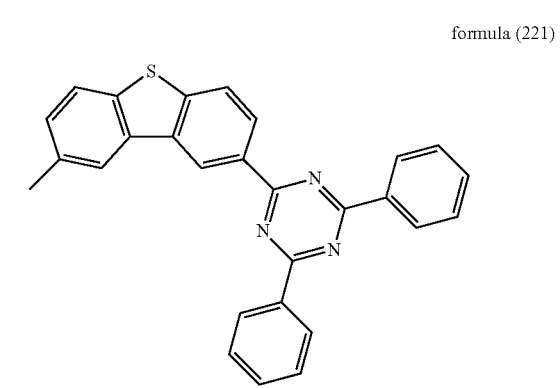
formula (221)

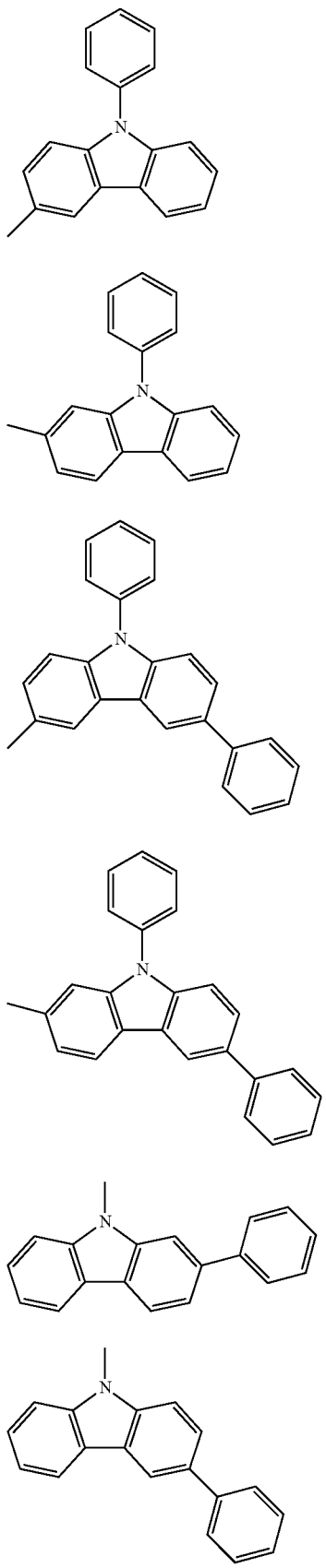
formula (222)
formula (223)
formula (224)
formula (225)
formula (226)
formula (227)
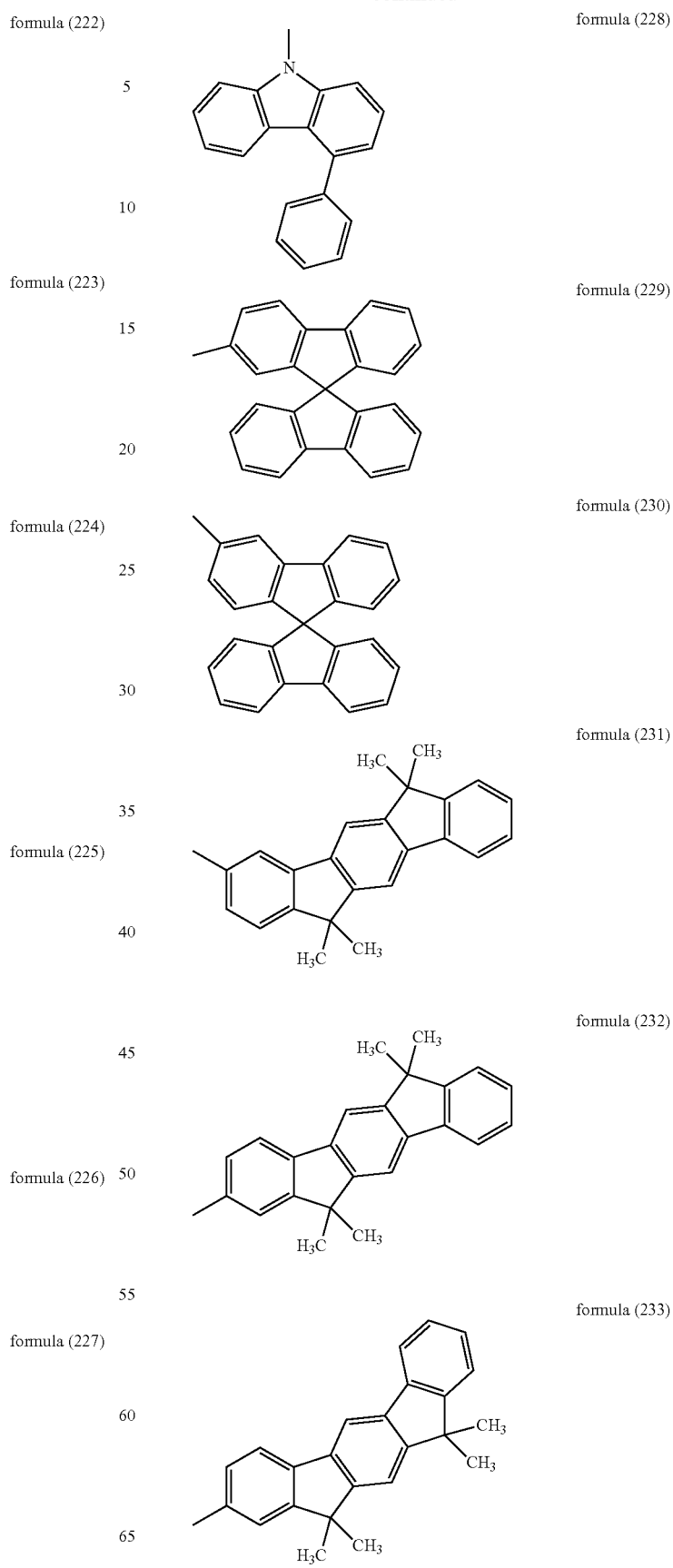
formula (228)
formula (229)
formula (230)
formula (231)
formula (232)
formula (233)

formula (234)
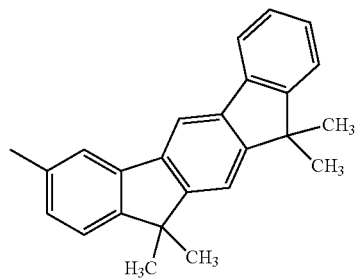
formula (235)
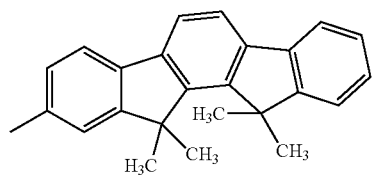
formula (236)
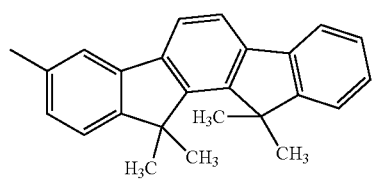
formula (237)
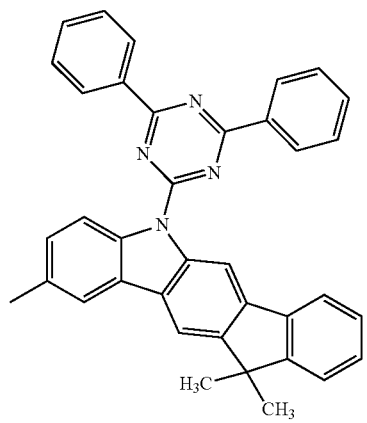
formula (238)
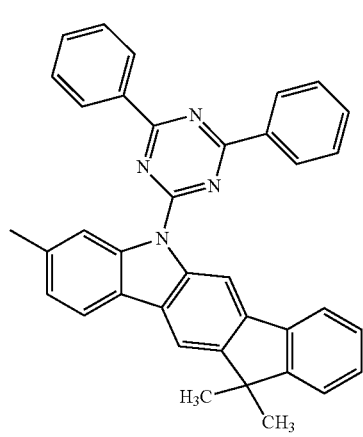
formula (239)
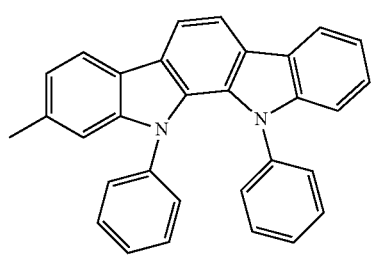
formula (240)
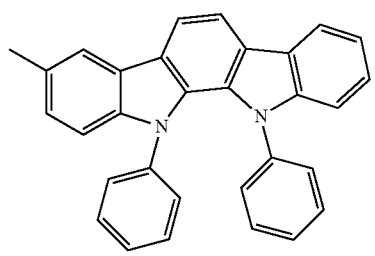
formula (241)
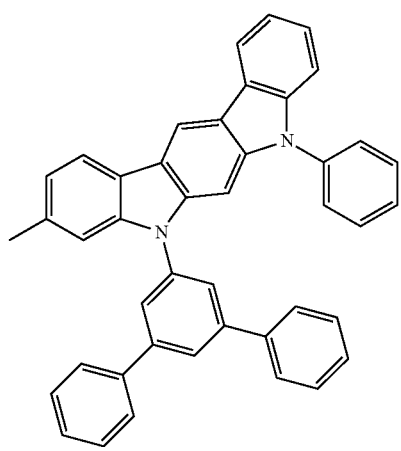
formula (242)
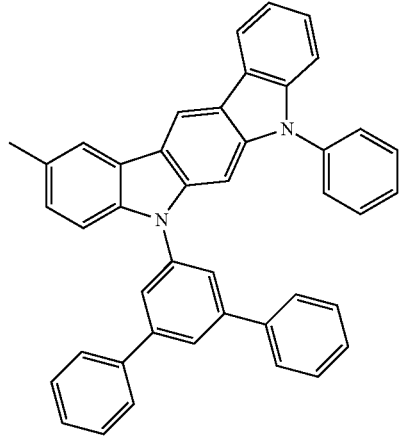

formula (243)
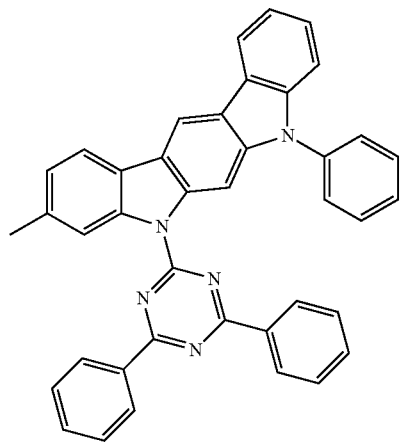
formula (244)
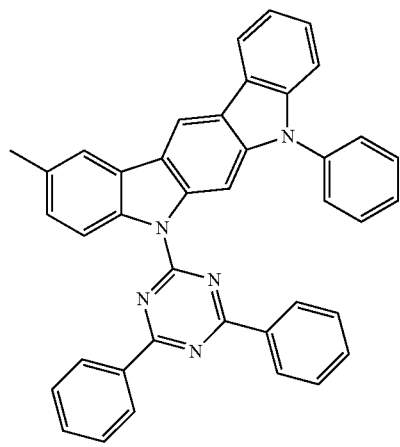
formula (245)
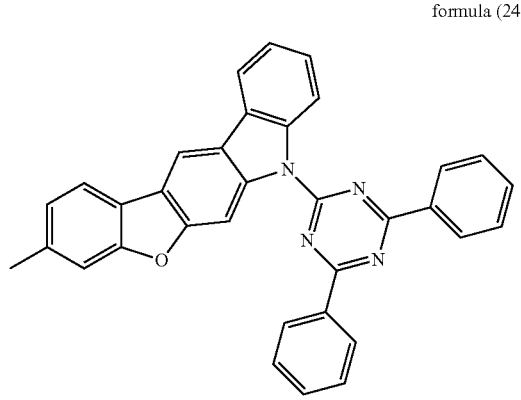
formula (246)
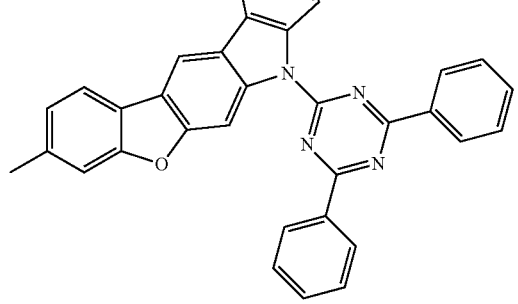
formula (247)
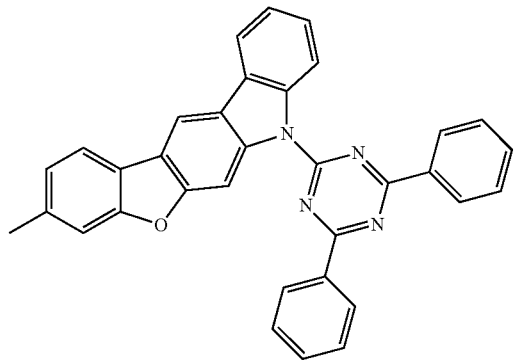
formula (248)
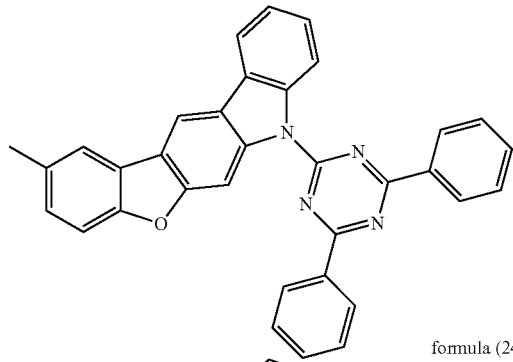
formula (249)
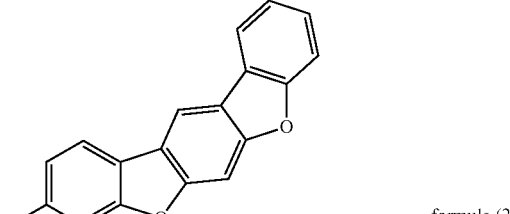
formula (250)
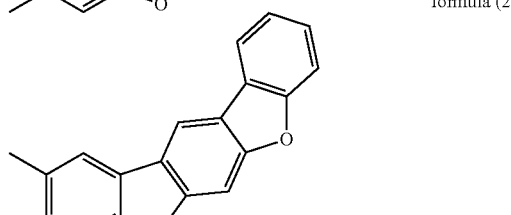
formula (251)
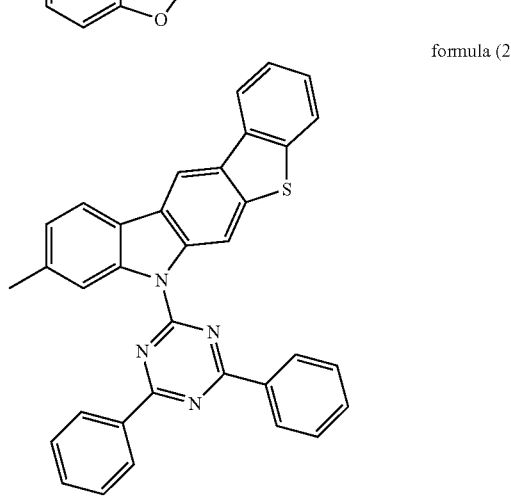

-continued
formula (252)
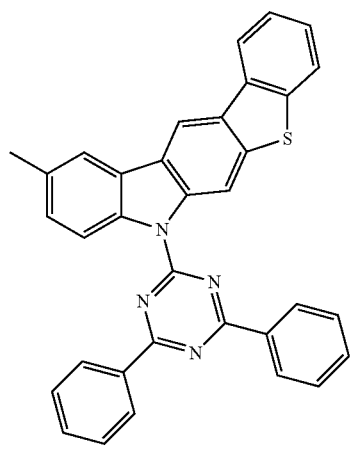
formula (253)
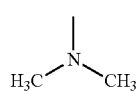
formula (254)
formula (255)
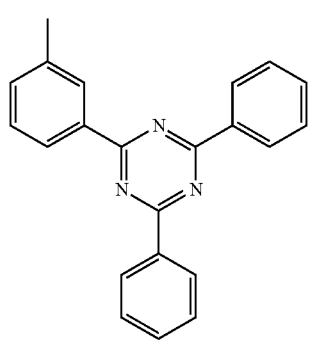
formula (256)
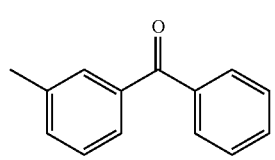
formula (257)
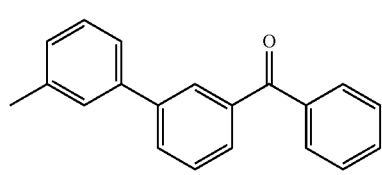
formula (258)
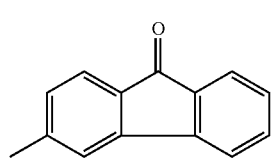
formula (259)
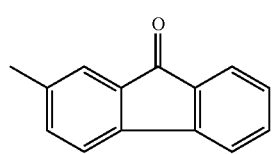
formula (260)
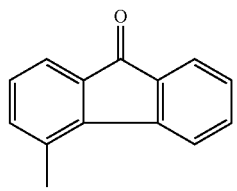
formula (261)
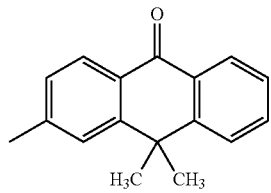
formula (262)
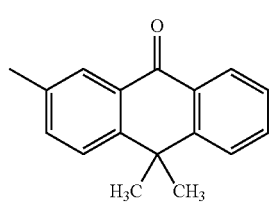
formula (263)
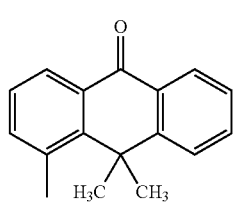
formula (264)
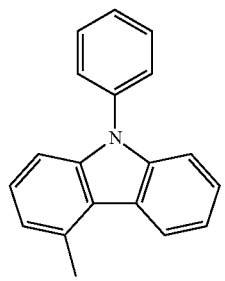
formula (265)
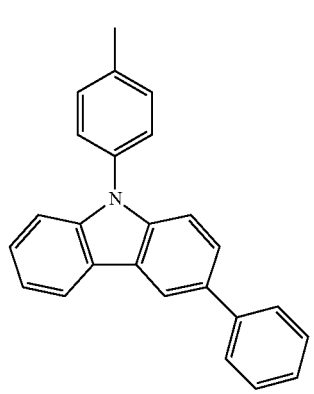

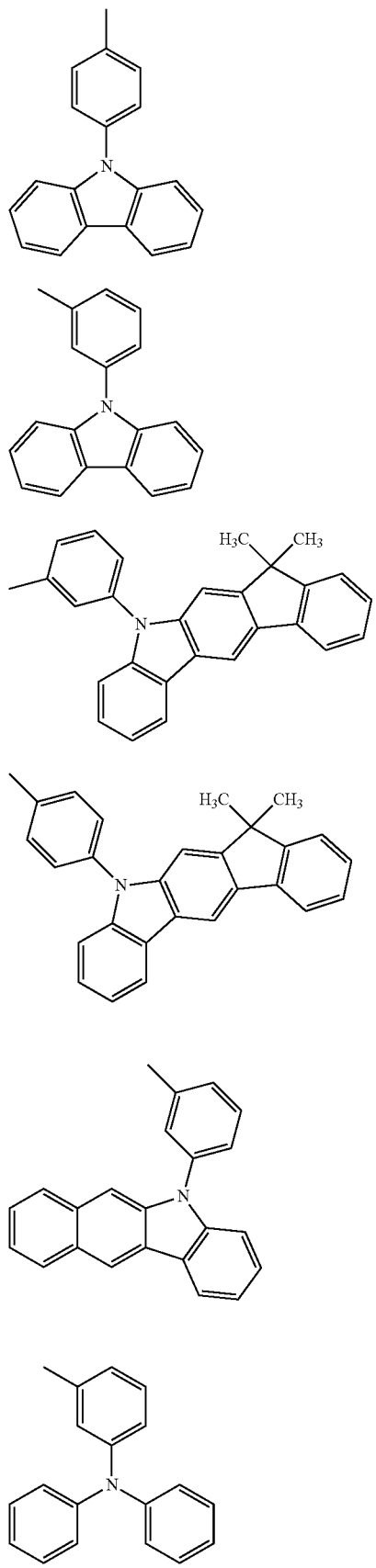
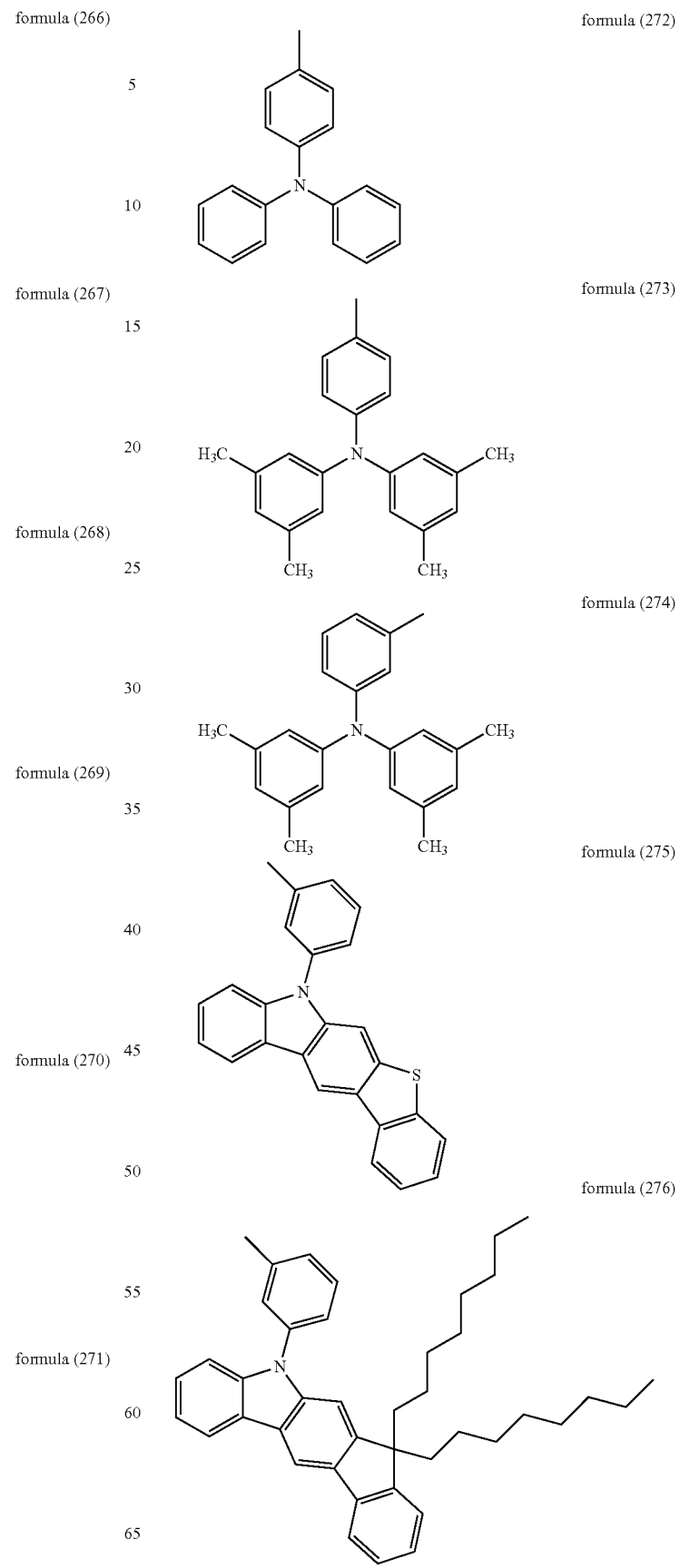

formula (277)

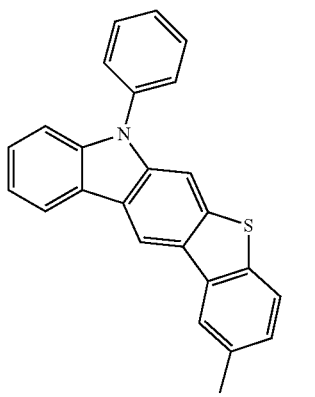

formula (278)

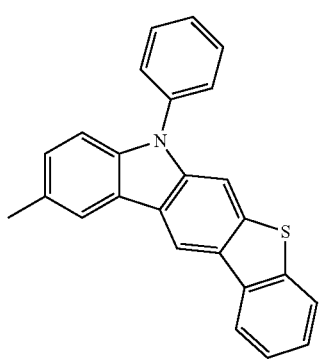

formula (279)

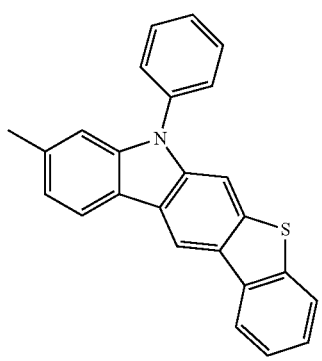

formula (280)

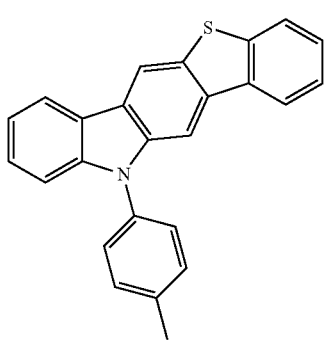

formula (281)

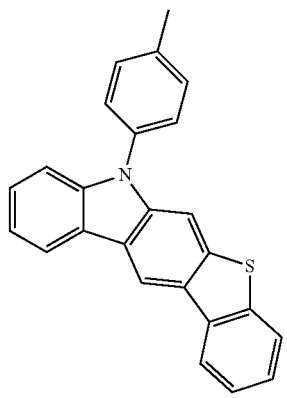

formula (282)

formula (283)

formula (284)

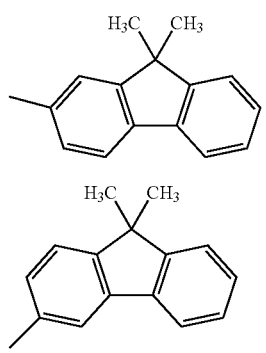

formula (285)

formula (286)

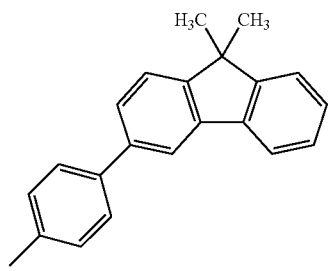

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formula (1) may be electrically charged or uncharged. In a preferred embodiment, the compounds of the formula (1) are electrically neutral. This is achieved in a simple manner in that the charges of the ligands L and L' are selected so that they compensate for the charge of the complexed metal atom M.

Preference is furthermore given to compounds of the formula (1), characterised in that the sum of the valence electrons around the metal atom is 16 for platinum and palladium and 18 for iridium and rhodium. This preference is due to the particular stability of these metal complexes.

In a preferred embodiment of the invention, M stands for iridium or platinum. M particularly preferably stands for iridium.

If M stands for platinum or palladium, the index n stands for 1 or 2. If the index n=1, one bidentate or two monodentate ligands L', preferably one bidentate ligand L', are also coordinated to the metal M. Correspondingly, the index m=1 for one bidentate ligand L' and the index m=2 for two monodentate ligands L'. If the index n=2, the index m=0.

If M stands for iridium or rhodium, the index n stands for 1, 2 or 3, preferably for 2 or 3 and particularly preferably for 3. If the index n=1, four monodentate or two bidentate or one bidentate and two monodentate or one tridentate and one monodentate or one tetradentate ligand L', preferably two bidentate ligands L', are also coordinated to the metal. Correspondingly, the index m is, depending on the ligand L', equal to 1, 2, 3 or 4. If the index n=2, one bidentate or two monodentate ligands L', preferably one bidentate ligand L', are also coordinated to the metal. Correspondingly, the index m is, depending on the ligand L', equal to 1 or 2. If the index n=3, the index m=0.

In a further preferred embodiment of the invention, either all symbols X stand, identically or differently on each occurrence, for $CR^1$ or all symbols X stand for N.

In a further preferred embodiment of the invention, the symbol Q stands, identically or differently on each occurrence, for $R^1C=CR^1$, $R^1C=N$, O or $NR^1$, particularly preferably for $R^1C=CR^1$ and $R^1C=N$ and especially preferably for $R^1C=CR^1$.

It is particularly preferred for the above-mentioned preferences to apply simultaneously.

In a particularly preferred embodiment of the invention, the following applies to the symbols used:
M is iridium or platinum, particularly preferably iridium;
X is on each occurrence $CR^1$ for all positions which are not bonded directly to M;
Q is, identically or differently on each occurrence, $R^1C=CR^1$ or $R^1C=N$, particularly preferably $R^1C=CR^1$;
Where the symbols and indices used have the meanings mentioned above, in particular the preferred meanings mentioned above.

The compounds of the formula (1) according to the invention can be heteroleptic or homoleptic complexes. Preferred embodiments of the present invention are homoleptic complexes where m=0.

In the case of heteroleptic complexes of the formula (1), a bridging unit Z which links the ligand L to one or more further ligands L or L' may also be present on one of the radicals R¹. In a preferred embodiment of the invention, a bridging unit Z is present instead of one of the radicals R¹, meaning that the ligands have a tridentate or polydentate or polypodal character. Two bridging units Z of this type may also be present. This results in the formation of macrocyclic ligands or in the formation of cryptates.

Preferred structures having polydentate ligands are the metal complexes of the following formulae (287) to (298):

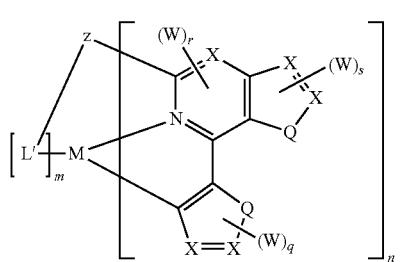

formula (287)

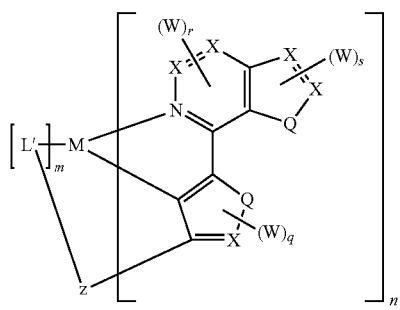

formula (288)

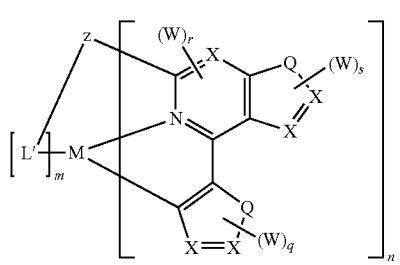

formula (289)

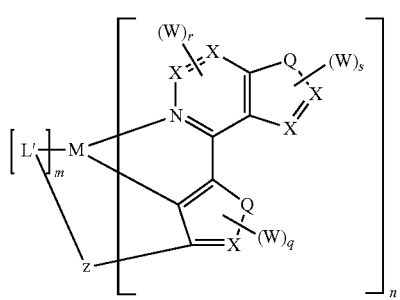

formula (290)

-continued

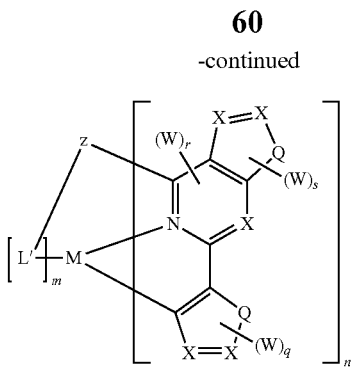

formula (291)

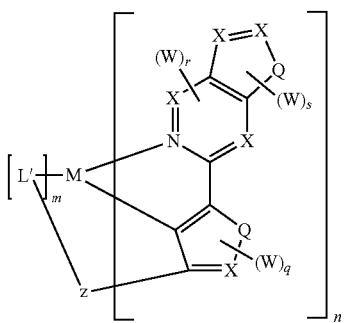

formula (292)

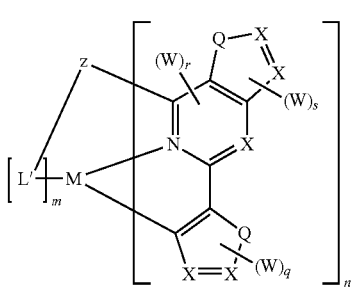

formula (293)

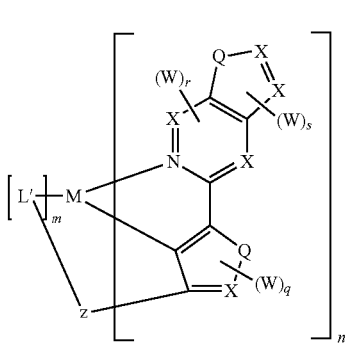

formula (294)

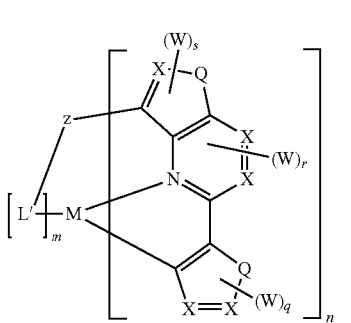

formula (295)

formula (296)

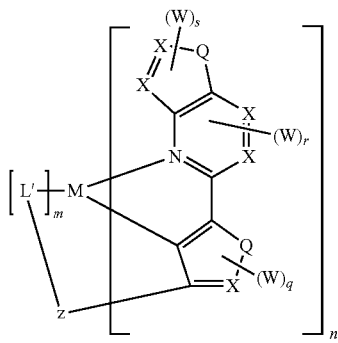

formula (297)

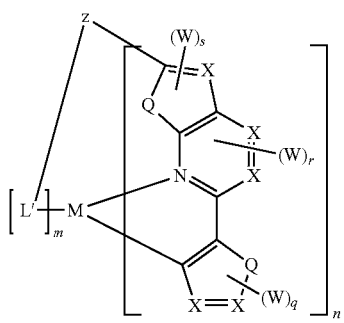

formula (298)

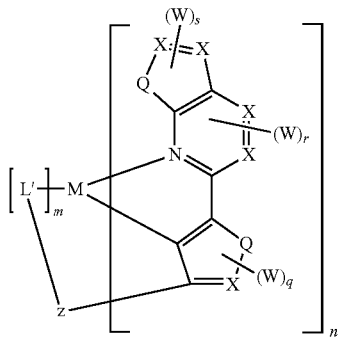

where the symbols used have the meanings mentioned above, and Z preferably represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or L to L'. The bridging unit Z here may also have an asymmetric structure, i.e. the linking of Z to L or L' need not be identical.

The bridging unit Z may be neutral, singly, doubly or triply negatively charged or singly, doubly or triply positively charged. Z is preferably neutral or singly negatively charged or singly positively charged. The charge of Z here is preferably selected so that overall a neutral complex arises.

If Z is a trivalent group, i.e. bridges three ligands L to one another or two ligands L to L' or one ligand L to two ligands L',Z is preferably selected, identically or differently on each occurrence, from the group consisting of B, B(R$^2$)$^-$, B(C(R$^2$)$_2$)$_3$, (R$^2$)B(C(R$^2$)$_2$)$_3$$^-$, B(O)$_3$, (R$^2$)B(O)$_3$$^-$, B(C(R$^2$)$_2$C(R$^2$)$_2$)$_3$, (R$^2$)B(C(R$^2$)$_2$C(R$^2$)$_2$)$_3$$^-$, B(C(R$^2$)$_2$O)$_3$, (R$^2$)B(C(R$^2$)$_2$O)$_3$$^-$, B(OC(R$^2$)$_2$)$_3$, (R$^2$)B(OC(R$^2$)$_2$)$_3$$^-$, C(R$^2$), CO$^-$, CN(R$^2$)$_2$, (R$^2$)C(C(R$^2$)$_2$)$_3$, (R$^2$)C(O)$_3$, (R$^2$)C(C(R$^2$)$_2$C(R$^2$)$_2$)$_3$, (R$^2$)C(C(R$^2$)$_2$O)$_3$, (R$^2$)C(OC(R$^2$)$_2$)$_3$, (R$^2$)C(Si(R$^2$)$_2$)$_3$, (R$^2$)C(Si(R$^2$)$_2$C(R$^2$)$_2$)$_3$, (R$^2$)C(C(R$^2$)$_2$Si(R$^2$)$_2$)$_3$, (R$^2$)C(Si(R$^2$)$_2$Si(R$^2$)$_2$)$_3$, Si(R$^2$), (R$^2$)Si(C(R$^2$)$_2$)$_3$, (R$^2$)Si(O)$_3$, (R$^2$)Si(C(R$^2$)$_2$C(R$^2$)$_2$)$_3$, (R$^2$)Si(OC(R$^2$)$_2$)$_3$, (R$^2$)Si(C(R$^2$)$_2$O)$_3$, (R$^2$)Si(Si(R$^2$)$_2$)$_3$, (R$^2$)Si(Si(R$^2$)$_2$C(R$^2$)$_2$)$_3$, (R$^2$)Si(C(R$^2$)$_2$Si(R$^2$)$_2$)$_3$, (R$^2$)Si(Si(R$^2$)$_2$Si(R$^2$)$_2$)$_3$, N, NO, N(R$^2$)$^+$, N(C(R$^2$)$_2$)$_3$, (R$^2$)N(C(R$^2$)$_2$)$_3$$^+$, N(C=O)$_3$, N(C(R$^2$)$_2$C(R$^2$)$_2$)$_3$, (R$^2$)N(C(R$^2$)$_2$C(R$^2$)$_2$)$_3$$^+$, P, P(R$^2$)$^+$, PO, PS, PSe, PTe, P(O)$_3$, PO(O)$_3$, P(OC(R$^2$)$_2$)$_3$, PO(OC(R$^2$)$_2$)$_3$, P(C(R$^2$)$_2$)$_3$, P(R$^2$)(C(R$^2$)$_2$)$_3$$^+$, PO(C(R$^2$)$_2$)$_3$, P(C(R$^2$)$_2$C(R$^2$)$_2$)$_3$, P(R$^2$)(C(R$^2$)$_2$C(R$^2$)$_2$)$_3$$^+$, PO(C(R$^2$)$_2$C(R$^2$)$_2$)$_3$, S$^+$, S(C(R$^2$)$_2$)$_3$$^+$, S(C(R$^2$)$_2$C(R$^2$)$_2$)$_3$$^+$, or a unit of the formula (299), (300), (301) or (302), formula (299)

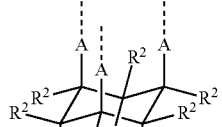

formula (300)

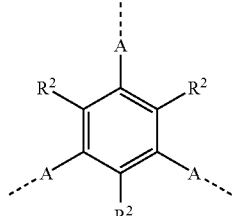

formula (301)

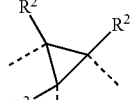

formula (302)

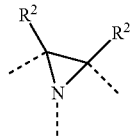

where the dashed bonds in each case indicate the bonding to the part-ligands L or L', and A is selected, identically or differently on each occurrence, from the group consisting of a single bond, O, S, S(=O), S(=O)$_2$, NR$^2$, PR$^2$, P(=O)R$^2$, P(=NR$^2$), C(R$^2$)$_2$, C(=O), C(=NR$^2$), C(=C(R$^2$)$_2$), Si(R$^2$)$_2$ or BR$^2$. The other symbols used have the meanings mentioned above.

If Z is a divalent group, i.e. bridges two ligands L to one another or one ligand L to L', Z is preferably selected, identically or differently on each occurrence, from the group consisting of BR$^2$, B(R$^2$)$_2$$^-$, C(R$^2$)$_2$, C(=O), Si(R$^2$)$_2$, NR$^2$, PR$^2$, P(R$^2$)$_2$$^+$, P(=O)(R$^2$), P(=S)(R$^2$), AsR$^2$, As(=O)(R$^2$), As(=S)(R$^2$), O, S, Se, or a unit of the formulae (303) to (311), formula (303)

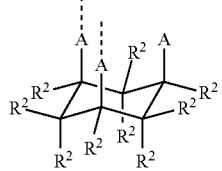

-continued

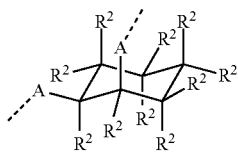

formula (304)

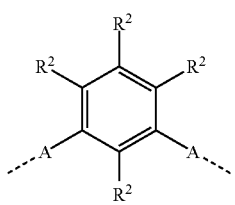

formula (305)

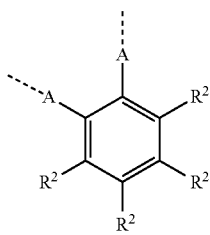

formula (306)

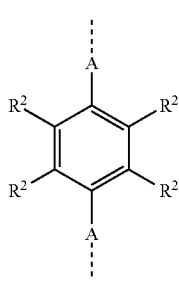

formula (307)

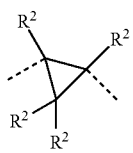

formula (308)

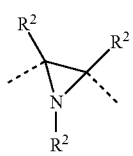

formula (309)

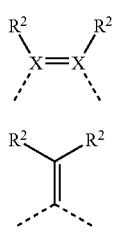

formula (310)

formula (311)

where the dashed bonds in each case indicate the bonding to the part-ligands L or L', and the further symbols used in each case have the meanings mentioned above.

Preferred ligands L' as occur in formula (1) are described below. Correspondingly, the ligand groups L' can also be selected if they are bonded to L via a bridging unit Z.

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' may also be bonded to L via a bridging group Z.

Preferred neutral, monodentate ligands L' are selected from carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides $F^-$, $Cl^-$, $Br^-$ and $I^-$, alkylacetylides, such as, for example, methyl-$C{\equiv}C^-$, tert-butyl-$C{\equiv}C^-$, arylacetylides, such as, for example, phenyl-$C{\equiv}C^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-butanethiolate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or $N^{3-}$. Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino)ethyl]-pyridine, 2-[1-(ethylimino)ethyl]pyridine, 2-[1-(isopropylimino)ethyl]pyridine, 2-[1-(tert-butylimino)ethyl]pyridine, diimines, such as, for example, 1,2-bis(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino)

ethane, 1,2-bis(2,6-diisopropylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis-diphenylphosphinomethane, bisdiphenylphosphinoethane, bis(diphenylphosphino)propane, bis(diphenylphosphino)butane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl) borate and tetrakis(1-pyrazolyl)borate.

Particular preference is furthermore given to bidentate, monoanionic ligands L' which form, with the metal, a cyclometallated five-membered or six-membered ring having at least one metal-carbon bond, in particular a cyclometallated five-membered ring. These are, in particular, ligands as generally used in the area of phosphorescent metal complexes for organic electroluminescent devices, i.e. ligands of the phenylpyridine, naphthylpyridine, phenylquinoline, phenylisoquinoline, etc., type, each of which may be substituted by one or more radicals $R^1$ to $R^7$. A multiplicity of ligands of this type is known to the person skilled in the art in the area of phosphorescent electroluminescent devices, and he will be able to select further ligands of this type, without inventive step, as ligand L' for compounds of the formula (1). In general, the combination of two groups, as represented by the following formulae (312) to (339), is particularly suitable for this purpose, where one group is bonded via a neutral nitrogen atom or a carbene atom and the other group is bonded via a negatively charged carbon atom or a negatively charged nitrogen atom. The ligand L' can then be formed from the groups of the formulae (312) to (339) by these groups bonding to one another, in each case at the position denoted by #. The position at which the groups coordinate to the metal is denoted by *. These groups may also be bonded to the ligand L via one or two bridging units Z.

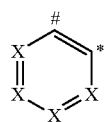

formula (312)

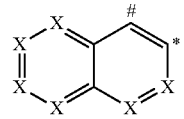

formula (313)

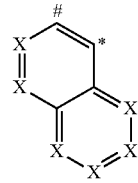

formula (314)

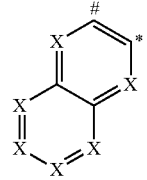

formula (315)

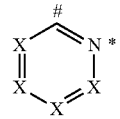

formula (316)

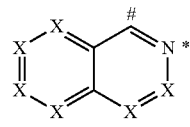

formula (317)

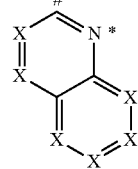

formula (318)

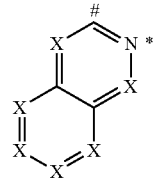

formula (319)

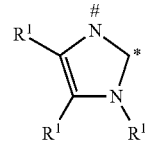

formula (320)

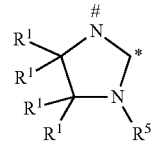

formula (321)

formula (322)

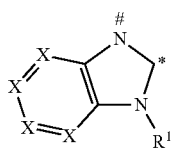

formula (323)

formula (324)

formula (325)

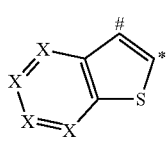

formula (326)

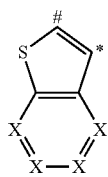

formula (327)

formula (328)

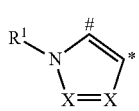

formula (329)

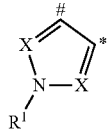

formula (330)

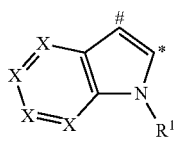

formula (331)

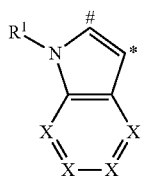

formula (332)

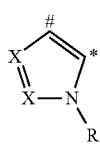

formula (333)

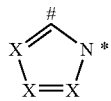

formula (334)

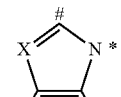

formula (335)

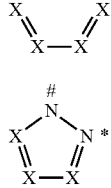

formula (336)

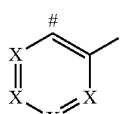

formula (337)

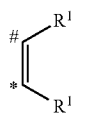

formula (338)

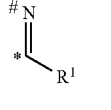

formula (339)

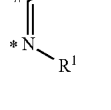

The symbols used here have the same meaning as described above, and preferably a maximum of three symbols X in each group stand for N, particularly preferably a maximum of two symbols X in each group stand for N, very particularly preferably a maximum of one symbol X in each group stands for N. Especially preferably, all symbols X stand, identically or differently on each occurrence, for $CR^1$.

In a particularly preferred embodiment of the present invention, two fragments of a ligand L' of the formulae (312) to (339) are combined with one another via position # in such a way that at least one of the fragments contains a heteroatom at position *.

In a very particularly preferred embodiment of the present invention, the ligand L' is composed of precisely one fragment with no heteroatom from the list of the formulae (312) to (339) and precisely one fragment with a heteroatom, preferably a nitrogen atom, from the list of the fragments having the formulae (312) to (339).

Likewise preferred ligands L' are $\eta^5$-cyclopentadienyl, $\eta^5$-pentamethylcyclopentadienyl, $\eta^6$-benzene and $\eta^7$-cycloheptatrienyl, each of which may be substituted by one or more radicals $R^1$.

Likewise preferred ligands L' are 1,3,5-cis-cyclohexane derivatives, in particular of the formula (340), 1,1,1-tri(methylene)methane derivatives, in particular of the formula (341), and 1,1,1-trisubstituted methanes, in particular of the formulae (342) and (343),

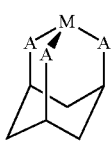
formula (340)

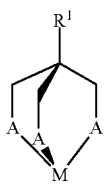
formula (341)

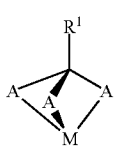
formula (342)

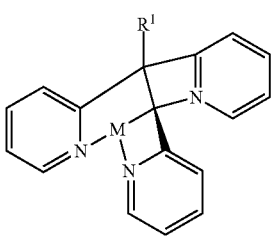
formula (343)

where, in each of the formulae, the coordination to the metal M is depicted, $R^1$ has the meaning mentioned above, and A stands, identically or differently on each occurrence, for $O^-$, $S^-$, $COO^-$, $P(R^1)_2$ or $N(R^1)_2$.

Preferred radicals $R^1$ in the structures mentioned above are selected on each occurrence, identically or differently, from the group consisting of H, D, F, Br, $N(R^2)_2$, CN, $B(OR^2)_2$, $C(=O)R^2$, $P(=O)(R^2)_2$, a straight-chain alkyl group having 1 to 10 C atoms or a straight-chain alkenyl or alkynyl group having 2 to 10 C atoms or a branched or cyclic alkyl, alkenyl or alkynyl group having 3 to 10 C atoms, each of which may be substituted by one or more radicals $R^2$, where one or more H atoms may be replaced by F, or an aromatic or heteroaromatic ring system having 5 to 14 aromatic ring atoms, which may in each case be substituted by one or more radicals $R^2$; a plurality of radicals R" here may also form a mono- or polycyclic, aliphatic, aromatic and/or benzo-fused ring system with one another. Particularly preferred radicals $R^1$ are selected on each occurrence, identically or differently, from the group consisting of H, F, Br, CN, $B(OR^2)_2$, a straight-chain alkyl group having 1 to 6 C atoms, in particular methyl, or a branched or cyclic alkyl group having 3 to 10 C atoms, in particular isopropyl or tert-butyl, where one or more H atoms may be replaced by F, or an aromatic or heteroaromatic ring system having 5 to 12 aromatic ring atoms, which may in each case be substituted by one or more radicals $R^2$; a plurality of radicals $R^1$ here may also form a mono- or polycyclic, aliphatic, aromatic and/or benzo-fused ring system with one another.

The metal complexes according to the invention can in principle be prepared by various processes. However, the processes described below have proven particularly suitable.

The present invention therefore furthermore relates to a process for the preparation of the metal-complex compounds of the formula (1) by reaction of the corresponding free ligands with metal alkoxides of the formula (344), with metal ketoketonates of the formula (345) or with metal halides of the formula (346), $M(OR^1)_n$
formula (344)

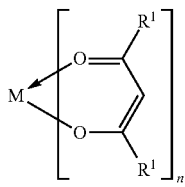
formula (345)

$MHal_n$
formula (346)

where the symbols M, n and $R^1$ have the meanings indicated above, and Hal=F, Cl, Br or I.

It is likewise possible to use metal compounds, in particular iridium compounds, which carry both alcoholate and/or halide and/or hydroxyl radicals as well as ketoketonate radicals. These compounds may also be charged.

Corresponding iridium compounds which are particularly suitable as starting materials are disclosed in WO 2004/085449. $[IrCl_2(acac)_2]^-$, for example $Na[IrCl_2(acac)_2]$, is particularly suitable.

The complexes are preferably synthesised as described in WO 2002/060910 and in WO 2004/085449. heteroleptic complexes can also be synthesised, for example, in accordance with WO 2005/042548. The synthesis can also be activated, for example, thermally, photochemically and/or by microwave radiation.

These processes enable the compounds of the formula (1) according to the invention to be obtained in high purity, preferably greater than 99% (determined by means of $^1$H-NMR and/or HPLC).

The synthetic methods explained here enable the preparation of, inter alia, the compounds of the formulae (347) to (496) according to the invention depicted below.

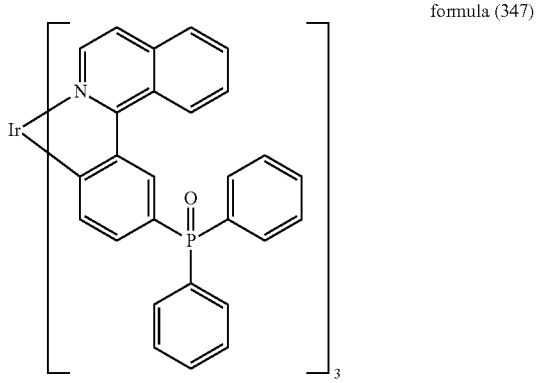
formula (347)

formula (348)
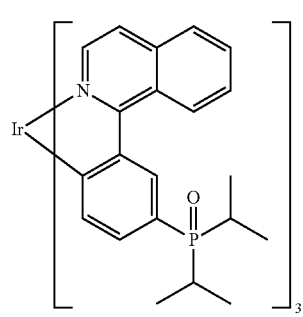
formula (349)
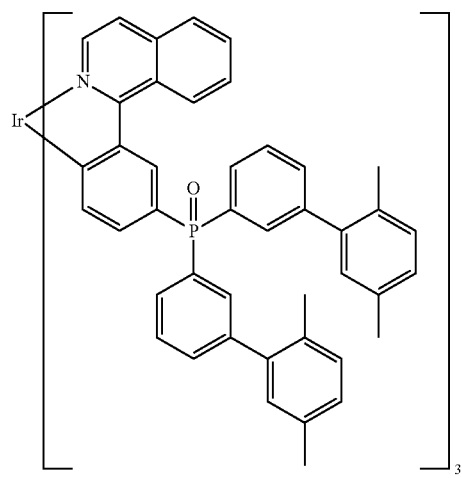
formula (350)
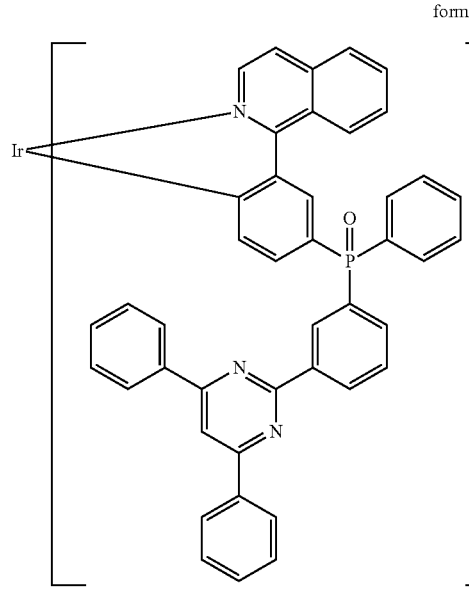
formula (351)
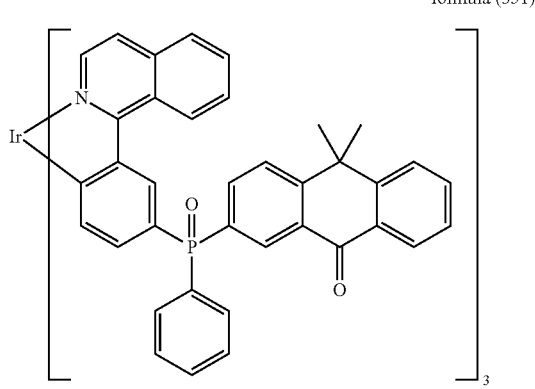
formula (352)
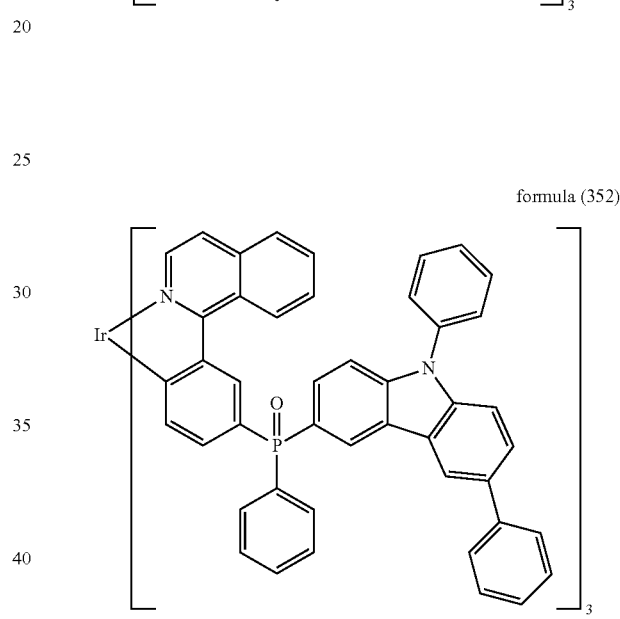
formula (353)
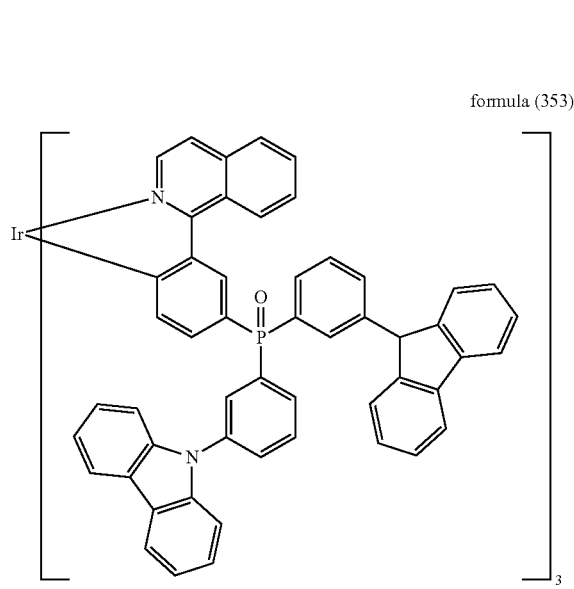

formula (354)
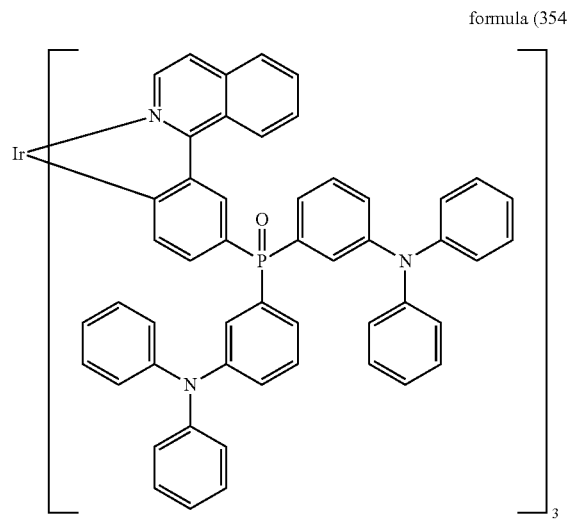
formula (354)
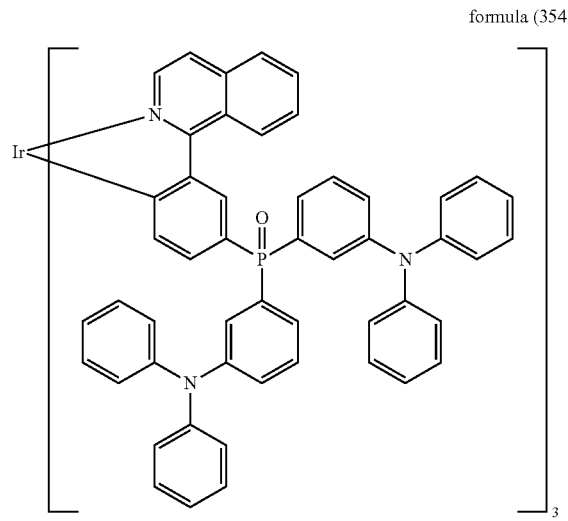
formula (355)
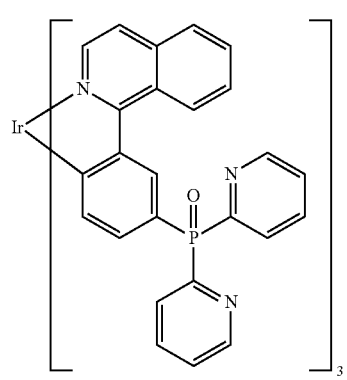
formula (356)
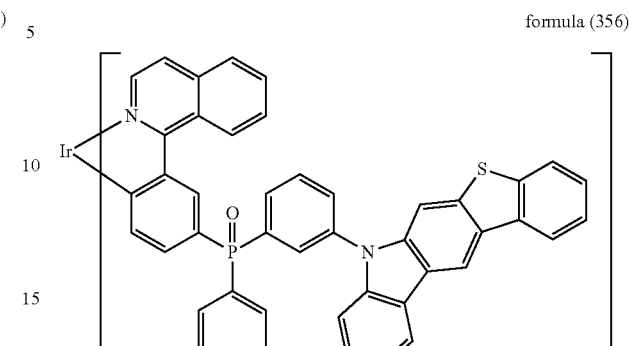
formula (357)
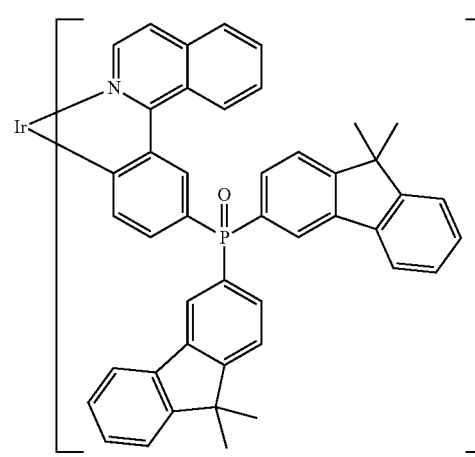
formula (358)
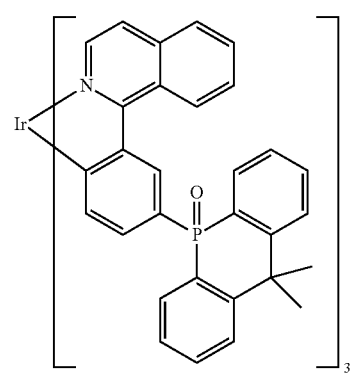
formula (359)
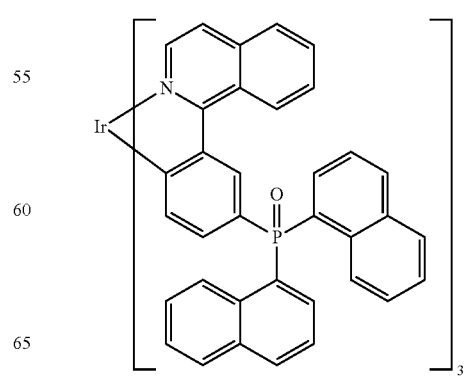

formula (360)
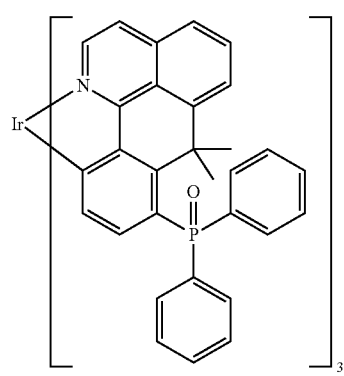
formula (361)
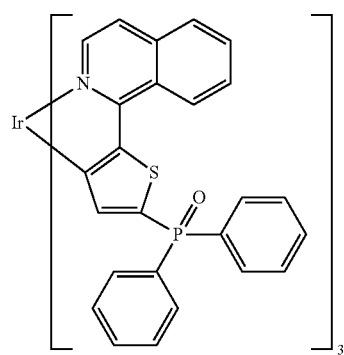
formula (362)
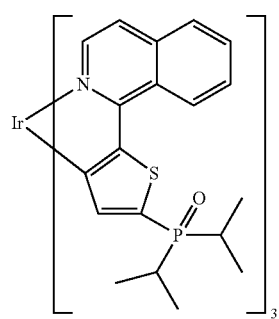
formula (363)
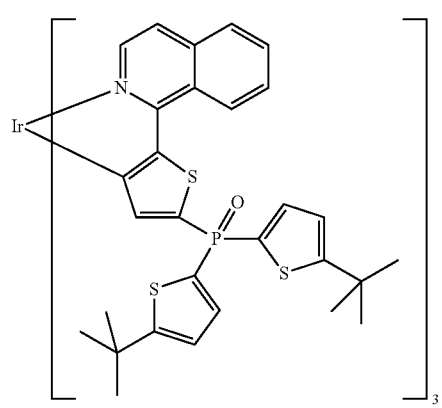
formula (364)
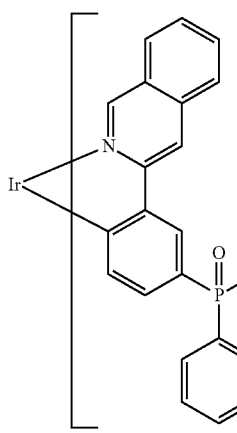
formula (365)
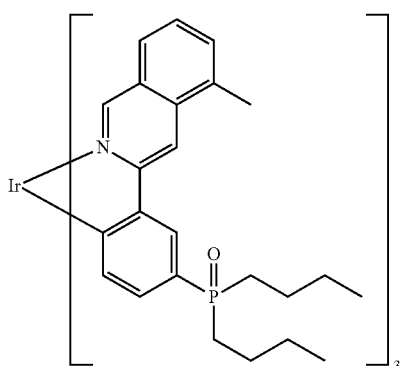
formula (366)
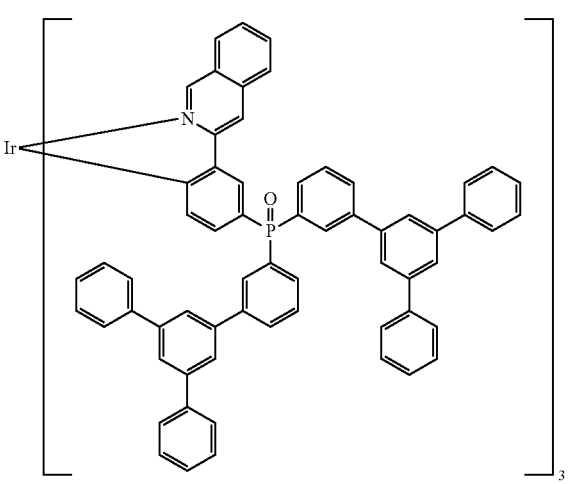

formula (367)
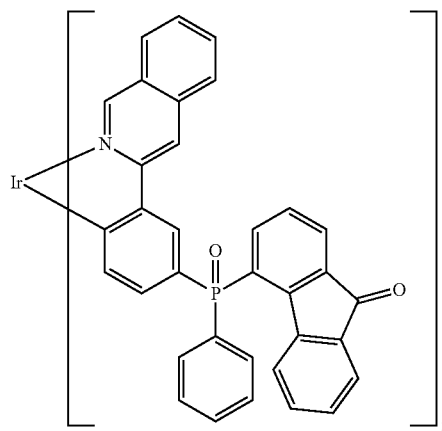
formula (368)
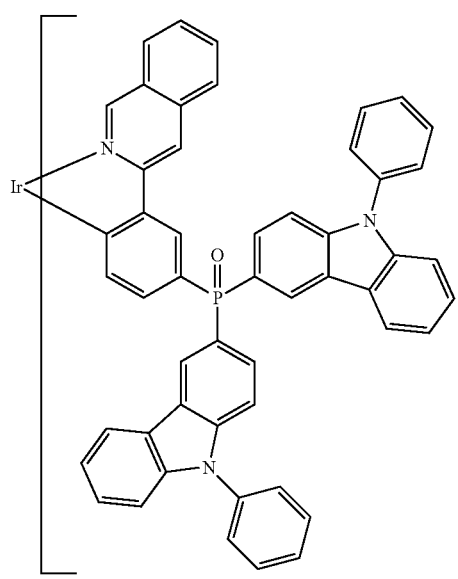
formula (369)
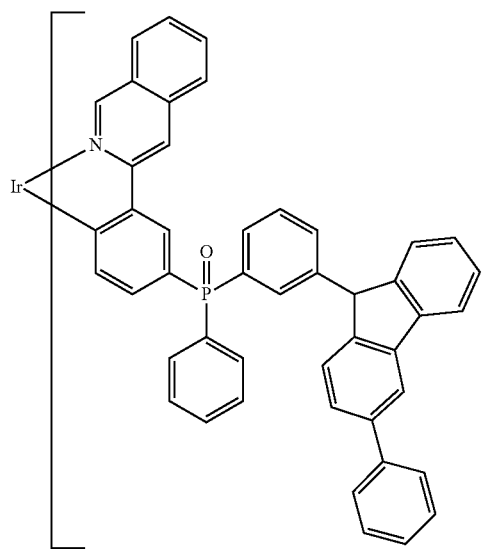
formula (370)
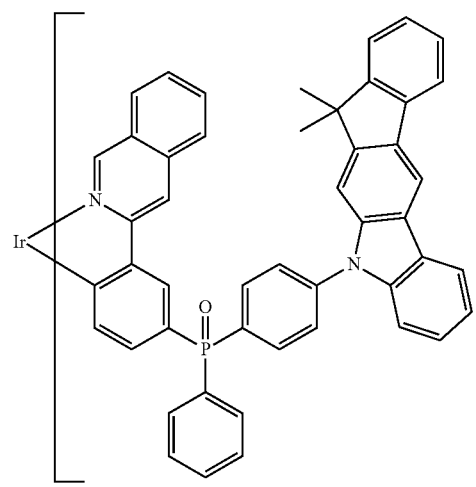
formula (371)
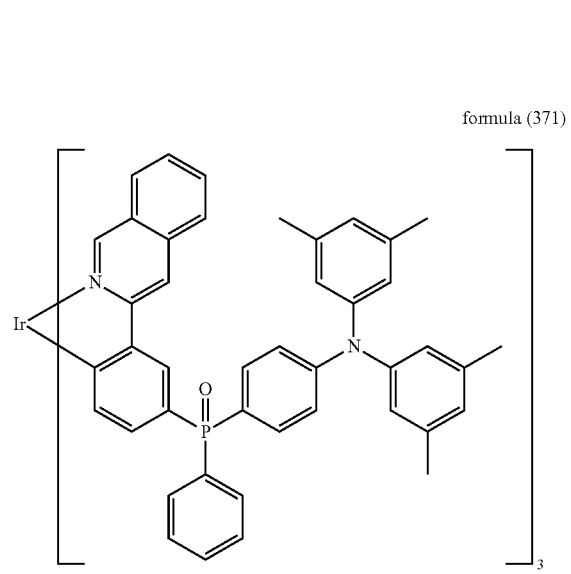
formula (372)
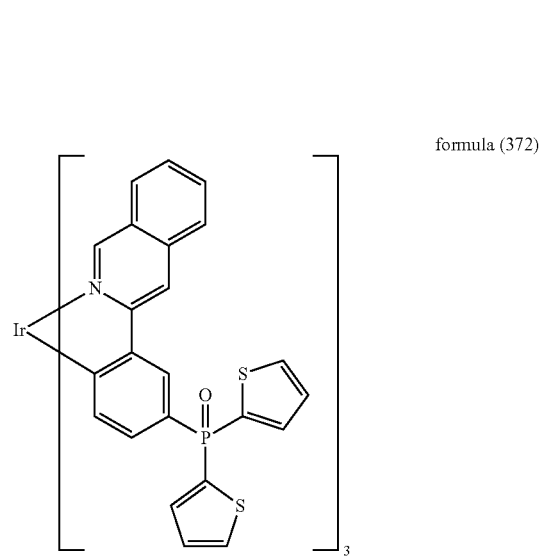

formula (373)
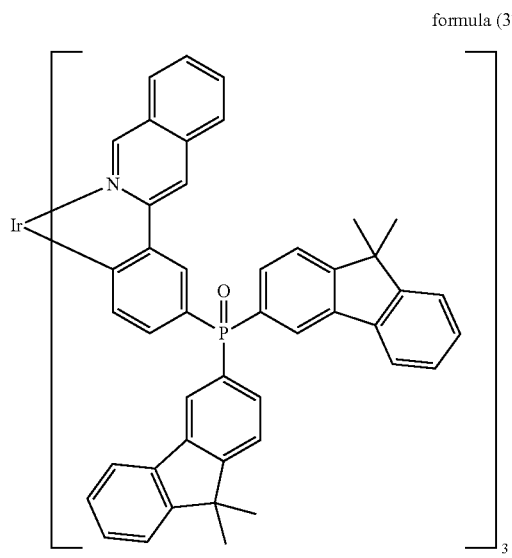
formula (376)
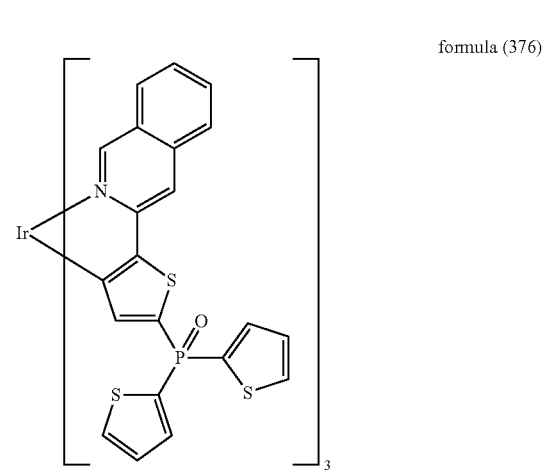
formula (374)
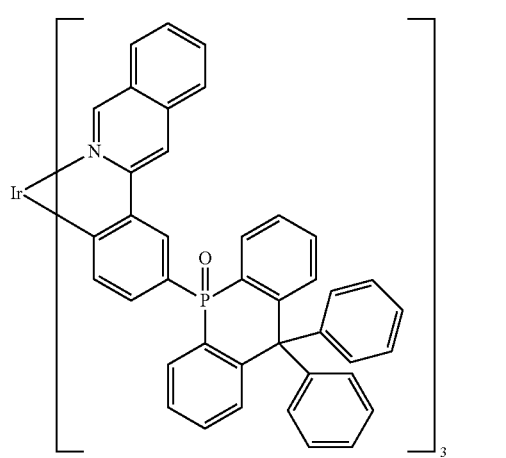
formula (377)
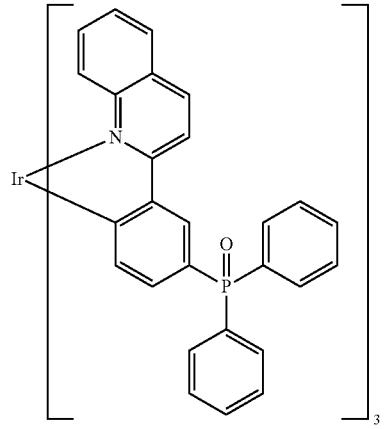
formula (375)
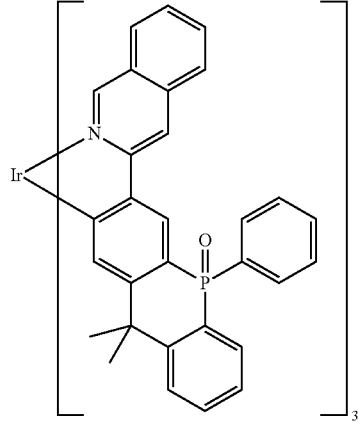
formula (378)
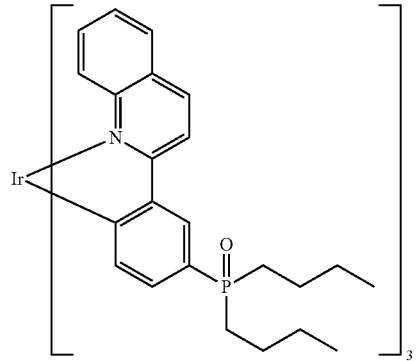

formula (379)
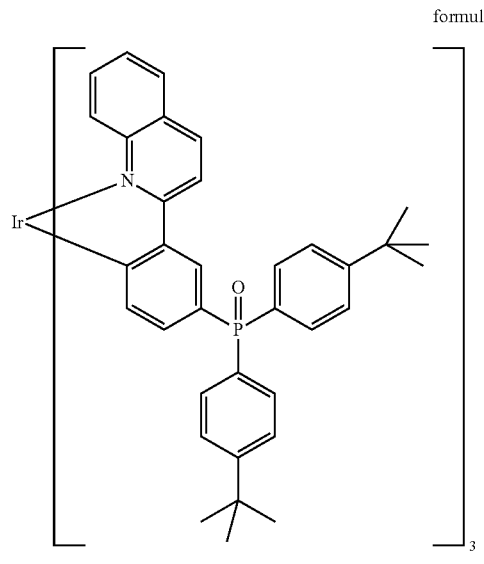
formula (380)
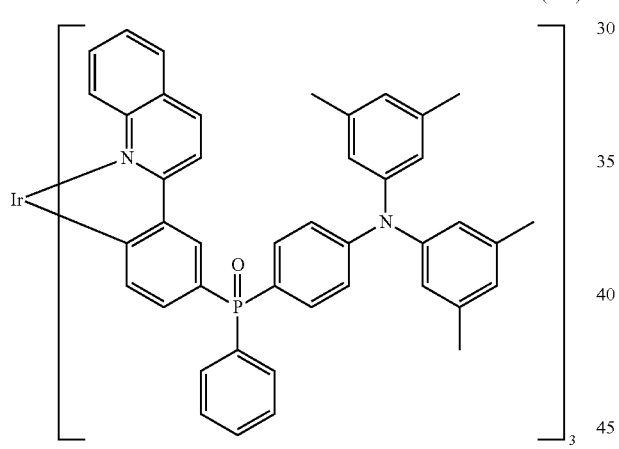
formula (381)
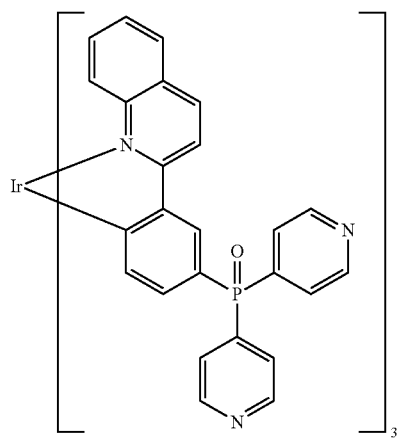
formula (382)
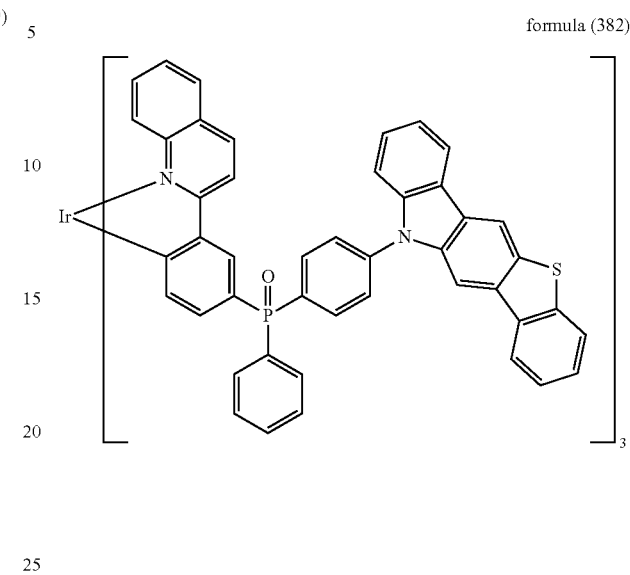
formula (383)
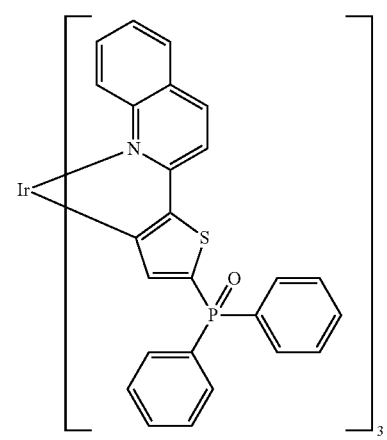
formula (384)
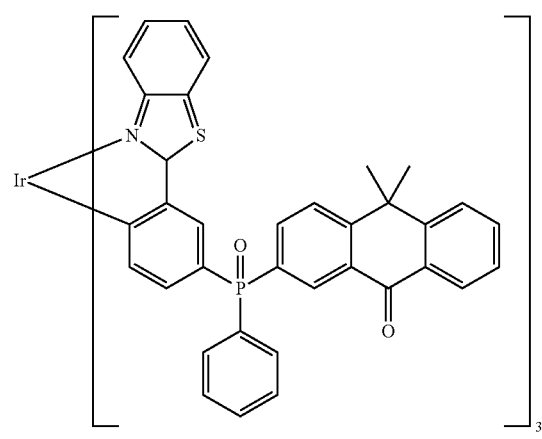

formula (385)
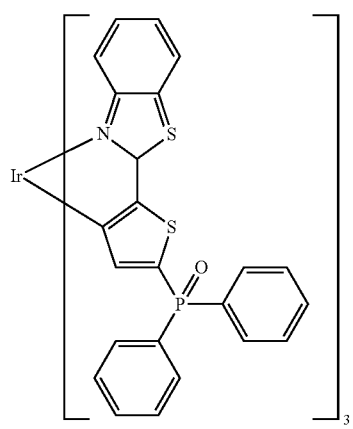
formula (386)
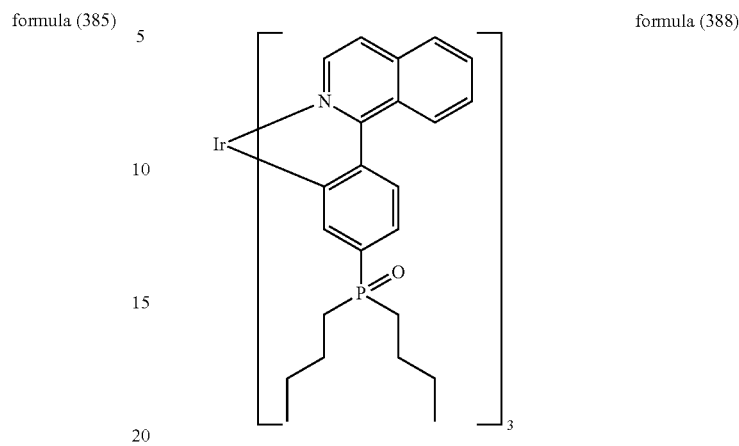
formula (387)
formula (388)
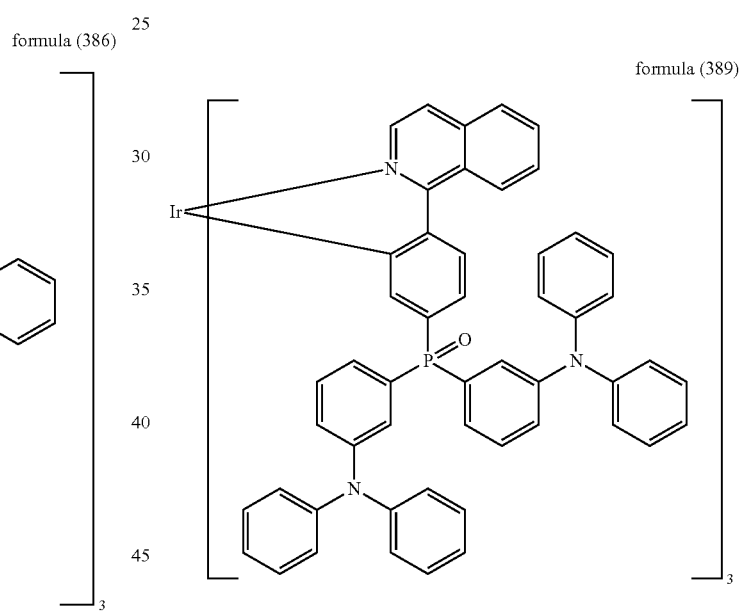
formula (389)
formula (390)
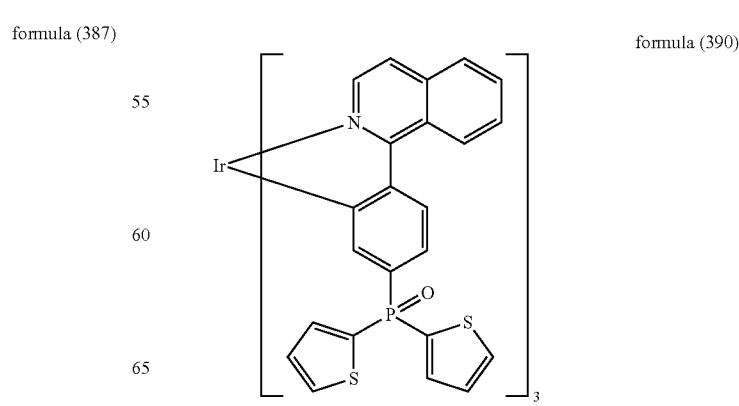

formula (391)
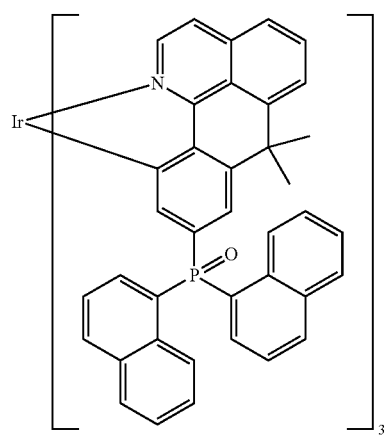
formula (392)
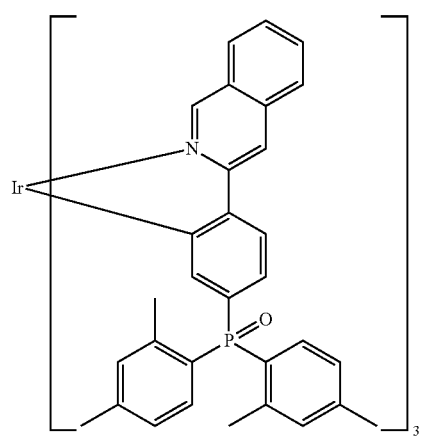
formula (393)
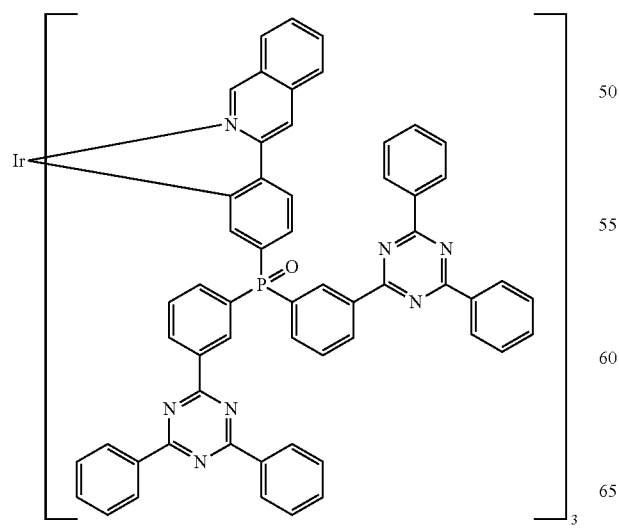
formula (394)
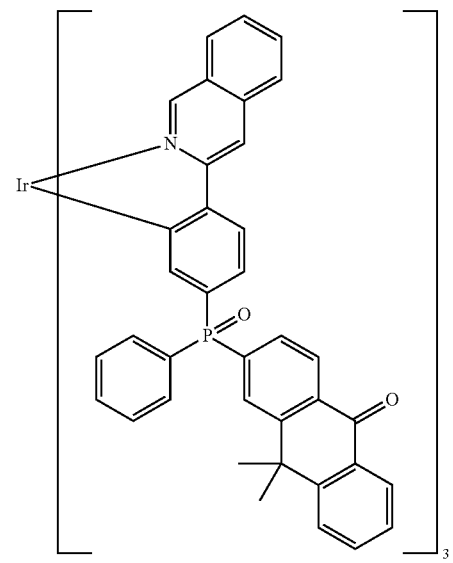
formula (395)
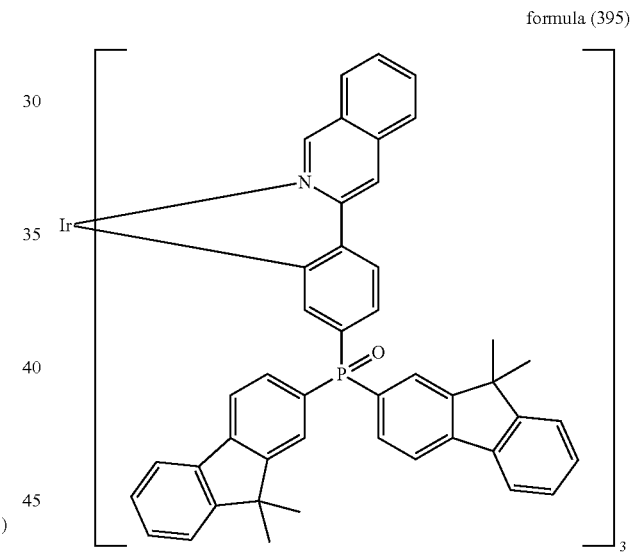
formula (396)
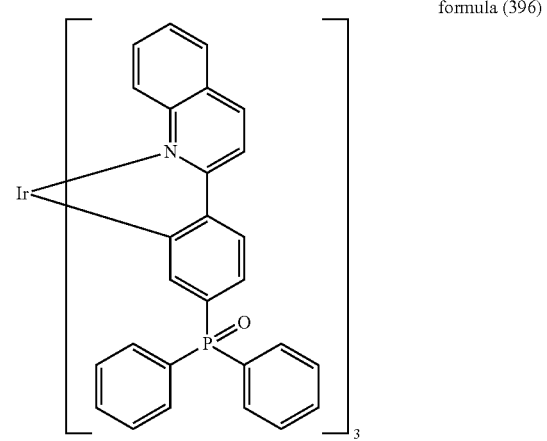

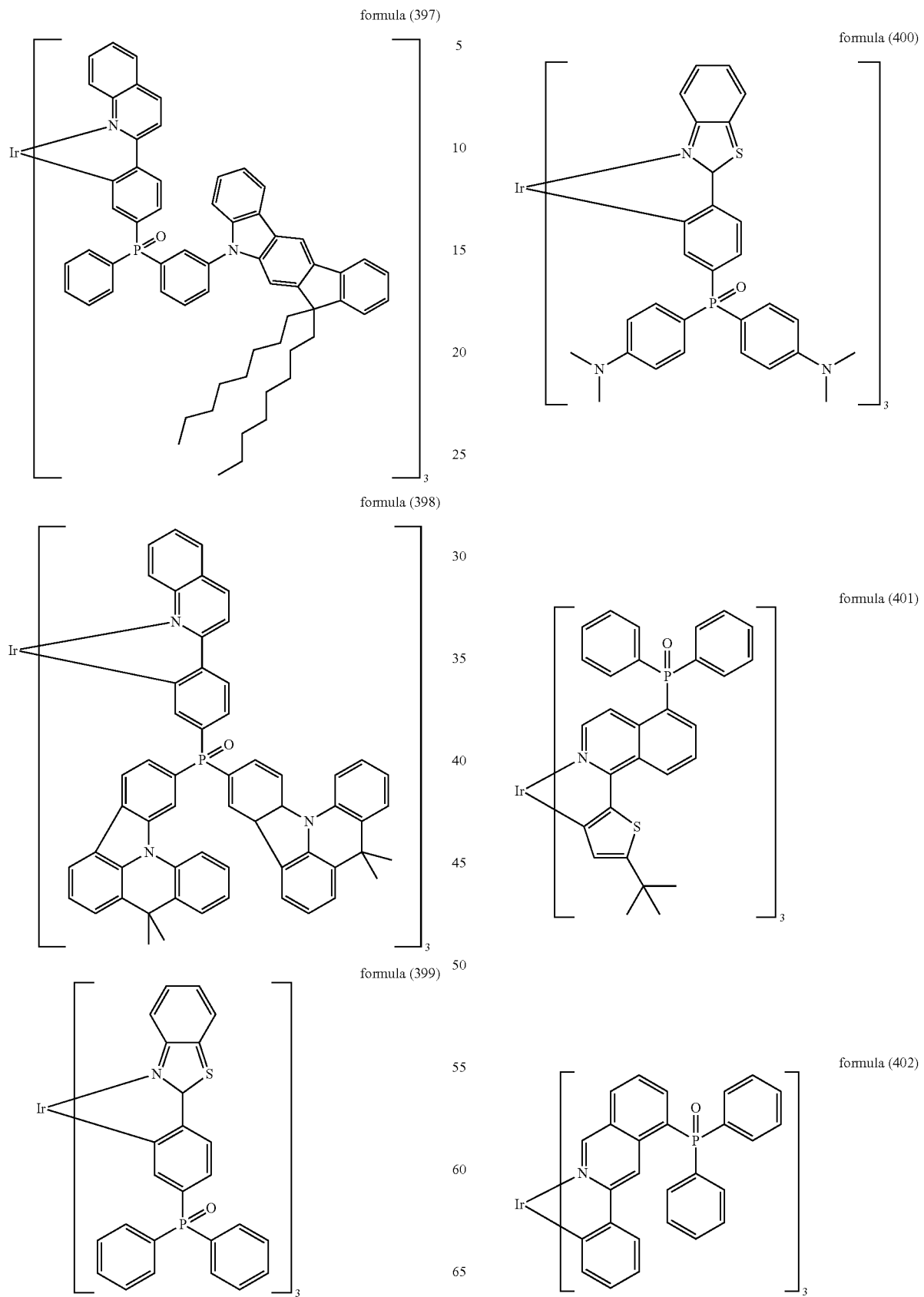

formula (403)
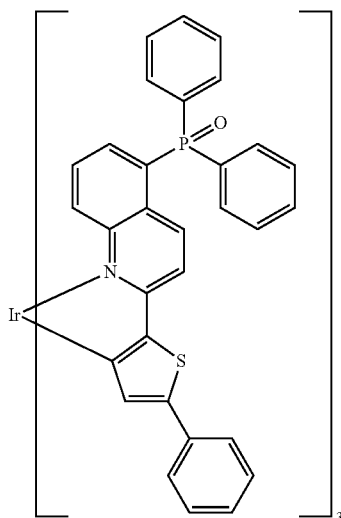
formula (404)
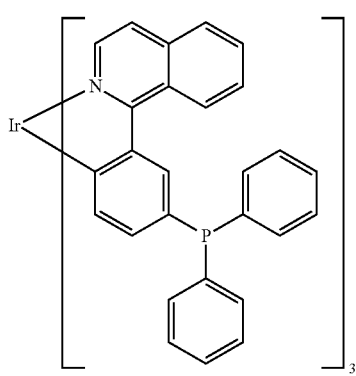
formula (405)
formula (406)
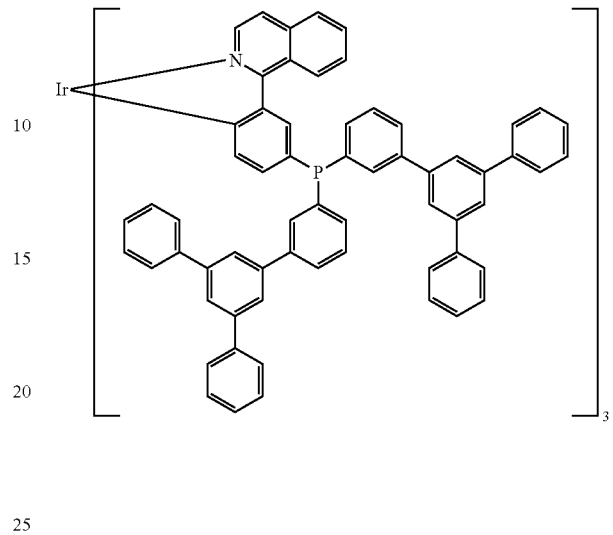
formula (407)
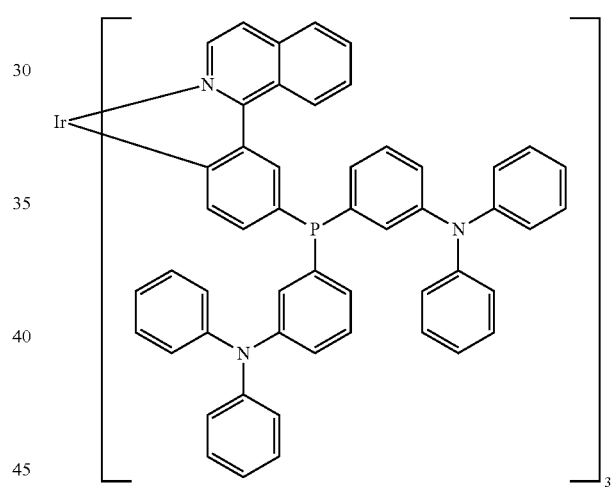
formula (408)
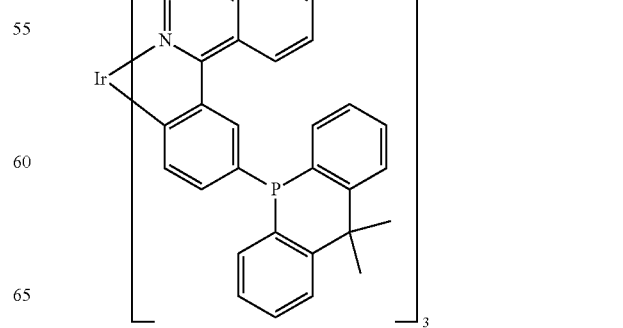

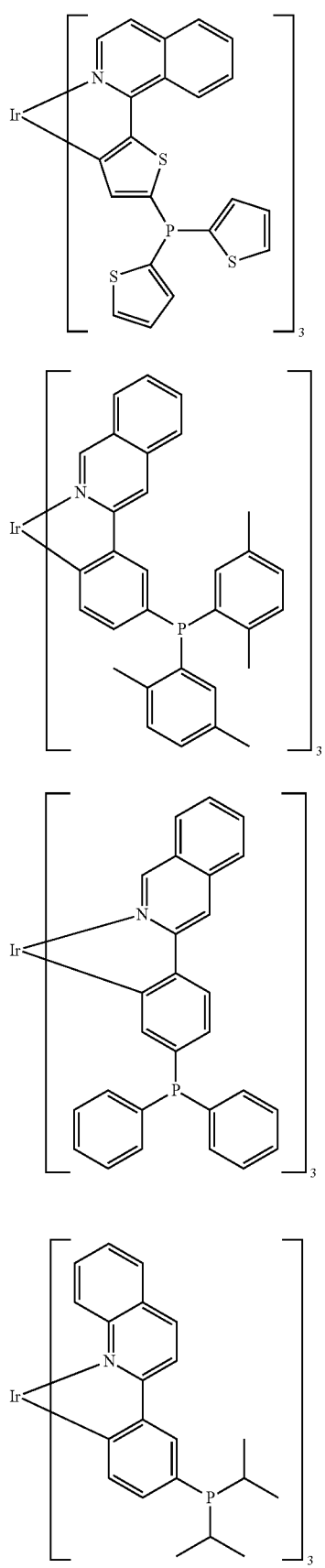
formula (409)
formula (410)
formula (411)
formula (412)
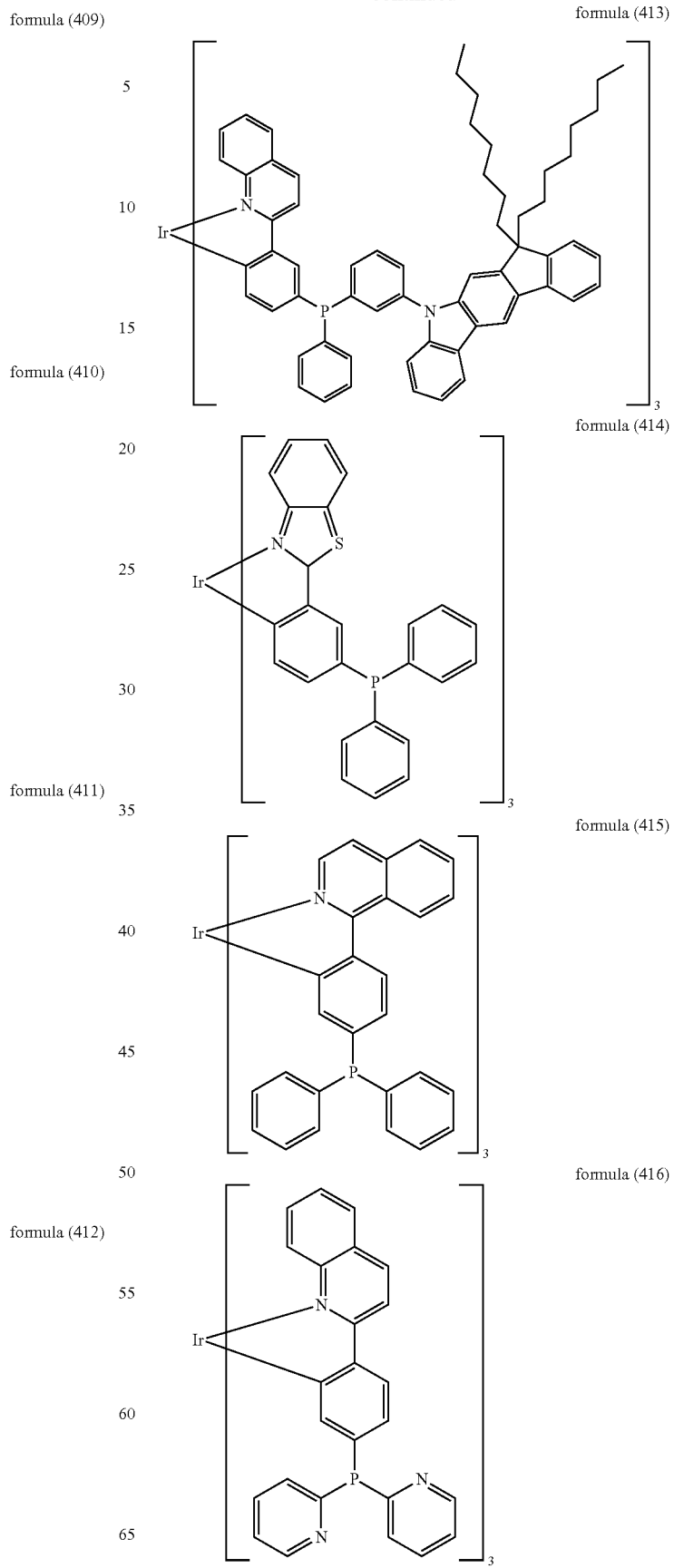
formula (413)
formula (414)
formula (415)
formula (416)

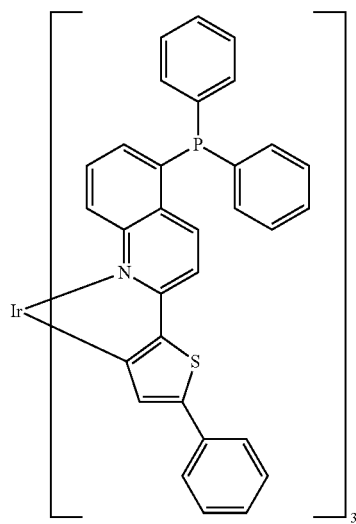
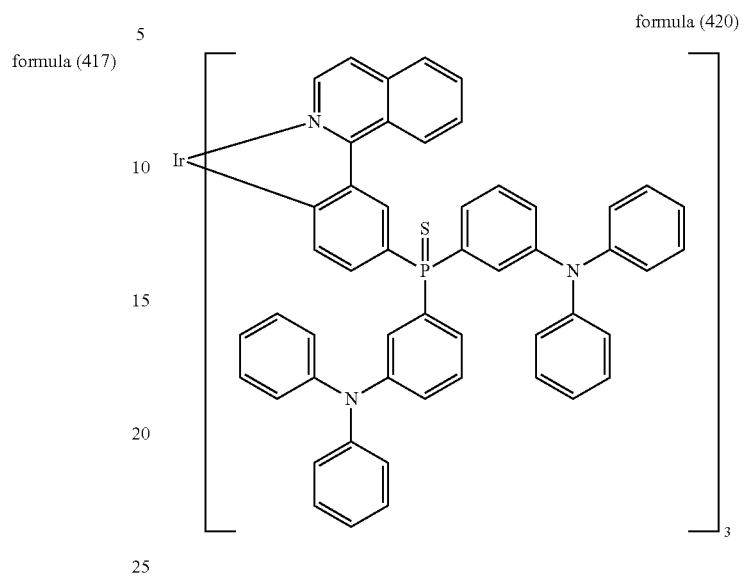
formula (417)
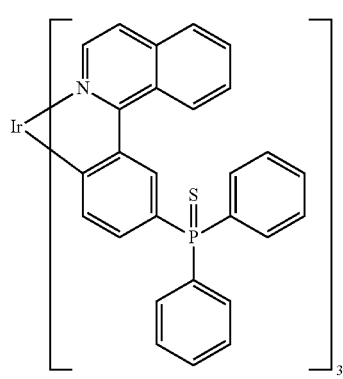
formula (418)
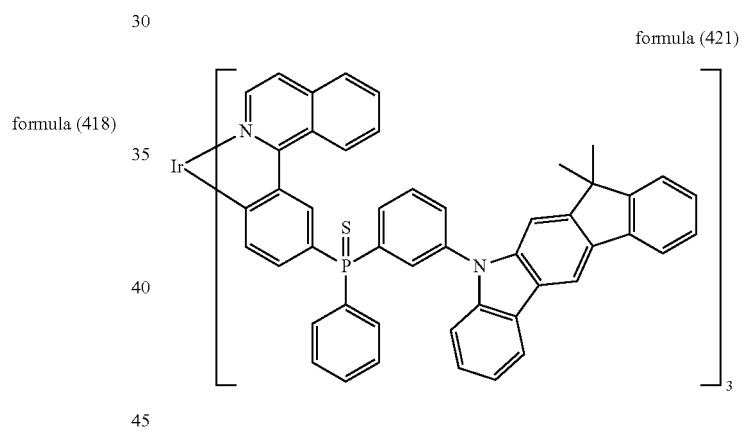
formula (420)
formula (421)
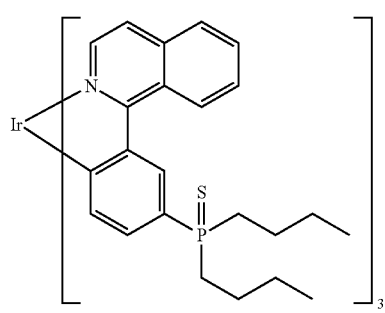
formula (419)
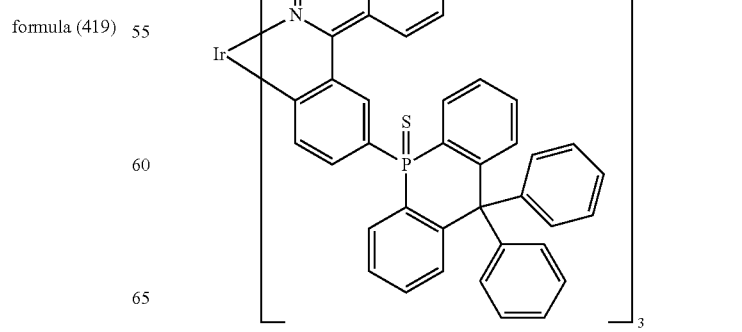
formula (422)

formula (423)
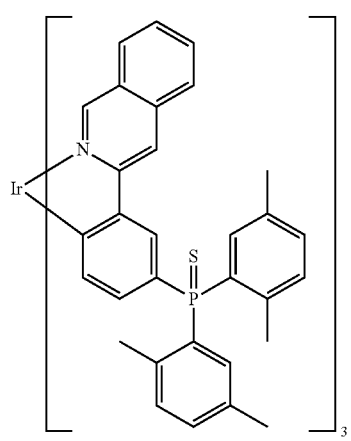
formula (424)
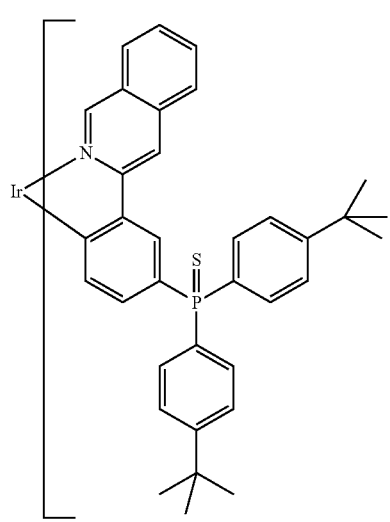
formula (425)
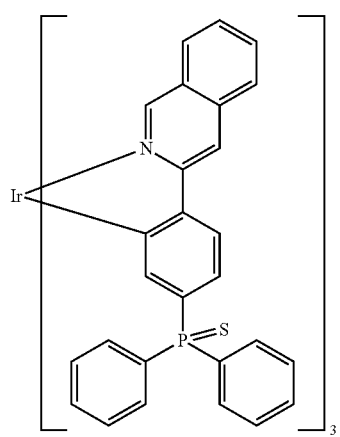
formula (426)
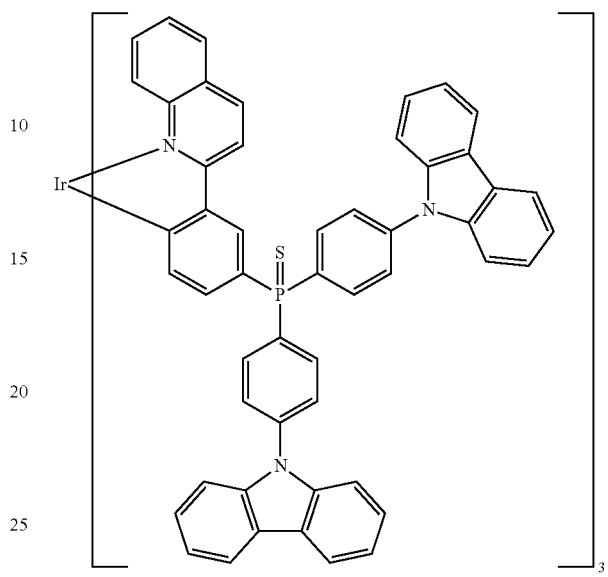
formula (427)
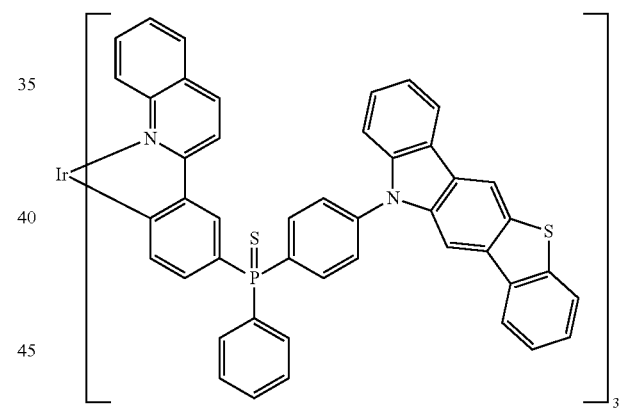
formula (428)
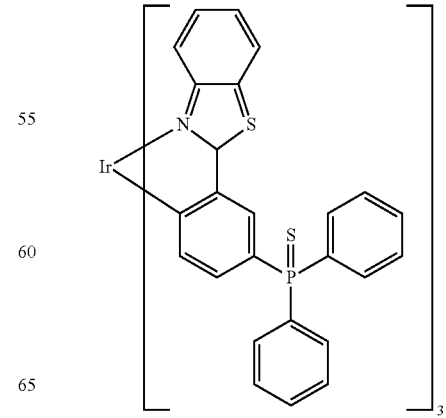

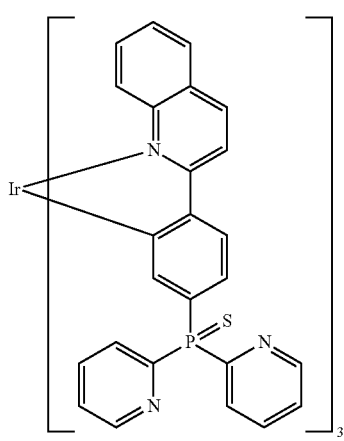
formula (429)
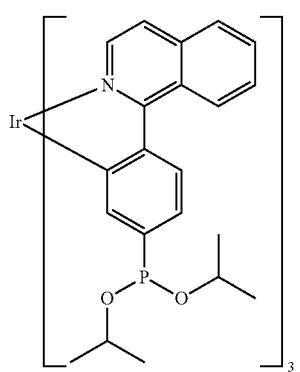
formula (432)
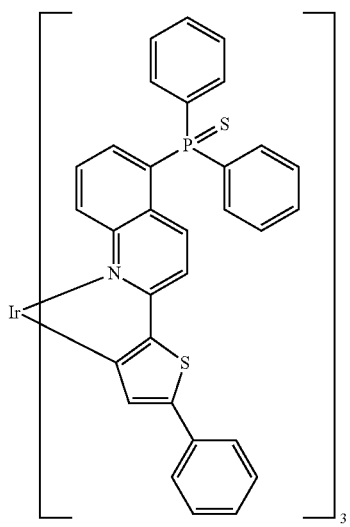
formula (430)
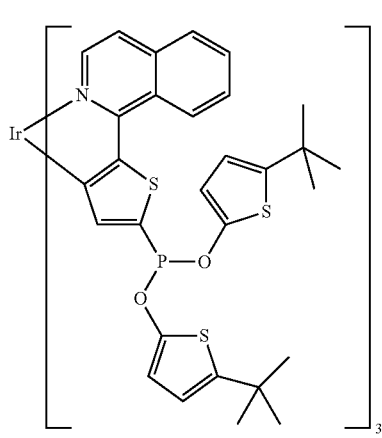
formula (433)
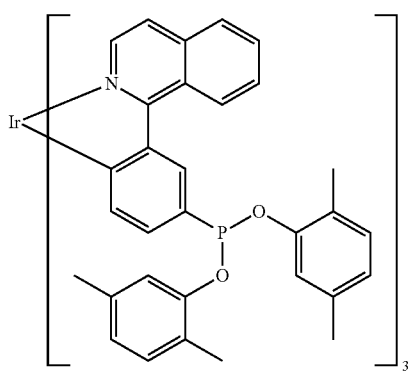
formula (431)
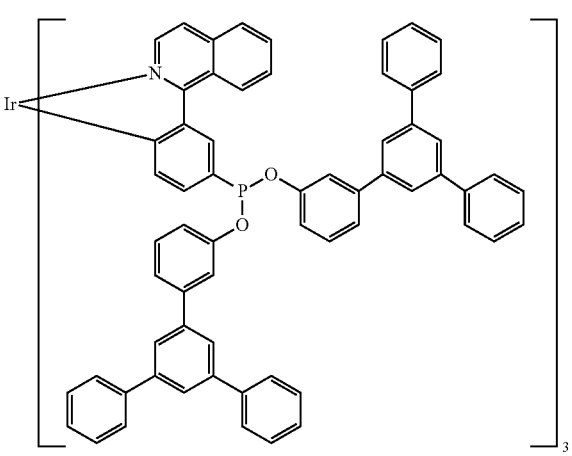
formula (434)

formula (435)
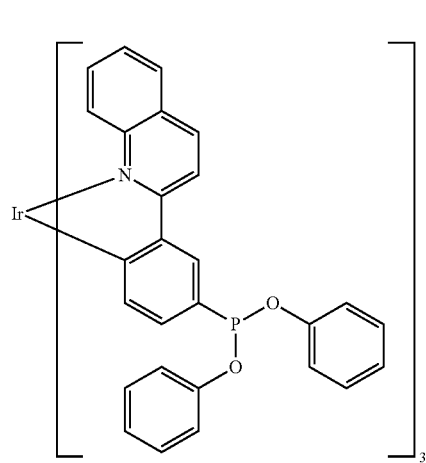
formula (436)
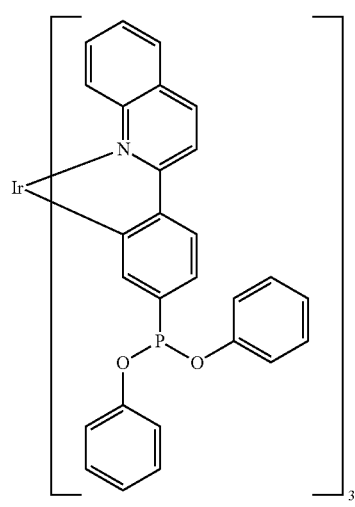
formula (437)
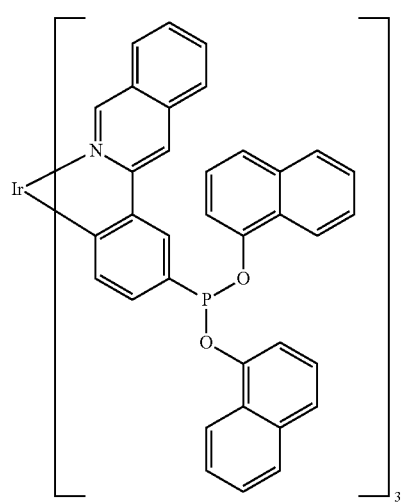
formula (438)
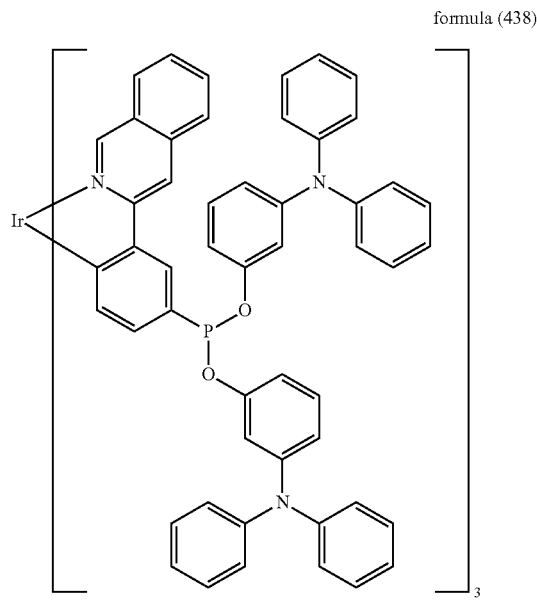
formula (439)
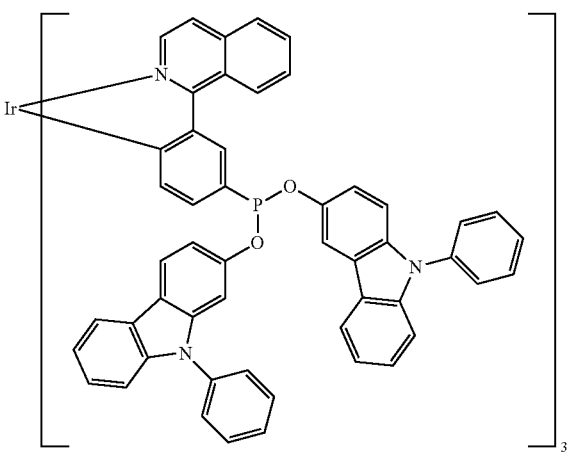
formula (440)
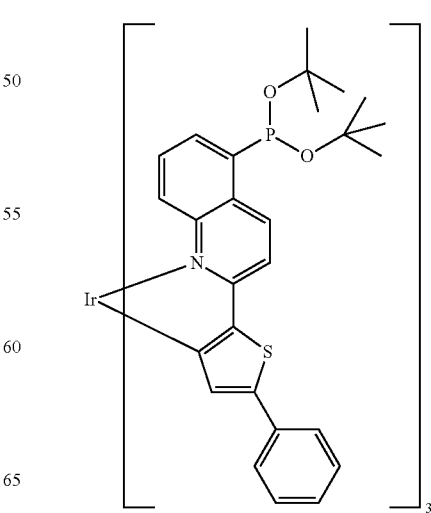

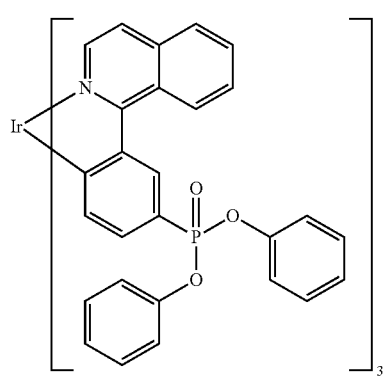
formula (441)
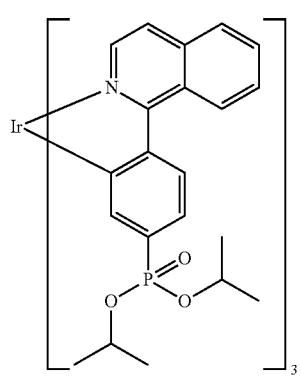
formula (442)
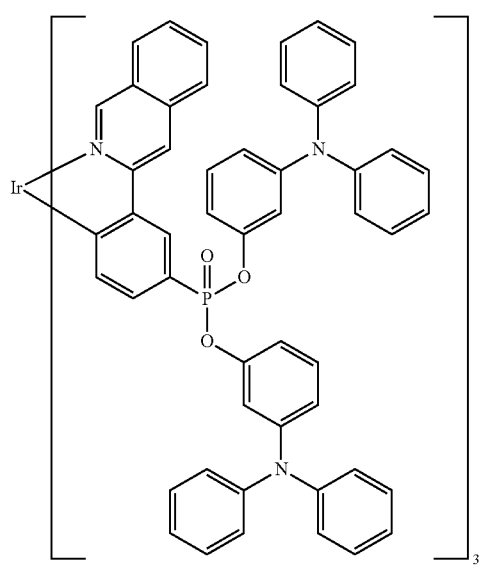
formula (443)
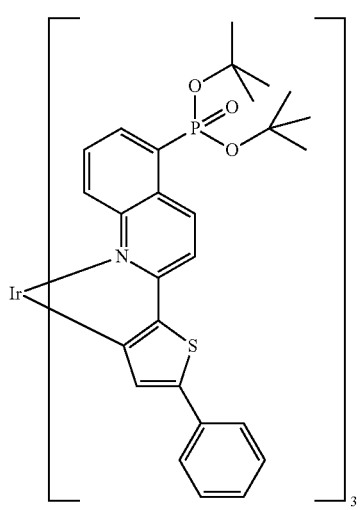
formula (444)
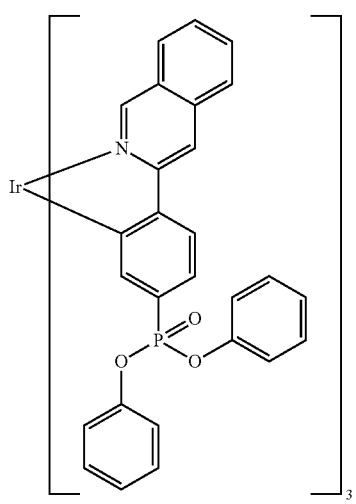
formula (445)
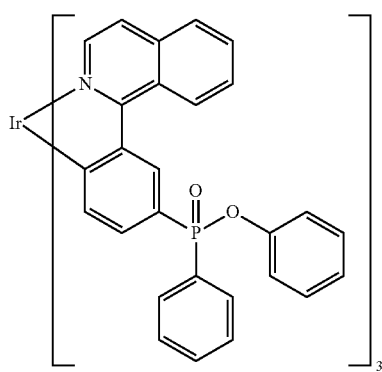
formula (446)

formula (447)
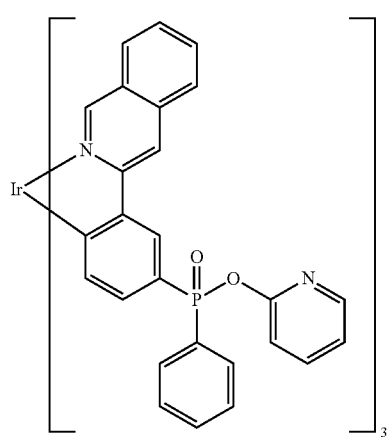
formula (450)
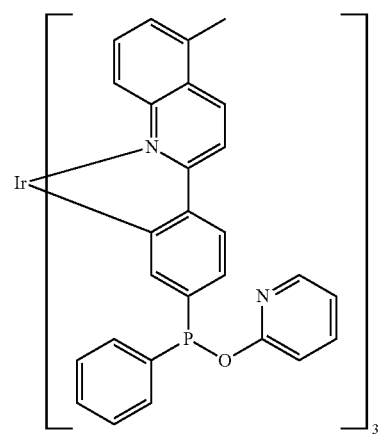
formula (448)
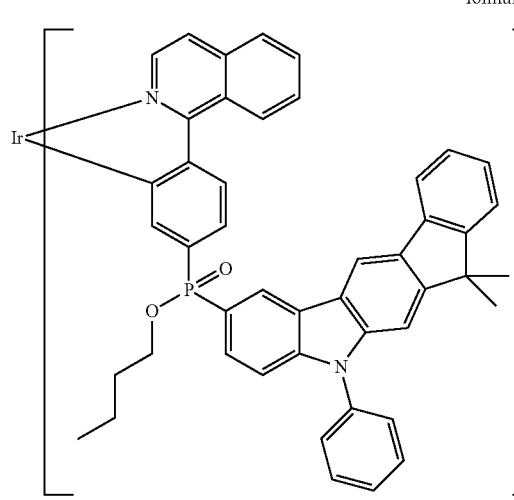
formula (451)
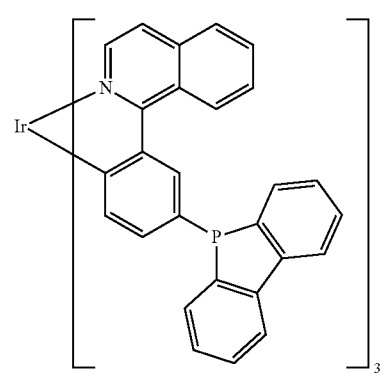
formula (449)
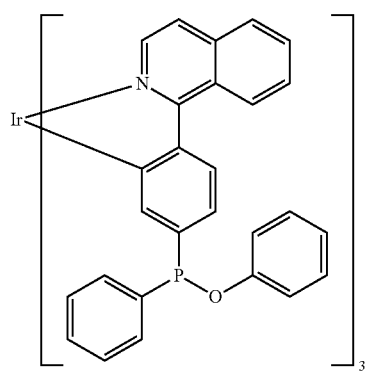
formula (452)
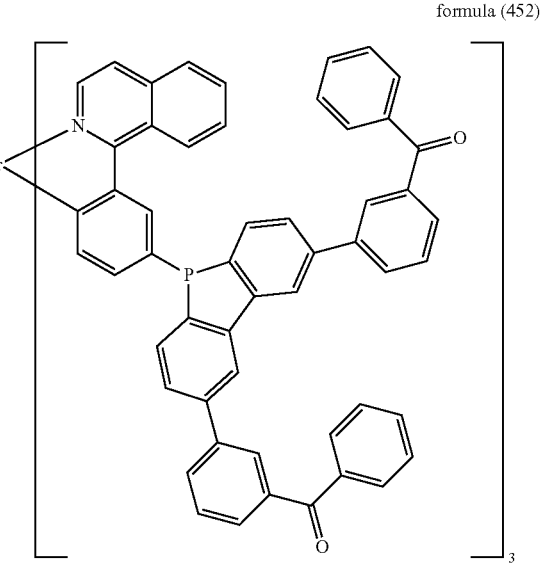

formula (453)
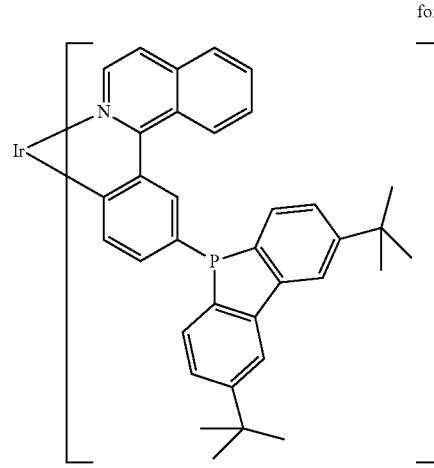
formula (456)
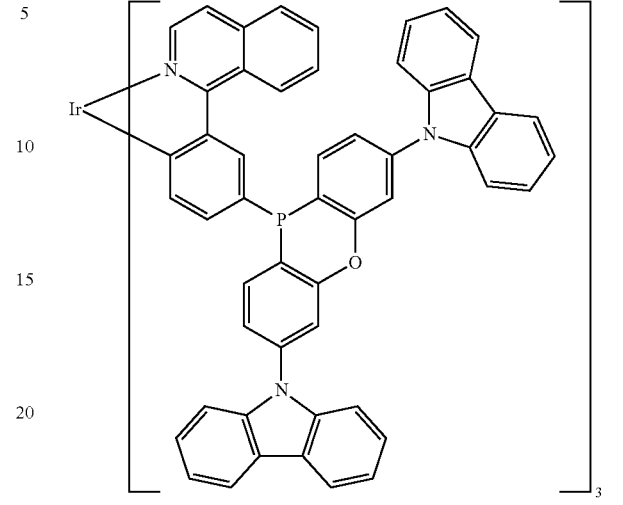
formula (454)
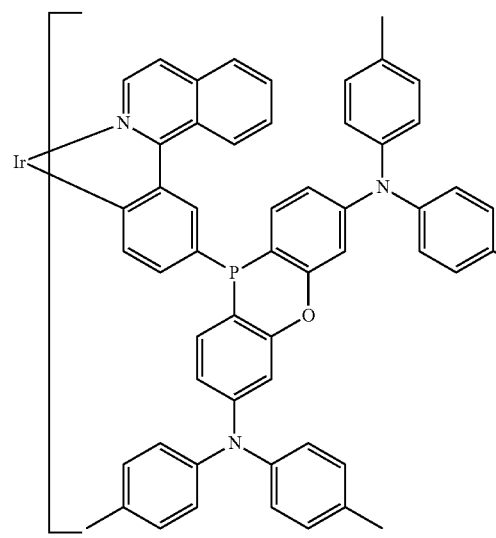
formula (457)
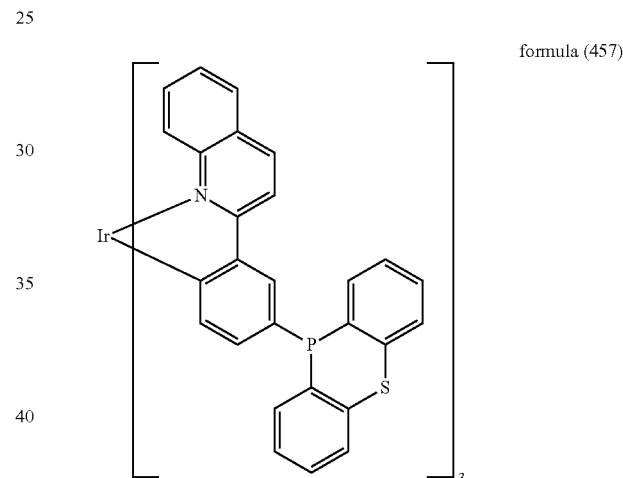
formula (455)
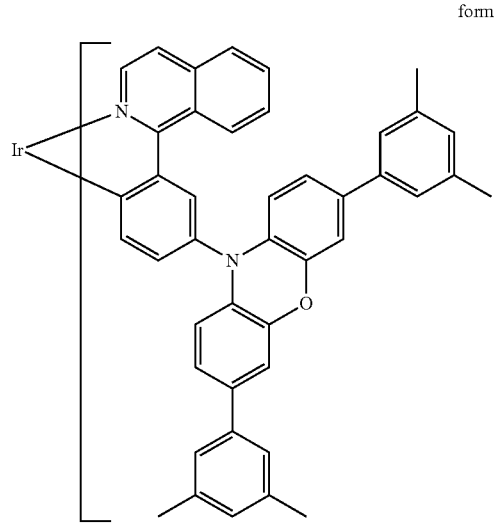
formula (458)
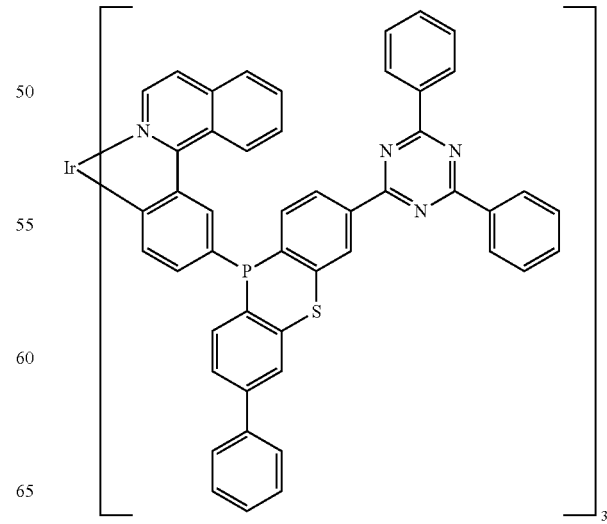

formula (459)
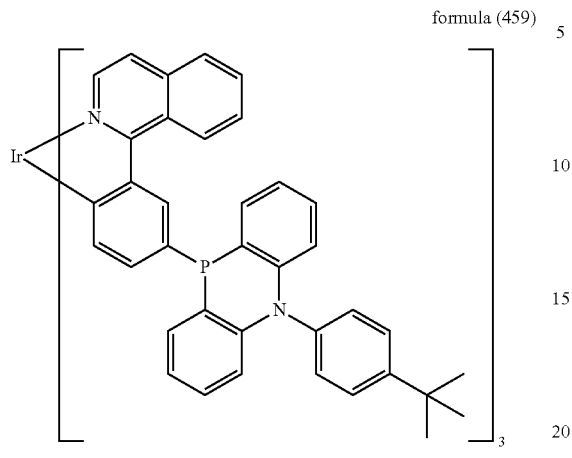
formula (460)
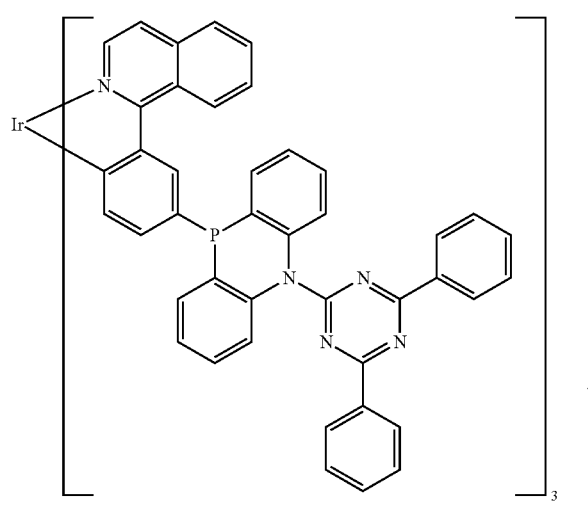
formula (461)
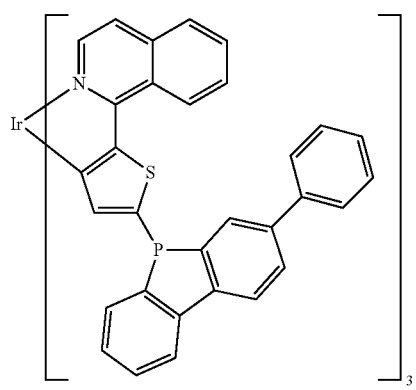
formula (462)
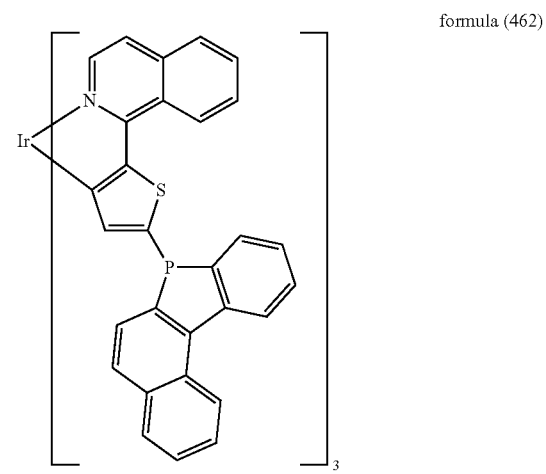
formula (463)
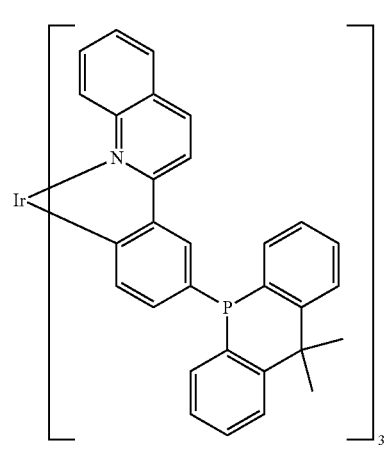
formula (464)
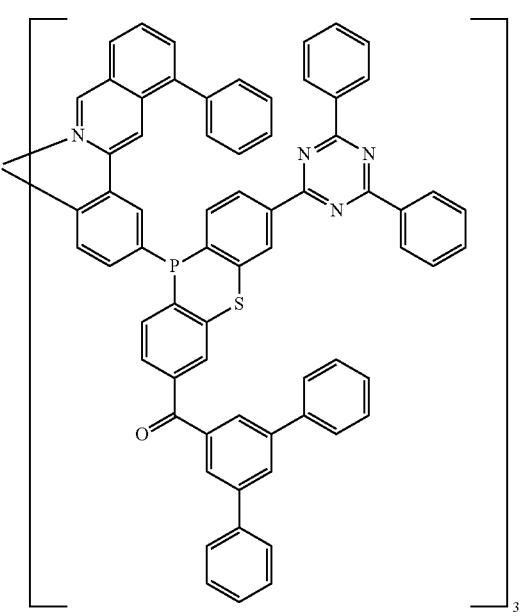

formula (465)
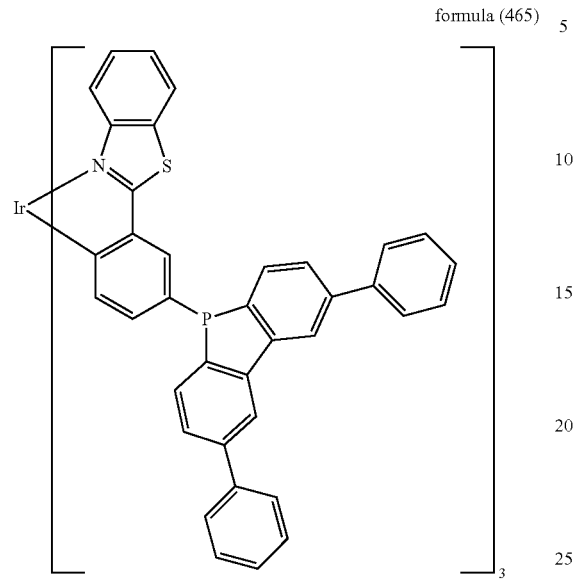
formula (468)
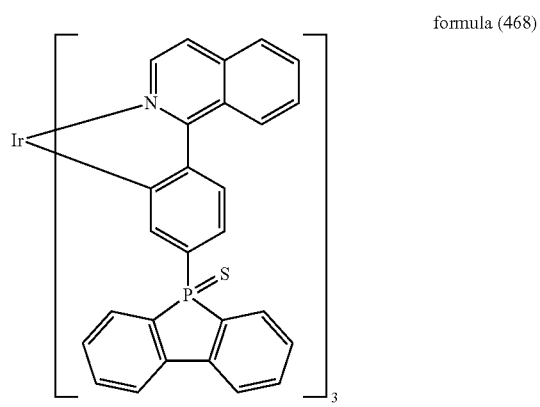
formula (466)
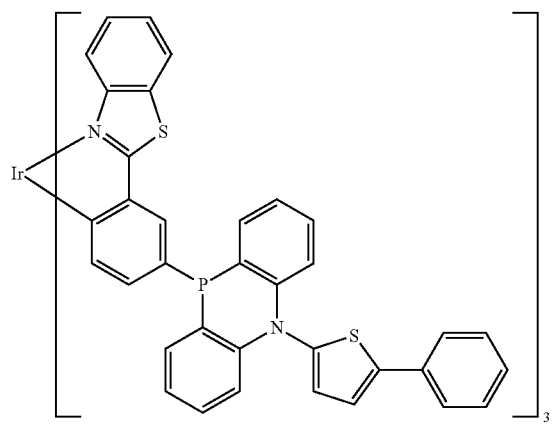
formula (469)
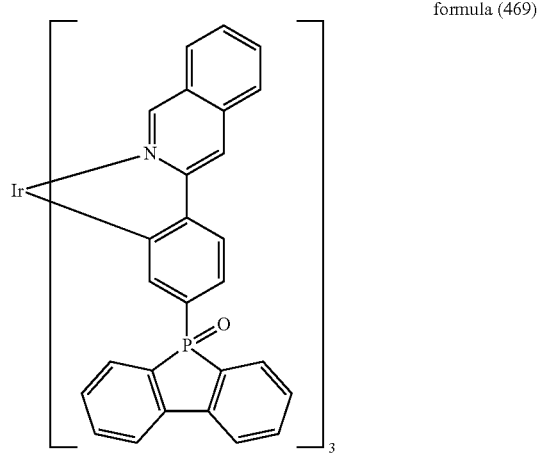
formula (470)
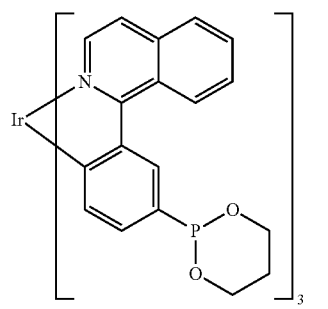
formula (467)
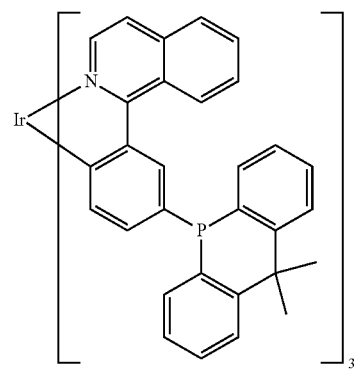
formula (471)
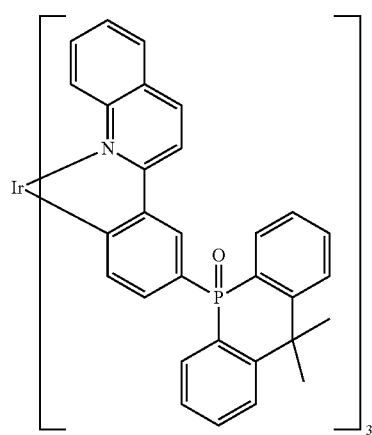

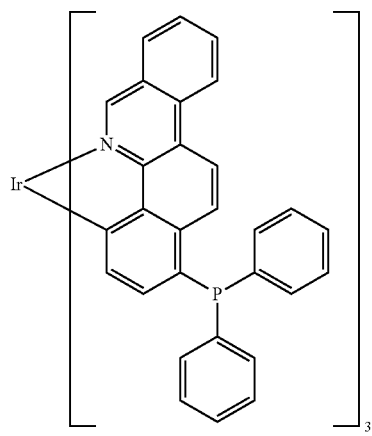
formula (472)
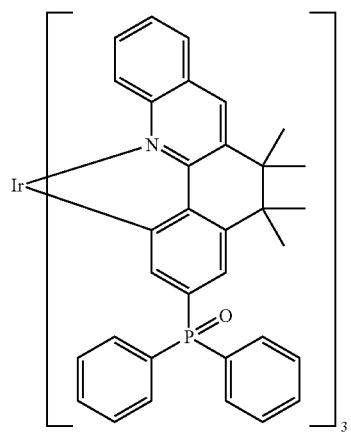
formula (475)
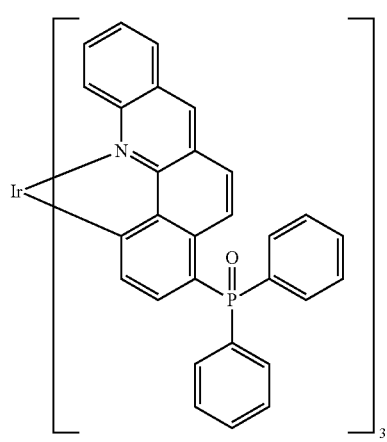
formula (473)
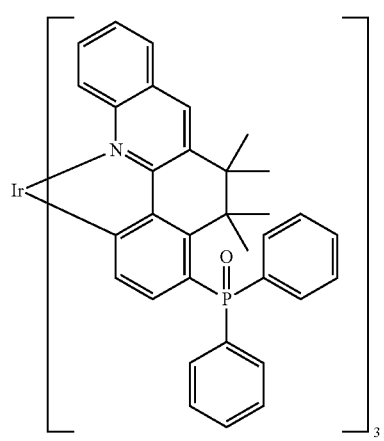
formula (476)
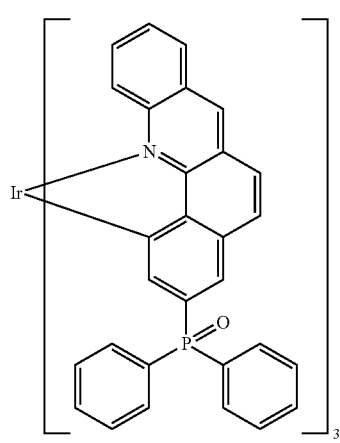
formula (474)
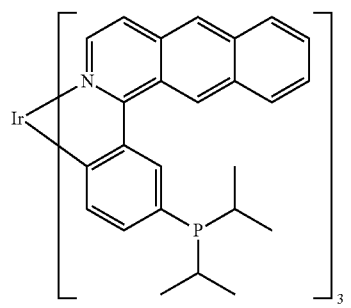
formula (477)

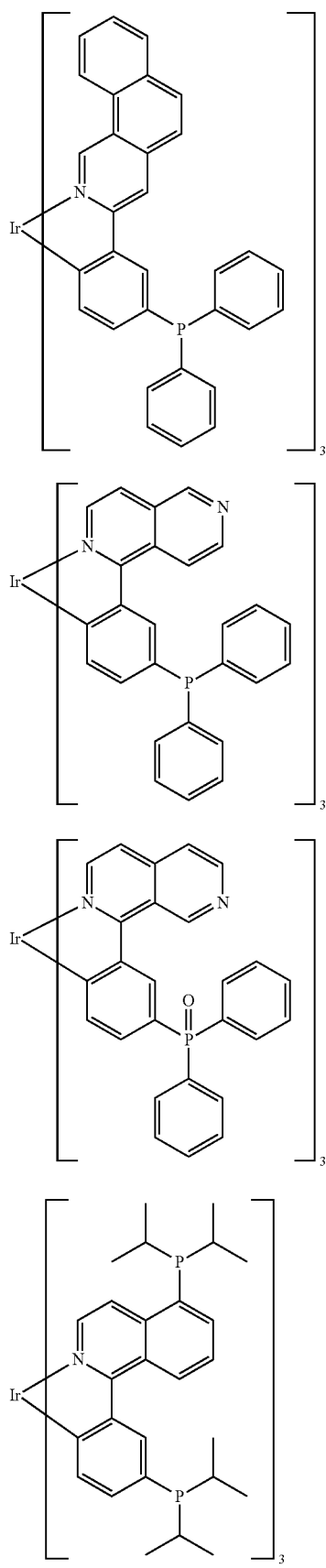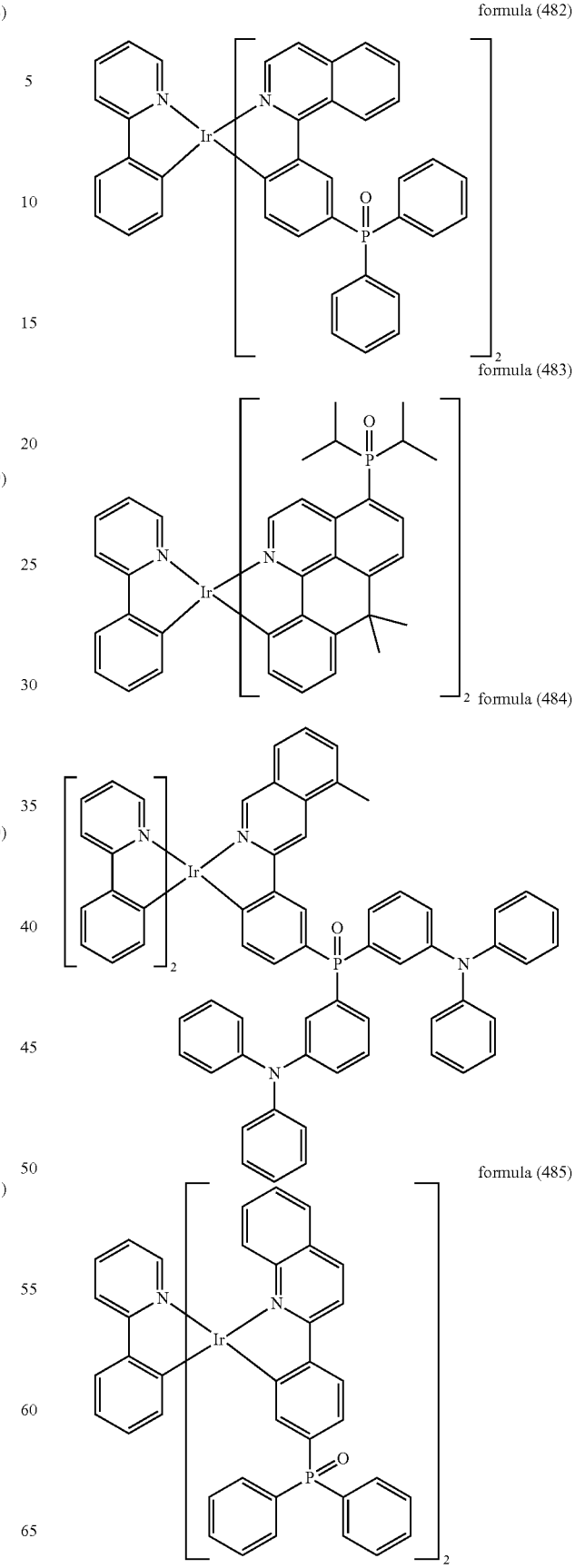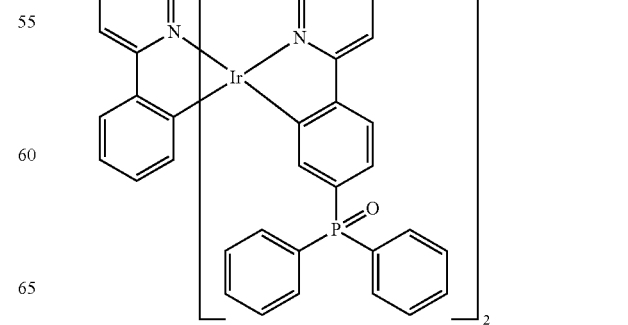

formula (486)
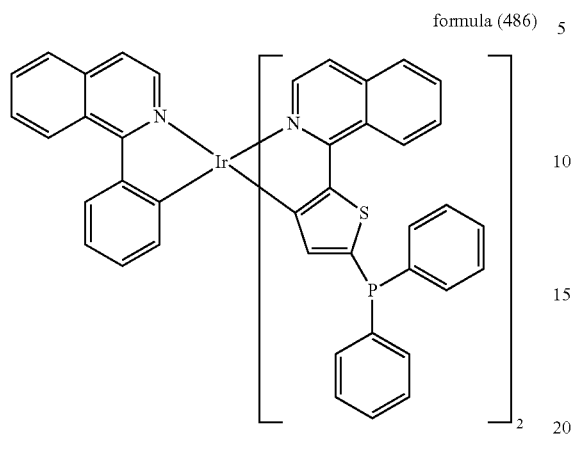
formula (489)
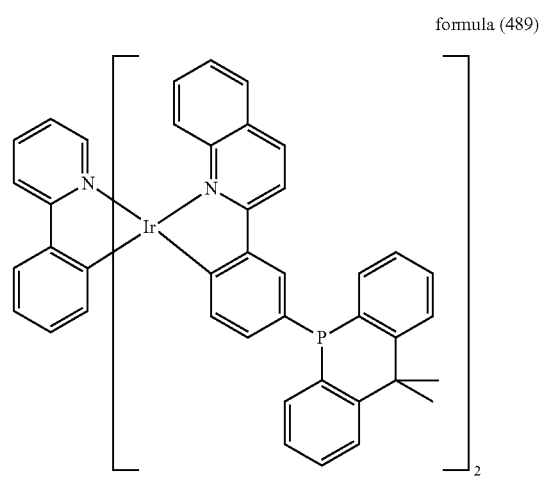
formula (487)
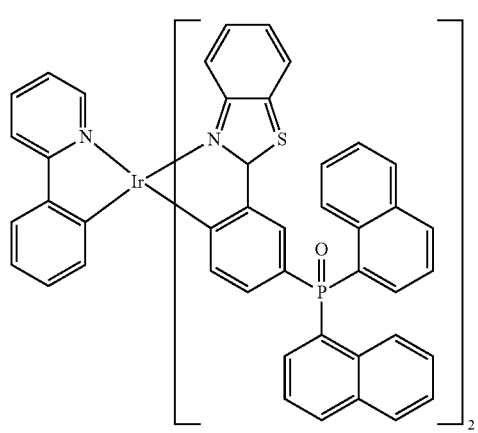
formula (490)
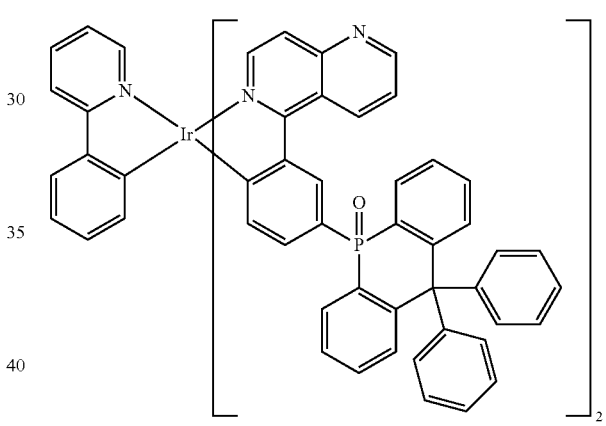
formula (488)
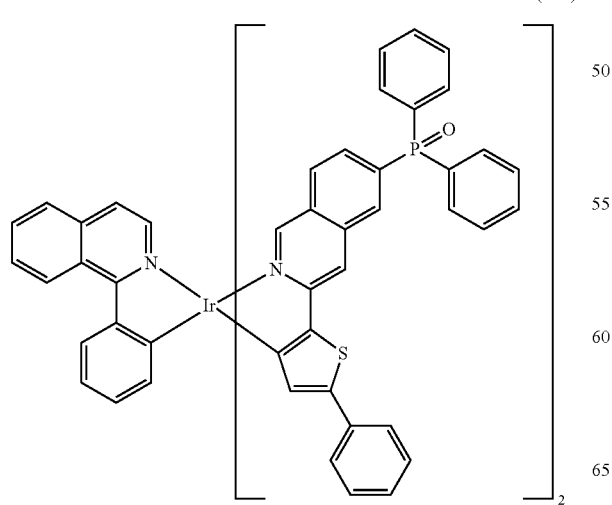
formula (491)
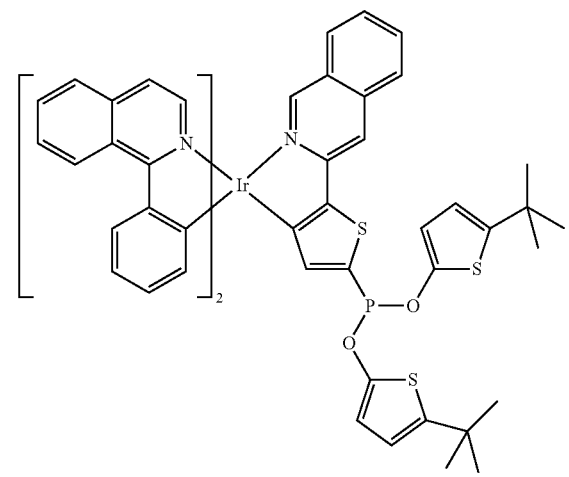

-continued formula (492)

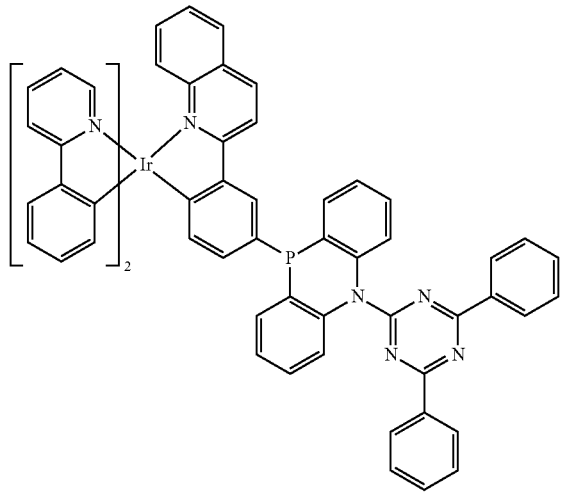

formula (493)

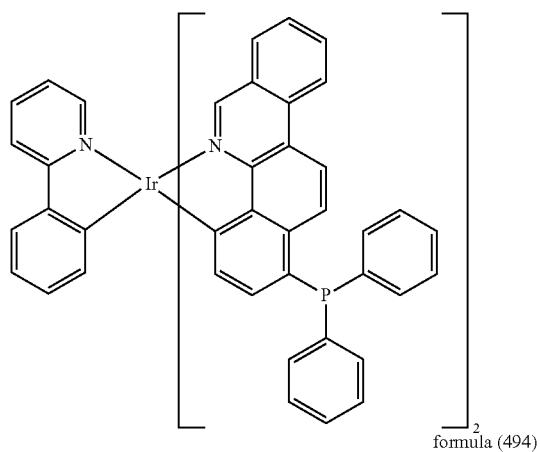

formula (494)

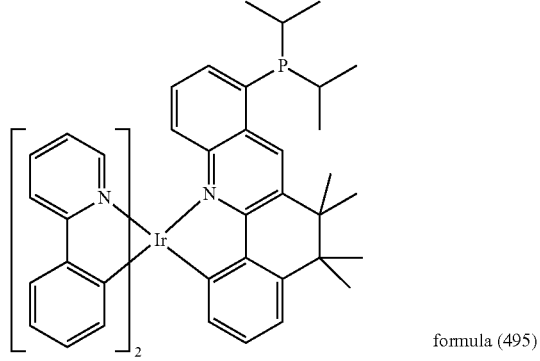

formula (495)

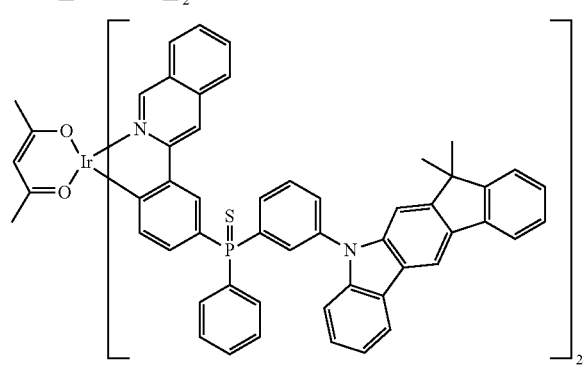

-continued formula (496)

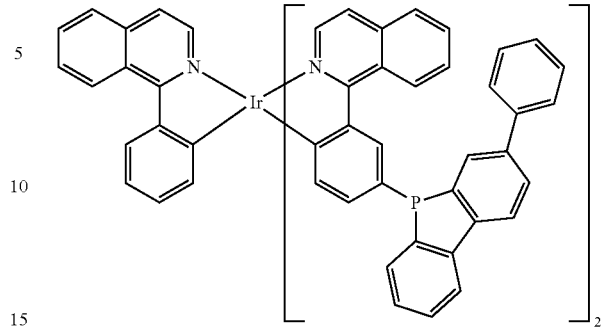

The complexes of the formula (1) described above and the preferred embodiments mentioned above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) indicated above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising, in at least one layer, at least one compound of the formula (1) indicated above. Particular preference is given to organic electroluminescent devices. Active components are generally the organic or inorganic materials, which are introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. It is likewise possible for interlayers, which have, for example, an exciton-blocking function and/or control the charge balance in the electroluminescent device, to be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013), or systems which comprise more than three emitting layers.

In a preferred embodiment of the invention, the organic electroluminescent device comprises the compound of the formula (1) or the preferred embodiments mentioned above as emitting compound in one or more emitting layers.

If the compound of the formula (1) is employed as emitting compound in an emitting layer, it is preferably employed in combination with one or more matrix materials. The mixture of the compound of the formula (1) and the matrix material comprises between 0.1 and 99% by weight, preferably between 0.5 and 40% by weight, particularly preferably between 1 and 30% by weight, in particular between 2 and 25% by weight, of the compound of the formula (1), based on the entire mixture comprising emitter and matrix material. Correspondingly, the mixture comprises between 99 and 1% by weight, preferably between 98 and 60% by weight, particularly preferably between 97 and 70% by weight, in particular between 95 and 75% by weight, of the matrix material, based on the entire mixture comprising emitter and matrix material.

Suitable matrix materials for the compounds according to the invention are ketones, phosphine oxides, sulfoxides and sulfones, for example in accordance with WO 2004/013080, WO 2004/093207, WO 2006/005627 or DE 102008033943.1, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with the applications DE 102009023155.2 and DE 102009031021.5, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 06/117052, triazine derivatives, for example in accordance with the application DE 102008036982.9, WO 2007/063754 or WO 2008/056746, zinc complexes, for example in accordance with EP 652273 or in accordance with WO 2009/062578, diaza- or tetraazasilole derivatives, for example in accordance with DE 102008056688.8, or diazaphosphole derivatives, for example in accordance with DE 102009022858.6.

It may also be preferred to employ a plurality of different matrix materials as a mixture, in particular at least one electron-conducting matrix material and at least one hole-conducting matrix material. A preferred combination is, for example, the use of an aromatic ketone or a triazine with a triarylamine derivative or a carbazole derivative as mixed matrix for the metal complex according to the invention. Preference is likewise also given to mixtures of a hole- or electron-transporting material with a material which is involved in neither hole transport nor electron transport, as disclosed, for example, in DE 102009014513.3.

In a further preferred embodiment of the present invention, the compounds according to the invention can be employed in mixtures with one or more further emitters. Very particular preference is given here to a mixture of the compounds according to the invention with one or more fluorescent emitters. Preference is furthermore given to a mixture with one or more phosphorescent emitters. fluorescent emitters emit principally from excited singlet states, whereas phosphorescent emitters emit light principally from higher spin states (for example triplet and quintet). For the purposes of this invention, the complexes of organic transition metals are taken to be phosphorescent emitters. The further emitters are preferably organic compounds.

In a particularly preferred embodiment of the present invention, the compounds according to the invention are mixed with 3 further emitters, in a particularly preferred embodiment with 2 further emitters and in an especially very preferred embodiment with one further emitter.

In a further preferred embodiment of the present invention, the emitter mixtures comprise 3, particularly preferably 2 and very particularly preferably one compound according to the invention.

In a particularly preferred embodiment of the present invention, the emitter mixtures comprise precisely one of the compounds according to the invention and precisely one further emitter.

It is furthermore preferred for the purposes of the present invention for the absorption spectra of at least one emitter and the emission spectrum of at least one other emitter of the mixture to overlap, simplifying energy transfer (double doping) between the emitters. The energy transfer here can take place by various mechanisms. Non-definitive examples of this are Förster or Dexter energy transfer.

The emitter mixtures described preferably comprise at least two emitters which both emit red light. Preference is furthermore given to emitter mixtures comprising at least one emitter which emits red light and at least one emitter which emits green light.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys of an alkali or alkaline-earth metal and silver, for example an alloy of magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to enable either irradiation of the organic material (O-SCs) or the coupling-out of light (OLEDs/PLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive doped organic materials, in particular conductive doped polymers.

In general, all materials as used for the layers in accordance with the prior art can be used in the further layers, and the person skilled in the art will be able to combine each of these materials with the materials according to the invention in an electronic device without inventive step.

The device is correspondingly (depending on the application) structured, provided with contacts and finally hermetically sealed, since the lifetime of devices of this type is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Since the compounds of the formula (1) according to the invention have very good solubility in organic solvents, they are particularly suitable for processing from solution.

The organic electroluminescent device can also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments mentioned above.

For processing from solution, solutions or formulations of the compounds of the formula (1) are necessary. It may also be preferred to use mixtures of two or more solvents. Suitable and preferred solvents are, for example, toluene, anisole, o-, m- or p-xylenes, methyl benzoate, dimethylanisoles, mesitylenes, tetralin, veratrol, tetrahydrofuran (THF), methyl-THF, THP, chlorobenzene, dioxane, or mixtures of these solvents.

The present invention therefore furthermore relates to a solution or formulation comprising at least one compound of the formula (1) and one or more solvents, in particular organic solvents. The way in which solutions of this type can be prepared is known to the person skilled in the art and is described, for example, in WO 02/072714, WO 2003/019694 and the literature cited therein.

The electronic devices according to the invention, in particular organic electroluminescent devices, are distinguished by the following surprising advantages over the prior art:

1. The compounds of the formula (1) have very good solubility in a multiplicity of common organic solvents and are therefore very highly suitable for processing from solution. In particular, the compounds according to the invention have higher solubility than the similar compounds described in the prior art.
2. Organic electroluminescent devices comprising compounds of the formula (1) as emitting materials have an excellent lifetime. In particular, the lifetime is better than in the case of similar compounds in accordance with the prior art.
3. Organic electroluminescent devices comprising compounds of the formula (1) as emitting materials have excellent efficiency. In particular, the efficiency is better than in the case of similar compounds in accordance with the prior art.

These above-mentioned advantages are not accompanied by an impairment in the other electronic properties.

The compounds according to the invention are capable of emitting light under certain prerequisites. These compounds are thus very versatile.

Some of the principal areas of application here are display or illumination technologies. It is furthermore particularly advantageous to employ the compounds and devices comprising these compounds in the area of phototherapy.

The present invention therefore furthermore relates to the use of the compounds according to the invention and devices comprising the compounds for the treatment, prophylaxis and diagnosis of diseases. The present invention still furthermore relates to the use of the compounds according to the invention and devices comprising the compounds for the treatment and prophylaxis of cosmetic conditions.

The present invention furthermore relates to the use of the compounds according to the invention for the production of devices for the therapy, prophylaxis and/or diagnosis of therapeutic diseases.

Phototherapy or light therapy is used in many medical and/or cosmetic areas. The compounds according to the invention and the devices comprising these compounds can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) and disinfection and sterilisation in general. Phototherapy or light therapy can be used for the treatment of not only humans or animals, but also any other type of living or non-living materials. These include, for example, fungi, bacteria, microbes, viruses, eukaryotes, prokaryotes, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. The treatment or irradiation according to the invention can in addition also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers and desensitisation of the skin.

Particular preference is given for the purposes of the invention to the treatment and/or prophylaxis of psoriasis, acne, cellulite, skin wrinkling, skin ageing, jaundice and vitiligo.

Further areas of application according to the invention for the compositions and/or devices comprising the compositions according to the invention are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds and/or devices comprising the compounds according to the invention are selected from winter depression, sleeping sickness, irradiation for improving the mood, the reduction in pain, particularly muscular pain caused by, for example, tension or joint pain, elimination of the stiffness of joints and the whitening of the teeth (bleaching).

Further areas of application according to the invention for the compounds and/or devices comprising the compounds according to the invention are selected from the group of disinfections. The compounds according to the invention and/or the devices according to the invention can be used for the treatment of any type of objects (non-living materials) or subjects (living materials such as, for example, humans and animals) for the purposes of disinfection. This includes, for example, the disinfection of wounds, the reduction in bacteria, the disinfection of surgical instruments or other articles, the disinfection of foods, of liquids, in particular water, drinking water and other drinks, the disinfection of mucous membranes and gums and teeth. Disinfection here is taken to mean the reduction in the living microbiological causative agents of undesired effects, such as bacteria and germs.

For the purposes of the phototherapy mentioned above, devices comprising the compounds according to the invention preferably emit light having a wavelength between 250 and 1250 nm, particularly preferably between 300 and 1000 nm and especially preferably between 400 and 850 nm.

In a particularly preferred embodiment of the present invention, the compounds according to the invention are employed in an organic light-emitting diode (OLED) or an organic light-emitting electrochemical cell (OLEC) for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, caps, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for reuse or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples without wishing it to be restricted thereby.

EXAMPLES

The following syntheses are carried out, unless indicated otherwise, under a protective-gas atmosphere in dried solvents. The starting materials II and IV are commercially available (for example from VWR Chemikalien). Compounds I and VIII can be prepared analogously to those in WO 02/068435. Compound VI can be prepared in accordance with Organic letters, 2005, 7, 19, 4277-4280.

Example 1

Preparation of Compound T1

Synthetic Procedure for the Preparation of Compound T1:

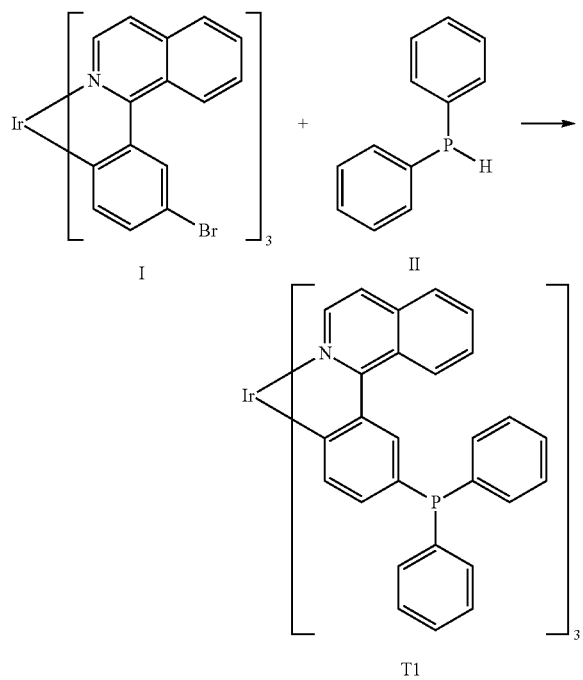

5.0 g (4.8 mmol) of compound I, and 1.1 g (5.3 mmol) of potassium acetate are suspended in 100 ml of degassed dimethylacetamide. 11 mg (0.05 mmol) of Pd(OAc)$_2$ are added to this suspension. 2.7 g (14.4 mmol) of compound II are added. The reaction mixture is heated under reflux for 4 days. After cooling, the reaction solution is poured into 175 ml of water. 200 ml of dichloromethane are then added. The organic phase is separated off, washed three times with 75 ml of water and subsequently evaporated to dryness. The residue is washed with ethanol and recrystallised from toluene and finally dried under reduced pressure. The yield is 5.3 g (3.9 mmol), corresponding to 80.7% of theory.

Example 2

Preparation of Compound T2

Synthetic Procedure for the Preparation of Compound T2:

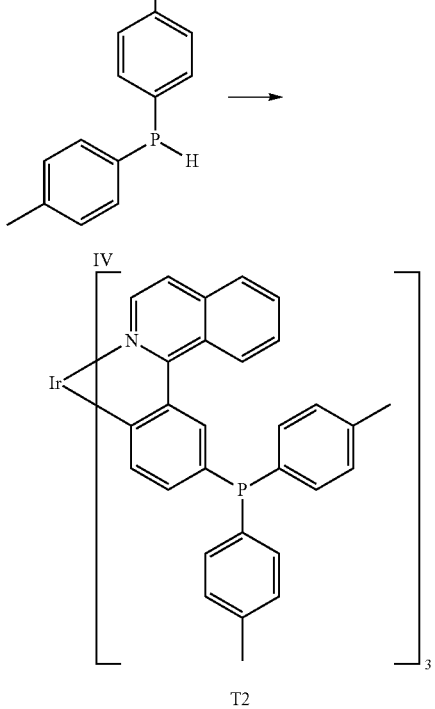

The synthesis is carried out analogously to that of compound TI in Example 1 using 5.0 g (4.8 mmol) of compound I, where compound II is replaced by 3.1 g (14.4 mmol) of compound IV. The yield is 5.9 g (4.1 mmol), corresponding to 85.2% of theory.

Example 3

Preparation of Compound T3

Synthetic Procedure for the Preparation of Compound T3:

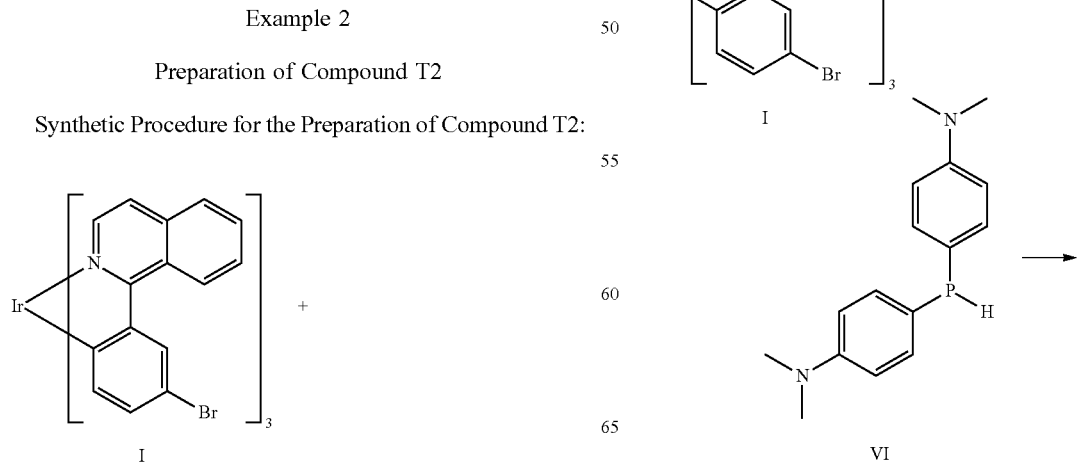

-continued

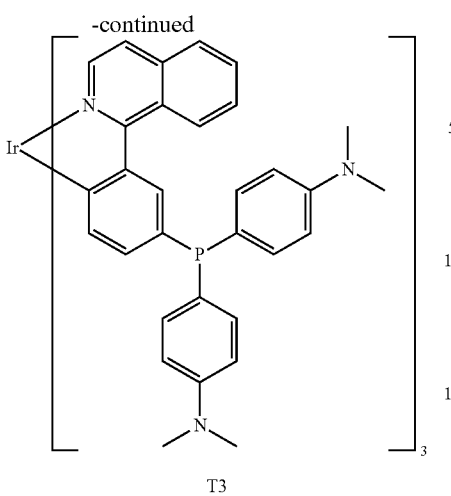

T3

The synthesis is carried out analogously to that of compound TI in Example 1 using 5.0 g (4.8 mmol) of compound 1, where compound II is replaced by 3.9 g (14.4 mmol) of compound VI. The yield is 5.3 g (3.3 mmol), corresponding to 68.8% of theory.

Example 4

Preparation of Compound T4

Synthetic Procedure for the Preparation of Compound T4:

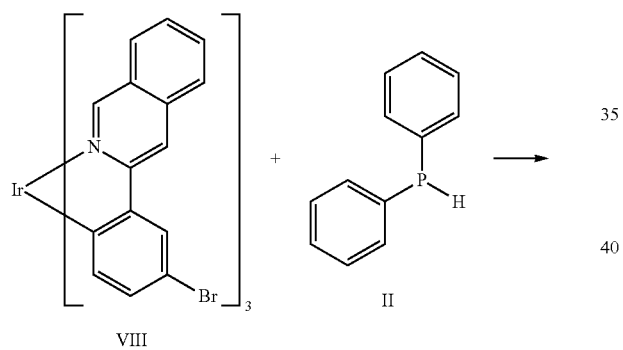

The synthesis is carried out analogously to that of compound TI in Example 1 using 2.7 g (14.4 mmol) of compound II, where compound I is replaced by 5.0 g (4.8 mmol) of compound VIII. The yield is 5.1 g (3.7 mmol), corresponding to 77.9% of theory.

Example 5

Preparation of Compound T5

Synthetic Procedure for the Preparation of Compound T5:

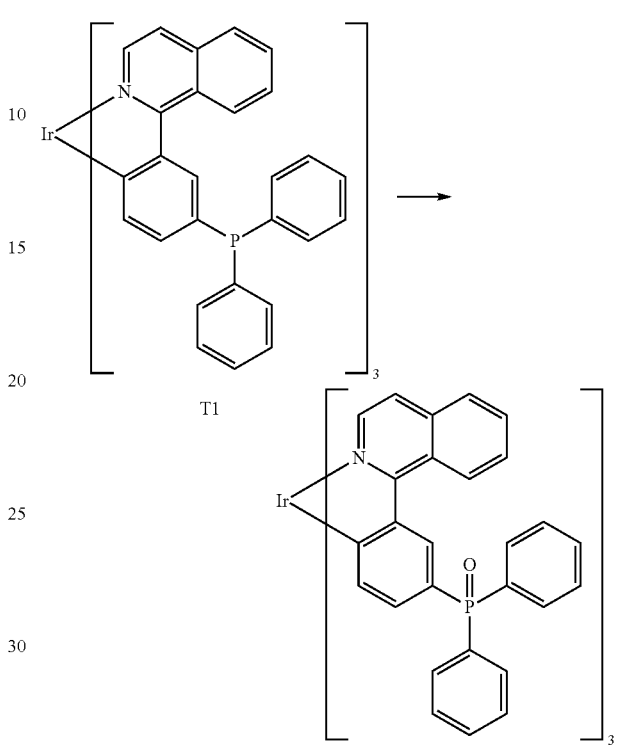

3.8 g (14.6 mmol) of N-(phenylsulfonyl)-3-phenyloxaziridine are added to a solution of 6.0 g (4.4 mmol) of compound TI in 100 ml of dichloromethane. The reaction mixture is stirred at room temperature for 20 h. The evaporated residue is purified through a silica-gel column. The solid is recrystallised from toluene and dried under reduced pressure. The yield is 1.6 g (1.1 mmol), corresponding to 25.4% of theory.

Example 6

Preparation of Compound T6

Synthetic Procedure for the Preparation of Compound T6:

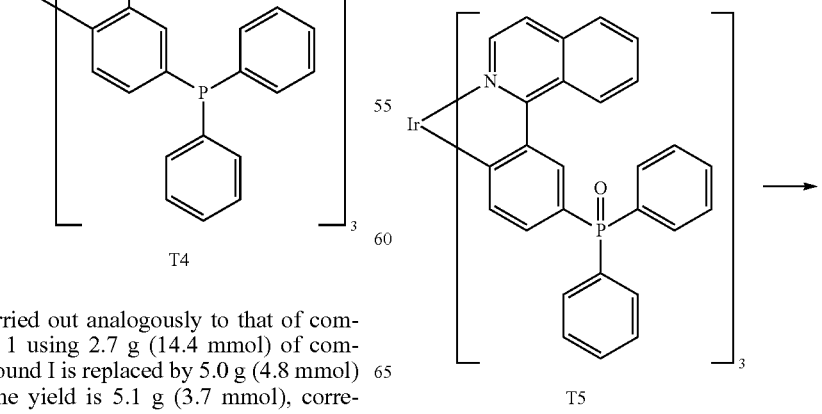

T5

-continued

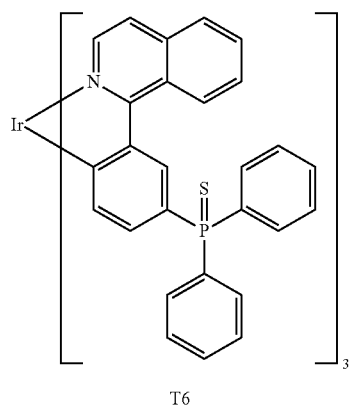

T6

7.5 g (5.3 mmol) of compound T5 and 3.2 g (8.0 mmol) of 2,4-bis-(4-methoxyphenyl)-1,3,2,4-dithiadiphosphetane 2,4-disulfide (Lawesson's reagent) are suspended in 100 ml of degassed toluene. The suspension is heated under reflux for 20 h. After cooling, the reaction mixture is filtered off. The solid is recrystallised from toluene. The yield is 5.1 g (3.5 mmol), corresponding to 65.2% of theory Examples 7 to 12

Production and Characterisation of Organic Electroluminescent Devices Comprising the Compounds According to the Invention The structures of matrix materials TMM-1 (synthesised in accordance with DE 102008036982) and TMM-2 (synthesised in accordance with DE 102008017591) used below are depicted below.

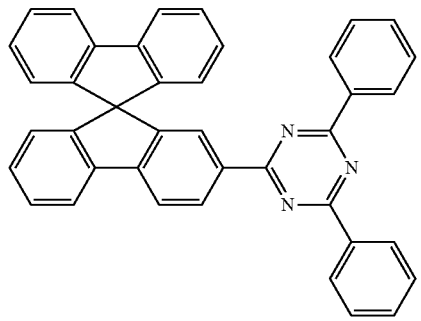

TMM-1

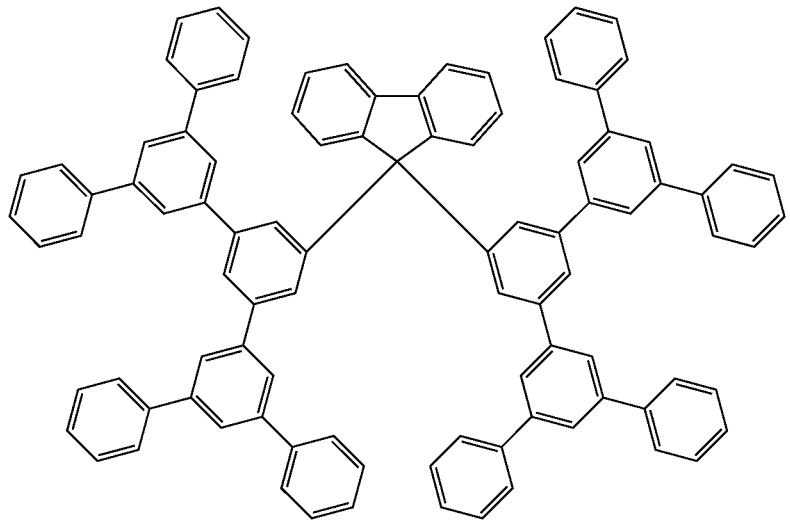

TMM-2

The materials according to the invention can be used from solution, where they result in devices having good properties which are simple to produce. The production of such components is based on the production of polymeric light-emitting diodes (PLEDs), which has already been described many times in the literature (for example in WO 2004/037887). In the present case, compounds T1 to T6 according to the invention are dissolved in toluene. The typical solids content of such solutions is between 16 and 25 g/l if, as here, the typical layer thickness of 80 nm for a device is to be achieved by means of spin coating. The electroluminescent device used exhibits the following structure: ITO/PEDOT:PSS/interlayer/EML/cathode, where EML represents the emission layer. Structured ITO substrates and the material for the so-called buffer layer (PEDOT, more accurately PEDOT:PSS) are commercially available (ITO from Technoprint and others, PEDOT:PSS as Clevios Baytron P aqueous dispersion from H.C. Starck). The interlayer used serves for hole injection; in this case, HIL-012 from Merck KGaA, Germany, was used. The emission layer is applied by spin coating in an inert-gas atmosphere, in the present case argon, and dried by heating at 120° C. for 10 min. Finally, a barium and aluminium cathode is applied by vacuum vapour deposition. A hole-blocking layer and/or an electron-transport layer can also be applied between the emitting layer (EML) and the cathode by vapour deposition. Furthermore, the interlayer may also be replaced by one or more layers, which merely have to satisfy the condition of not being detached again by the subsequent processing step of deposition of the emitting layer from solution.

The devices are characterised by in a standard manner by means of methods which are well known to the average person skilled in the art in the area. However, the OLEDs mentioned here have not yet been optimised. Table 1 summarises the data obtained. In the case of the processed devices, it is apparent that the materials according to the invention are superior to those previously available in efficiency and/or lifetime.

TABLE 1

Results with solution-processed materials in the device configuration: ITO/PEDOT:PSS/interlayer/EML/cathode

| Ex. | EML 80 nm | Max. eff. [cd/A] | Voltage [V] at 100 cd/m² | CIE (x/y) | Lifetime [h], initial luminance 1000 cd/m² |
|---|---|---|---|---|---|
| 7 | TMM-1:TMM-2:T-1 | 8 | 5.1 | 0.66/0.33 | 6500 |
| 8 | TMM-1:TMM-2:T-2 | 7 | 5.0 | 0.67/0.33 | 8000 |
| 9 | TMM-1:TMM-2:T-3 | 7 | 4.9 | 0.65/0.32 | 10000 |
| 10 | TMM-1:TMM-2:T-4 | 10 | 5.3 | 0.61/0.38 | 10500 |
| 11 | TMM-1:TMM-2:T-5 | 8 | 5.2 | 0.67/0.33 | 15000 |
| 12 | TMM-1:TMM-2:T-6 | 7 | 5.3 | 0.67/0.33 | 12000 |

The invention claimed is:

1. An electronic device comprising a compound of the formula (1)

$$M(L)_n(L')_m \quad \text{formula (1)}$$

where the compound contains a moiety $M(L)_n$ of the formulae (24), (26) or (28)

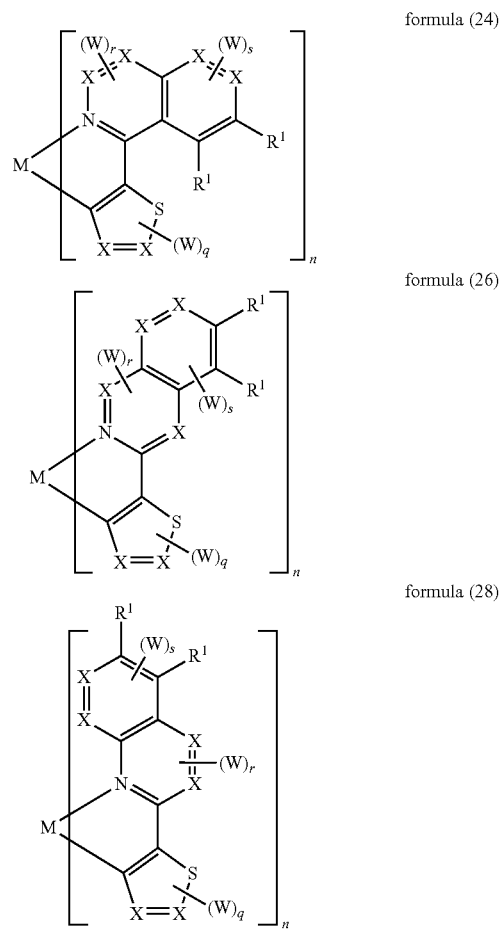

wherein
M is bonded to a bidentate ligand L via a nitrogen atom N and via a carbon atom C;
M is iridium or platinum;
X is $CR^1$;
$R^1$ is, identically or differently on each occurrence, H, D, F, Cl, Br, I, $N(R^2)_2$, CN, $NO_2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which optionally in each case is substituted by one or more radicals $R^2$, or an aryloxy or heteroaryloxy group having 5 to 60 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals R², or a combination of two or more of these groups; two or more radicals R¹ here may also form a mono- or polycyclic, aliphatic, aromatic and/or benzo-fused ring system with one another;

L' is, identically or differently on each occurrence, a co-ligand;

W is, identically or differently on each occurrence, a radical of the formulae (3) and (4)

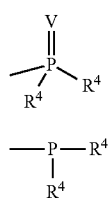

formula (3)

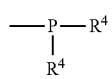

formula (4)

where V is equal to S or O;

R⁴ is, identically or differently on each occurrence, H, D, F, Cl, Br, I, N(R²)₂, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R², where one or more non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by D, F, Cl, Br, I, CN or NO₂, or an aromatic or heteroaromatic ring system having 5 to 60 aromatic ring atoms, which optionally in each case is substituted by one or more radicals R², or an aryloxy, arylalkoxy, alkylaryloxy or heteroaryloxy group having 5 to 60 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals R², or a combination of two or more of these groups; two or more adjacent radicals R⁴ here may form a mono- or polycyclic, aliphatic, aromatic and/or benzo-fused ring system with one another;

R² is, identically or differently on each occurrence, H, D, F, Cl, Br, I, N(R³)₂, CN, NO₂, Si(R³)₃, B(OR³)₂, C(=O)R³, P(=O)(R³)₂, S(=O)R³, S(=O)₂R³, OSO₂R³, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, or an aromatic or heteroaromatic ring system having 5 to 60 aromatic ring atoms, which optionally in each case is substituted by one or more radicals R³, or an aryloxy, arylalkoxy, alkylaryloxy or heteroaryloxy group having 5 to 60 aromatic ring atoms, which is optionally substituted by one or more radicals R³, or a diarylamino group, diheteroarylamino group or arylheteroarylamino group having 10 to 40 aromatic ring atoms, which is optionally substituted by one or more radicals R³, or a combination of two or more of these groups; two or more adjacent radicals R² here may form a mono- or polycyclic, aliphatic or aromatic ring system with one another;

R³ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents R³ here optionally also forms a mono- or polycyclic, aliphatic or aromatic ring system with one another;

q is an integer greater than or equal to 0; and q+r+s=1;

n is 1, 2 or 3 for M equal to iridium and is 1 or 2 for M equal to platinum;

m is 0, 1 or 2 for M equal to iridium and is 0 or 1 for M equal to platinum;

the indices n and m here are selected so that the coordination number on the metal corresponds to 6 for M equal to iridium and corresponds to 4 for M equal to platinum.

2. The electronic device according to claim 1, wherein the radical W is given by the formulae (110) to (115)

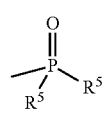

formula (110)

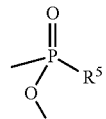

formula (111)

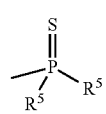

formula (112)

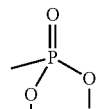

formula (113)

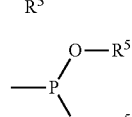

formula (114)

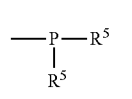

formula (115)

where

R⁵ is, identically or differently on each occurrence, H, D, a straight-chain alkyl or thioalkoxy group having 1 to 40 C atoms or a straight-chain alkenyl or alkynyl group having 2 to 40 C atoms or a branched or cyclic alkyl, alkenyl, alkynyl or thioalkoxy group having 3 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which optionally in each case is substituted by one or more radicals $R^2$, or an aryloxy or heteroaryloxy group having 5 to 60 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$, or a combination of two or more of these groups; two or more radicals $R^5$ optionally forms a mono- or polycyclic, aliphatic, aromatic and/or benzo-fused ring system with one another.

3. The electronic device according to claim 1, wherein M is equal to iridium.

4. The electronic device according to claim 1, wherein m=0.

5. The electronic device according to claim 1, wherein the electronic device is an organic electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell or an organic laser diode.

6. The electronic device according to claim 1, wherein the electronic device is an organic electroluminescent device which comprises the compound of formula (1) employed as emitting compound in one or more emitting layers.

7. The electronic device according to claim 1, wherein the electronic device is an organic electroluminescent device which comprises the compound of formula (1) employed as emitting compound in one or more emitting layers, in combination with a matrix material.

8. The electronic device according to claim 7, wherein the matrix material is ketone, phosphine oxide, sulfoxide, sulfone, triarylamine, carbazole derivative, indolocarbazole derivative, indenocarbazole derivative, azacarbazole derivative, bipolar matrix material, silane, azaborole, boronic ester, triazine derivative, zinc complex, diaza- or tetraazasilole derivative or diazaphosphole derivative or mixtures of these matrix materials.

9. A process for the therapy and/or diagnosis of diseases and/or cosmetic conditions which comprises utilizing the electronic device according to claim 1.

* * * * *